US008460913B2

(12) United States Patent
Kamrud et al.

(10) Patent No.: US 8,460,913 B2
(45) Date of Patent: Jun. 11, 2013

(54) PROMOTERLESS CASSETTES FOR EXPRESSION OF ALPHA VIRUS STRUCTURAL PROTEINS

(75) Inventors: Kurt I. Kamrud, Apex, NC (US); Jonathan F. Smith, Cary, NC (US); Maureen Maughan, Durham, NC (US)

(73) Assignee: Alpha Vax, Inc., Research Triangle Park, NC (US)

( * ) Notice: Subject to any disclaimer, the term of this patent is extended or adjusted under 35 U.S.C. 154(b) by 726 days.

(21) Appl. No.: 12/665,497

(22) PCT Filed: Jun. 20, 2008

(86) PCT No.: PCT/US2008/007701
§ 371 (c)(1),
(2), (4) Date: Dec. 18, 2009

(87) PCT Pub. No.: WO2008/156829
PCT Pub. Date: Dec. 24, 2008

(65) Prior Publication Data
US 2010/0183665 A1    Jul. 22, 2010

Related U.S. Application Data

(60) Provisional application No. 60/936,637, filed on Jun. 21, 2007.

(51) Int. Cl.
*C12N 7/02*    (2006.01)
(52) U.S. Cl.
USPC .................. 435/235.1; 435/239; 435/462
(58) Field of Classification Search
None
See application file for complete search history.

(56) References Cited

U.S. PATENT DOCUMENTS

| | | |
|---|---|---|
| 4,650,764 A | 3/1987 | Temin et al. |
| 4,708,871 A | 11/1987 | Geysen |
| 5,091,309 A | 2/1992 | Schlesinger et al. |
| 5,185,440 A | 2/1993 | Davis et al. |
| 5,217,879 A | 6/1993 | Huang et al. |
| 5,505,947 A | 4/1996 | Johnston et al. |
| 5,521,082 A | 5/1996 | Lewis et al. |
| 5,639,650 A | 6/1997 | Johnston et al. |
| 5,643,576 A | 7/1997 | Johnston et al. |
| 5,703,057 A | 12/1997 | Johnston et al. |
| 5,726,022 A | 3/1998 | Burmer |
| 5,739,026 A | 4/1998 | Garoff et al. |
| 5,766,602 A | 6/1998 | Xiong et al. |
| 5,789,245 A | 8/1998 | Dubensky, Jr. et al. |
| 5,792,462 A | 8/1998 | Johnston et al. |
| 5,811,407 A | 9/1998 | Johnston et al. |
| 5,814,482 A | 9/1998 | Dubensky, Jr. et al. |
| 5,827,658 A | 10/1998 | Liang et al. |
| 5,831,016 A | 11/1998 | Wang et al. |
| 5,843,723 A | 12/1998 | Dubensky, Jr. et al. |
| 5,853,719 A | 12/1998 | Nair et al. |
| 5,958,738 A | 9/1999 | Lindemann et al. |
| 5,989,553 A | 11/1999 | Johnston et al. |
| 6,008,035 A | 12/1999 | Johnston et al. |
| 6,015,686 A | 1/2000 | Dubensky, Jr. et al. |
| 6,015,694 A | 1/2000 | Dubensky, Jr. et al. |
| 6,146,874 A | 11/2000 | Zolotukhin et al. |
| 6,156,558 A | 12/2000 | Johnston et al. |
| 6,190,666 B1 | 2/2001 | Garoff et al. |
| 6,194,191 B1 | 2/2001 | Zhang et al. |
| 6,197,502 B1 | 3/2001 | Renner et al. |
| 6,224,879 B1 | 5/2001 | Sjöberg et al. |
| 6,242,259 B1 | 6/2001 | Polo et al. |
| 6,261,570 B1 | 7/2001 | Parker et al. |
| 6,267,967 B1 | 7/2001 | Johnston et al. |
| 6,306,388 B1 | 10/2001 | Nair et al. |
| 6,329,201 B1 | 12/2001 | Polo et al. |
| 6,342,226 B1 | 1/2002 | Betbeder et al. |
| 6,342,372 B1 | 1/2002 | Dubensky, Jr. et al. |
| 6,376,236 B1 | 4/2002 | Dubensky, Jr. et al. |
| 6,391,632 B1 | 5/2002 | Dubensky, Jr. et al. |
| 6,426,196 B1 | 7/2002 | Dubensky, Jr. et al. |
| 6,448,389 B1 | 9/2002 | Gonczol et al. |
| 6,485,958 B2 | 11/2002 | Blanche et al. |
| 6,495,143 B2 | 12/2002 | Lee et al. |
| 6,521,235 B2 | 2/2003 | Johnston et al. |
| 6,531,135 B1 | 3/2003 | Johnston et al. |
| 6,541,010 B1 | 4/2003 | Johnston et al. |

(Continued)

FOREIGN PATENT DOCUMENTS

| | | |
|---|---|---|
| WO | WO 92/10578 A1 | 6/1992 |
| WO | WO 95/07994 A2 | 3/1995 |

(Continued)

OTHER PUBLICATIONS

International Search Report and Written Opinion for corresponding International Application No. PCT/US08/07701, mailed Dec. 18, 2008 (9 pages).
International Preliminary Report on Patentability for corresponding International Application No. PCT/US08/07701, mailed Sep. 2, 2009 (7 pages).
Supplementary European Search Report for European Application No. 08825920.5, mailed Mar. 15, 2011 (7 pages).
Kamrud et al, "Development and Characterization of Promoterless Helper RNAs for the Production of Alphavirus Replicon Particle" *Journal of General Virology* 91:1723-1727 (2010).
Volkova et al. "IRES-Dependent Replication of Venezuelan Equine Encephalitis Virus Makes it Highly Attenuated and Incapable of Replicating in Mosquito Cells" *Virology* 377:160-169 (2008).

(Continued)

*Primary Examiner* — Jim Ketter
(74) *Attorney, Agent, or Firm* — Myers Bigel Sibley & Sajovec, P.A.

(57) ABSTRACT

The present invention provides an isolated RNA molecule comprising: a) an alphavirus 5' replication recognition sequence, wherein at least one initiation codon has been removed from the 5' replication recognition sequence; b) a nucleotide sequence encoding an alphavirus structural protein; and c) an alphavirus 3' replication recognition sequence, with the proviso that the RNA molecule does not contain a promoter that directs transcription of the nucleotide sequence of (b), and wherein the alphavirus 5' and 3' replication recognition sequences of (a) and (c) direct replication of the RNA molecule in the presence of alphavirus non-structural proteins.

6 Claims, 7 Drawing Sheets

U.S. PATENT DOCUMENTS

| | | | |
|---|---|---|---|
| 6,583,121 | B1 | 6/2003 | Johnston et al. |
| 6,767,699 | B2 | 7/2004 | Polo et al. |
| 6,770,283 | B1 | 8/2004 | Garoff et al. |
| 6,783,939 | B2 | 8/2004 | Olmsted et al. |
| 6,844,188 | B1 | 1/2005 | MacDonald et al. |
| 7,045,335 | B2 | 5/2006 | Smith et al. |
| 7,267,823 | B2 | 9/2007 | Hart et al. |
| 7,419,674 | B2 | 9/2008 | Chulay et al. |
| 7,442,381 | B2 | 10/2008 | Smith et al. |
| 2001/0016199 | A1 | 8/2001 | Johnston et al. |
| 2002/0018766 | A1 | 2/2002 | Roberts et al. |
| 2002/0034521 | A1 | 3/2002 | Lee et al. |
| 2002/0102273 | A1 | 8/2002 | Grieve et al. |
| 2002/0141975 | A1 | 10/2002 | Olmsted et al. |
| 2002/0156251 | A1 | 10/2002 | Prieur et al. |
| 2002/0164582 | A1 | 11/2002 | Hart et al. |
| 2003/0021766 | A1 | 1/2003 | Vajdy et al. |
| 2003/0091591 | A1 | 5/2003 | Xiong et al. |
| 2003/0096397 | A1 | 5/2003 | Schlesinger et al. |
| 2003/0119182 | A1 | 6/2003 | Smith et al. |
| 2003/0120060 | A1 | 6/2003 | Gonczol et al. |
| 2003/0148262 | A1 | 8/2003 | Polo et al. |
| 2003/0152590 | A1 | 8/2003 | Hevey et al. |
| 2003/0232036 | A1 | 12/2003 | Johnston et al. |
| 2003/0232324 | A1 | 12/2003 | Polo et al. |
| 2004/0008458 | A1 | 1/2004 | Kase et al. |
| 2004/0009183 | A1 | 1/2004 | Lee et al. |
| 2004/0009945 | A1 | 1/2004 | Lee et al. |
| 2004/0029279 | A1 | 2/2004 | Kovacs et al. |
| 2004/0030117 | A1 | 2/2004 | Johnston et al. |
| 2004/0055037 | A1 | 3/2004 | Gleba et al. |
| 2004/0088764 | A1 | 5/2004 | Gleba et al. |
| 2004/0121466 | A1 | 6/2004 | Johnston et al. |
| 2004/0146859 | A1 | 7/2004 | Hart et al. |
| 2004/0166573 | A1 | 8/2004 | Smith et al. |
| 2004/0208848 | A1 | 10/2004 | Smith et al. |
| 2004/0255347 | A1 | 12/2004 | Klimyuk et al. |
| 2005/0014150 | A1 | 1/2005 | Atabekov et al. |
| 2005/0031592 | A1 | 2/2005 | Doolan et al. |
| 2005/0054107 | A1 | 3/2005 | Chulay et al. |
| 2005/0059004 | A1 | 3/2005 | Atabekov et al. |
| 2005/0118251 | A1 | 6/2005 | Nagata et al. |
| 2005/0123555 | A1 | 6/2005 | Olmsted et al. |
| 2006/0177819 | A1 | 8/2006 | Smith et al. |
| 2007/0065412 | A1 | 3/2007 | Chen et al. |
| 2008/0279891 | A1 | 11/2008 | Johnston et al. |
| 2009/0075384 | A1 | 3/2009 | Kamrud et al. |

FOREIGN PATENT DOCUMENTS

| | | |
|---|---|---|
| WO | WO 95/27044 A1 | 10/1995 |
| WO | WO 95/31565 A1 | 11/1995 |
| WO | WO 96/17072 A2 | 6/1996 |
| WO | WO 96/37220 A1 | 11/1996 |
| WO | WO 96/37616 A1 | 11/1996 |
| WO | WO 99/07834 A1 | 2/1999 |
| WO | WO 99/08706 A1 | 2/1999 |
| WO | WO 99/51263 A2 | 10/1999 |
| WO | WO 00/39302 A2 | 7/2000 |
| WO | WO 00/39318 A1 | 7/2000 |
| WO | WO 00/61772 A2 | 10/2000 |
| WO | WO 01/16343 A1 | 3/2001 |
| WO | WO 02/03917 A2 | 1/2002 |
| WO | WO 02/04493 A2 | 1/2002 |
| WO | WO 02/10578 A1 | 2/2002 |
| WO | WO 02/20721 A2 | 3/2002 |
| WO | WO 03/023026 A1 | 3/2003 |
| WO | WO 03/083065 A2 | 10/2003 |
| WO | WO 2004/055166 A2 | 7/2004 |
| WO | WO 2004/055167 A2 | 7/2004 |
| WO | WO 2004/085660 A2 | 10/2004 |
| WO | WO 2005/007689 A1 | 1/2005 |
| WO | WO 2006/085983 A2 | 8/2006 |
| WO | WO 2009/131604 | 10/2009 |

OTHER PUBLICATIONS

Adler et al. "A Canarypox Vector Expressing Cytomegalovirus (CMV) Glycoprotein B Primes for Antibody Responses to a Live Attenuated CMV Vaccine (Towne)" *The Journal of Infectious Diseases* 180:843-846 (1999).

Armas et al. "DNA Immunization Confers Protection Against Murine Cytomegalovirus Infection" *Journal of Virology* 70(11):7921-7928 (1996).

Balasuriya et al. "Alphavirus Replicon Particles Expressing the Two Major Envelope Proteins of Equine Arteritis Virus Induce High Level Protection Against Challenge with Virulent Virus in Vaccinated Horses" *Vaccine* 20:1609-1617 (2002).

Baric et al. "Expression and Self-Assembly of Norwalk Virus Capsid Protein from Venezuelan Equine Encephalitis Virus Replicons" *Journal of Virology* 76(6):3023-3030 (2002).

Barouch et al. "Augmentation of Immune Responses to HIV-1 and Simian Immunodeficiency Virus DNA Vaccines by IL-2/Ig Plasmid Administration in Rhesus Monkeys" *PNAS* 97(8):4192-4197 (2000).

Barry et al. "Expression Library Immunization to Discover and Improve Vaccine Antigens" *Immunological Reviews* 199:68-83 (2004).

Bell et al. "Effect of Low-NaCl Medium on the Envelope Glycoproteins of Sindbis Virus" *Journal of Virology* 25(3):764-769 (1978).

Berencsi et al. "A Canarypox Vector-Expressing Cytomegalovirus (CMV) Phosphoprotein 65 Induces Long-Lasting Cytotoxic T Cell Responses in Human CMV-Seronegative Subjects" *The Journal of Infectious Diseases* 183:1171-1179 (2001).

Berencsi et al. "Murine Cytotoxic T Cell Response Specific for Human Cytomegalovirus Glycoprotein B (gB) Induced by Adenovirus and Vaccinia Recombinants Expressing gB" *Journal of General Virology* 74:2507-2512 (1993).

Berglund et al. "Semliki Forest Virus Expression System: Production of Conditionally Infectious Recombinant Particles" *Bio/Technology* 11:916-920 (1993).

Bergman et al. "Long-Term Survival of Dogs with Advanced Malignant Melanoma After DNA Vaccination with Xenogeneic Human Tyrosinase: A Phase I Trial" *Clinical Cancer Research* 9:1284-1290 (2003).

Bernard et al. "Mutations in the E2 Glycoprotein of Venezuelan Equine Encephalitis Virus Confer Heparan Sulfate Interaction, Low Morbidity, and Rapid Clearance from Blood in Mice" *Virology* 276:93-103 (2000).

Betts et al. "Cross-Clade Human Immunodeficiency Virus (HIV)-Specific Cytotoxic T-Lymphocyte Responses in HIV-Infected Zambians" *J Virol* 71(11):8908-8911 (1997).

Bourne et al. "Preconception Immunization with a Cytomegalovirus (CMV) Glycoprotein Vaccine Improves Pregnancy Outcome in a Guinea Pig Model of Congenital CMV Infection" *The Journal of Infectious Diseases* 183:59-64 (2001).

Bredenbeek et al. "Sindbis Virus Expression Vectors: Packaging of RNA Replicons by Using Defective Helper RNAs" *Journal of Virology* 67(11):6439-6446 (1993).

Britt et al. "Formulation of an Immunogenic Human Cytomegalovirus Vaccine: Responses in Mice" *The Journal of Infectious Diseases* 171:18-25 (1995).

Caley et al. "Humoral, Mucosal, and Cellular Immunity in Response to a Human Immunodeficiency Virus Type 1 Immunogen Expressed by a Venezuelan Equine Encephalitis Virus Vaccine Vector" *J Virol* 71(4):3031-3038 (1997).

Caley et al. "Venezuelan Equine Encephalitis Virus Vectors Expressing HIV-1 Proteins: Vector Design Strategies for Improved Vaccine Efficacy" *Vaccine* 17:3124-3135 (1999).

Caltenco-Serrano et al. "Cytomegalovirus Infection in Patients with Solid-Organ Transplant" *Revista Latinameriana de Microbiologia* 43(4):177-182 (2001).

Carlson et al. "Expression, Purification and Characterization of a Soluble Form of Human Cytomegalovirus Glycoprotein B" *Virology* 239:198-205 (1997).

Casimiro et al. "Vaccine-Induced Immune Responses in Rodents and Nonhuman Primates by Use of a Humanized Human Immunodeficiency Virus Type 1 *pol* Gene" *Journal of Virology* 76(1):185-194 (2002).

Chappell et al. "A 9-nt Segment of a Cellular mRNA can Function as an Internal Ribosome Entry Site (IRES) and When Present in Linked Multiple Copies Greatly Enhances IRES Activity" *PNAS* 97(4):1536-1541 (2000).

Chatterjee et al. "Modification of Maternal and Congenital Cytomegalovirus Infection by Anti-Glycoprotein B Antibody Transfer in Guinea Pigs" *The Journal of Infectious Diseases* 183:1547-1553 (2001).

Corsini et al. "Efficiency of Transduction by Recombinant Sindbis Replicon Virus Varies Among Cell Lines, Including Mosquito Cells and Rat Sensory Neurons" *BioTechniques* 21:492-497 (1996).

Cutler and Garoff. "Mutants of the Membrane-Binding Region of Semliki Forest Virus E2 Protein. I. Cell Surface Transport and Fusogenic Activity" *The Journal of Cell Biology* 102:889-901 (1986).

Davis et al. "Alphavirus Replicon Particles as Candidate HIV Vaccines" *IUBMB Life* 53:209-211 (2002).

Davis et al. "Attenuated Mutants of Venezuelan Equine Encephalitis Virus Containing Lethal Mutations in the PE2 Cleavage Signal Combined with a Second-Site Suppressor Mutation in E1" *Virology* 212:102-110 (1995).

Davis et al. "Attenuating Mutations in the E2 Glycoprotein Gene of Venezuelan Equine Encephalitis Virus: Construction of Single and Multiple Mutants in a Full-Length cDNA Clone" *Virology* 183:20-31 (1991).

Davis et al. "A Genetically Engineered Live Virus Vaccine for Venezuelan Equine Encephalitis" *J Cell Biochemistry Supplement* O, No. 17, Part D, Abstract N404 (1993).

Davis et al. "Immunization Against Influenza with Attenuated Venezuelan Equine Encephalitis Virus Vectors" in *Options for the Control of Influenza III.*, L.E. Brown, A.W. Hampson and R.G. Webster, eds. Elsevier, Amsterdam, pp. 803-809 (1996).

Davis et al. "In Vitro Synthesis of Infectious Venezuelan Equine Encephalitis Virus RNA from a cDNA Clone: Analysis of a Viable Deletion Mutant" *Virology* 171:189-204 (1989).

Davis et al. "In Vitro Synthesis of Infectious Venezuelan Equine Encephalitis Virus RNA from a cDNA Clone: Analysis of a Viable Deletion Mutant and Mutations Affecting Virulence" *Vaccines* 90:109-113 (1990).

Davis et al. "A Molecular Genetic Approach to the Study of Venezuelan Equine Encephalitis Virus Pathogenesis" *Archives of Virology* 9:99-109 (1994).

Davis et al. "A Single Nucleotide Change in the E2 Glycoprotein Gene of Sindbis Virus Affects Penetration Rate in Cell Culture and Virulence in Neonatal Mice" *PNAS USA* 83:6771-6775 (1986).

Davis et al. "A Viral Vaccine Vector That Expresses Foreign Genes in Lymph Nodes and Protects Against Mucosal Challenge" *Journal of Virology* 70(6):3781-3787 (1996).

Davis et al. "Vaccination of Macaques Against Pathogenic Simian Immunodeficiency Virus with Venezuelan Equine Encephalitis Virus Replicon Particles" *J Virol* 74(1): 371-378 (2000).

Dubensky et al. "Sindbis Virus DNA-Based Expression Vectors: Utility for in Vitro and in Vivo Gene Transfer" *Journal of Virology* 70(1):508-519 (1996).

Dubuisson and Rice. "Sindbis Virus Attachment: Isolation and Characterization of Mutants with Impaired Binding to Vertebrate Cells" *Journal of Virology* 67(6):3363-3374 (1993).

Eiben et al. "Establishment of an HLA-A*0201 Human Papillomavirus Type 16 Tumor Model to Determine the Efficacy of Vaccination Strategies in HLA-A*0201 Transgenic Mice[1]" *Cancer Research* 62:5792-5799 (2002).

Elkington et al. "Ex Vivo Profiling of CD8$^+$-T-Cell Responses to Human Cytomegalovirus Reveals Broad and Multispecific Reactivities in Healthy Virus Carriers" *Journal of Virology* 77(9):5226-5240 (2003).

Endresz et al. "Induction of Human Cytomegalovirus (HCMV)-Glycoprotein B (gB)-Specific Neutralizing Antibody and Phosphorprotein 65 (pp65)-Specific Cytotoxic T Lymphocyte Responses by Naked DNA Immunization" *Vaccine* 17:50-58 (1999).

Erlap et al. "Doxorubicin and Paclitaxel Enhance the Antitumor Efficacy of Vaccines Directed Against HER 2/neu in a Murine Mammary Carcinoma Model" *Breast Cancer Research* 6:R275-R283 (2004).

Favre et al. "Semliki Forest Virus Capsid Protein Expressed by a Baculovirus Recombinant" *Archives of Virology* 132:307-319 (1993).

Feyzi et al. "Structural Requirement of Heparan Sulfate for Interaction with Herpes Simplex Viurs Type 1 Virions and Isolated Glycoprotein C*" *The Journal of Biological Chemistry* 272(40):24850-24857 (1997).

Frey et al. "Effects of Antigen Dose and Immunization Regimens on Antibody Responses to a Cytomegalovirus Glycoprotein B Subunit Vaccine" *The Journal of Infectious Diseases* 180:1700-1703 (1999).

Frolov et al. "Alphavirus-Based Expression Vectors: Strategies and Applications" *PNAS USA* 93:11371-11377 (1996).

Garoff et al. "Expression of Semliki Forest Virus Proteins from Cloned Complementary DNA. II. The Membrane-Spanning Glycoprotein E2 is Transported to the Cell Surface Without its Normal Cytoplasmic Domain" *The Journal of Cell Biology* 97:652-658 (1983).

Geigenmüller-Gnirke et al. "Complementation Between Sindbis Viral RNAs Produces Infectious Particles with a Bipartite Genome" *PNAS USA* 88:3253-3257 (1991).

Geisbert et al. "Evaluation in Nonhuman Primates of Vaccines Against Ebola Virus" *Emerging Infectious Diseases* 8(5):503-507 (2002).

Geysen et al. "A Priori Delineation of a Peptide which Mimics a Discontinuous Antigenic Determinant" *Molecular Immunology* 23(7):709-715 (1986).

Geysen et al. "Use of a Peptide Synthesis to Probe Viral Antigens for Epitopes to a Resolution of a Single Amino Acid" *PNAS USA* 81(13):3998-4002 (1984).

Gidwitz et al. "Differences in Virion Stability Among Sindbis Virus Pathogenesis Mutants*" *Virus Research* 10:225-240 (1988).

Gingras et al. "Activation of the Translational Suppressor 4E-BP1 Following Infection with Encephalomyocarditis Virus and Poliovirus" *PNAS USA* 93:5578-5583 (1996).

Golzio et al. "Cell Synchronization Effect on Mammalian Cell Permeabilization and Gene Delivery by Electric Field" *Biochimica et Biophysica Acta* 1563:23-28 (2002).

Gönczöl and Plotkin. "Development of a Cytomegalovirus Vaccine: Lessons from Recent Clinical Trials" *Exp Opin Biol Ther* 1(3):401-412 (2001).

Gönczöl et al. "Preclinical Evaluation of an ALVAC (Canarypox)-Human Cytomegalovirus Glycoprotein B Vaccine Candidate" *Vaccine* 13(12):1080-1085 (1995).

Gradi et al. "Proteolysis of Human Eukaryotic Translation Initiation Factor eIF4GII, but Not eIF4GI, Coincides with the Shutoff of Host Protein Synthesis After Poliovirus Infection" *PNAS USA* 95:11089-11094 (1998).

Grieder et al. "Specific Restrictions in the Progression of Venezuelan Equine Encephalitis Virus-Induced Disease Resulting from Single Amino Acid Changes in the Glycoproteins" *Virology* 206:994-1006 (1995).

Gyulai et al. "Cytotoxic T Lymphocyte (CTL) Responses to Human Cytomegalovirus pp65, IE1-Exon4, gB, pp150, and pp28 in Healthy Individuals: Reevaluation of Prevalence of IE1-Specific CTLs" *The Journal of Infectious Diseases* 181:1537-1546 (2000).

Hahn et al. "Infectious Sindbis Virus Transient Expression Vectors for Studying Antigen Processing and Presentation" *PNAS USA* 89:2679-2683 (1992).

Hariharan et al. "DNA Immunization Against Herpes Simplex Virus: Enhanced Efficacy Using a Sindbis Virus-Based Vector" *Journal of Virology* 72(2):950-958 (1998).

Heidner et al. "Lethality of PE2 Incorporation into Sindbis Virus can be Suppressed by Second-Site Mutations in E3 and E2" *Journal of Virology* 68(4):2683-2692 (1994).

Heise et al. "An Attenuating Mutation in nsP1 of the Sindbis-Group Virus S.A.AR86 Accelerates Nonstructural Protein Processing and Up-Regulates Viral 26S RNA Synthesis" *Journal of Virology* 77(2):1149-1156 (2003).

Heiser et al. "Autologous Dendritic Cells Transfected with Prostate-Specific Antigen RNA Stimulate CTL Responses Against Metastatic Prostate Tumors" *The Journal of Clinical Investigation* 109(3):409-417 (2002).

Herweijer and Wolff. "Self-Amplifying Vectors for Gene Delivery" *Advanced Drug Delivery Reviews* 27:5-16 (1997).
Hevey et al. "Marburg Virus Vaccines Based Upon Alphavirus Replicons Protect Guinea Pigs and Nonhuman Primates" *Virology* 251:28-37 (1998).
Hevey et al. "Marburg Virus Vaccines: Comparing Classical and New Approaches" *Vaccine* 20:586-593 (2002).
Hill et al. "RNA-RNA Recombination in Sindbis Virus: Roles of the 3' Conserved Motif, Poly(A) Tail, and Nonviral Sequences of Template RNAs in Polymerase Recognition and Template Switching" *Journal of Virology* 71(4):2693-2704 (1997).
Hirsch et al. "Patterns of Viral Replication Correlate with Outcome in Simian Immunodeficiency Virus (SIV)-Infected Macaques: Effect of Prior Immunization with a Trivalent SIV Vaccine in Modified Vaccina Virus Ankara" *J Virol* 70(6):3741-3752 (1996).
Hodgson et al. "Expression of Venezuelan Equine Encephalitis Virus Proteins by Recombinant Baculoviruses" *The American Journal of Tropical Medicine and Hygiene* 49:195-196 (Abstract) (1993).
Holcik and Korneluk. "Functional Characterization of the X-Linked Inhibitor of Apoptosis (XIAP) Internal Ribosome Entry Site Element: Role of La Autoantigen in XIAP Translation" *Molecular and Cellular Biology* 20(13):4648-4657 (2000).
Holcik et al. "A New Internal-Ribosome-Entry-Site Motif Potentiates XIAP-Mediated Cytoprotection" *Nature Cell Biology* 1:190-192 (1999).
Holcik et al. "The Internal Ribosome Entry Site-Mediated Translation of Antiapoptotic Protein XIAP is Modulated by the Heterogeneous Nuclear Ribonucleoproteins C1 and C2" *Molecular and Cellular Biology* 23(1):280-288 (2003).
International Search Report for International Application Serial No. PCT/US02/28610, mailed Feb. 11, 2003 (4 pages).
International Search Report for International Application Serial No. PCT/US03/39723, mailed Aug. 17, 2004 (1 page).
International Search Report for International Application Serial No. PCT/US03/39725, mailed Dec. 3, 2004 (3 pages).
International Search Report for International Application Serial No. PCT/US04/008458, mailed Oct. 25, 2004 (10 pages).
International Search Report for International Application Serial No. PCT/US04/021772, mailed Dec. 28, 2004 (18 pages).
Jalanko. "Expression of Semliki Forest Virus Capsid Protein from SV40 Recombinant Virus" *FEBS Letters* 186(1):59-64 (1985).
Jang and Wimmer. "Cap-Independent Translation of Encephalomyocarditis Virus RNA: Structural Elements of the Internal Ribosomal Entry Site and Involvement of a Cellular 57-kD RNA-Binding Protein" *Genes & Development* 4:1560-1572 (1990).
Joachims et al. "Cleavage of Poly(A)-Binding Protein by Enterovirus Proteases Concurrent with Inhibition of Translation in Vitro" *Journal of Virology* 73(1):718-727 (1999).
Johnston and Peters. "Alphaviruses" in *Fields Virology*, 3$^{rd}$ ed., Lippincott-Raven Publishers, Philadelphia, Chapter 28, pp. 843-898 (1996).
Johnston and Smith. "Selection for Accelerated Penetration in Cell Culture Coselects for Attenuated Mutants of Venezuelan Equine Encephalitis Virus[1]" *Virology* 162:437-443 (1988).
Johnston et al. "Studies of Alphavirus Virulence Using Full-Length Clones of Sindbis and Venezuelan Equine Encephalitis Viruses" in *New Aspects of Positive Strand RNA Viruses*, M.A. Brinton et al. (eds.), ASM Press, Chapter 49, pp. 334-339 (1990).
Kamrud et al. "Alphavirus Replicon Approach to Promoterless Analysis of IRES Elements" *Virology* 360:376-387 (2007).
Kaufman et al. "Improved Vectors for Stable Expression of Foreign Genes in Mammalian Cells by use of the Untranslated Leader Sequence from EMC Virus" *Nucleic Acids Research* 19(16):4485-4490 (1991).
Kern et al. "Cytomegalovirus (CMV) Phosphoprotein 65 Makes a Large Contribution to Shaping the T Cell Repertoire in CMV-Exposed Individuals" *The Journal of Infectious Diseases* 185:1709-1716 (2002).
Khromykh. "Replicon-Based Vectors of Positive Strand RNA Viruses" *Current Opinion in Molecular Therapeutics* 2(5):555-569 (2000).
Kinney et al. "Attenuation of Venezuelan Equine Encephalitis Virus Strain TC-83 is Encoded by the 5'-Noncoding Region and the E2 Envelope Glycoprotein" *Journal of Virology* 67(3):1269-1277 (1993).
Kinney et al. "The Full-Length Nucleotide Sequences of the Virulent Trinidad Donkey Strain of Venezuelan Equine Encephalitis Virus and its Attenuated Vaccine Derivative, Strain TC-83" *Virology* 170:19-30 (1989).
Klimstra et al. "Adaptation of Sindbis Virus to BHK Cells Selects for Use of Heparan Sulfate as an Attachment Receptor" *Journal of Virology* 72(9):7357-7366 (1998).
Knight. "Secretion from Bovine Chromaffin Cells Acutely Expressing Exogenous Proteins Using a Recombinant Semliki Forest Virus Containing an EGFP Reporter" *Molecular and Cellular Neuroscience* 14:486-505 (1999).
Kohl et al. "Transient Gene Expression in Mammalian and Mosquito Cells Using a Recombinant Semliki Forest Virus Expressing T7 RNA Polymerase" *Applied Microbiology and Biotechnology* 53:51-56 (1999).
Koller et al. "A High-Throughput Alphavirus-Based Expression Cloning System for Mammalian Cells" *Nature Biotech* 19:851-855 (2001).
Kondor-Koch et al. "Expression of Semliki Forest Virus Proteins from Cloned Complementary DNA. I. The Fusion Activity of the Spike Glycoprotein" *The Journal of Cell Biology* 97:644-651 (1983).
Kumamoto et al. "Induction of Tumor-Specific Protective Immunity by in situ Langerhans Cell Vaccine" *Nature Biotechnology* 20:64-69 (2002).
Lee et al. "Candidate Vaccine Against Botulinum Neurotoxin Serotype A Derived from a Venezuelan Equine Encephalitis Virus Vector System" *Infection and Immunity* 69(9):5709-5715 (2001).
Lee et al. "Efficient Long-Term Coexpression of a Hammerhead Ribozyme Targeted to the U5 Region of HIV-1 LTR by Linkage to the Multidrug-Resistance Gene" *Antisense & Nucleic Acid Drug Development* 7:511-522 (1997).
Lee et al. "Immune Protection Against Staphylococcal Enterotoxin-Induced Toxic Shock by Vaccination with a Venezuelan Equine Encephalitis Virus Replicon" *The Journal of Infectious Diseases* 185:1192-1196 (2002).
Leitner et al. "Enhancement of Tumor-Specific Immune Response with Plasmid DNA Replicon Vectors" *Cancer Research* 60:51-55 (2000).
Lemm and Rice. "Assembly of Functional Sindbis Virus RNA Replication Complexes: Requirement for Coexpression of P123 and P34" *Journal of Virology* 67(4):1905-1915 (1993).
Lemm et al. "Polypeptide Requirements for Assembly of Functional Sindbis Virus Replication Complexes: a Model for the Temporal Regulation of Minus- and Plus-Strand RNA Synthesis" *The EMBO Journal* 13(12):2925-2934 (1994).
Leone et al. "In Vitro Synthesis of the Gene Coding for the Glycoprotein E1 of Sindbis Virus" *Microbiologica* 8(2):123-130 (1985) (Abstract Only).
Li and Garoff. "Production of Infectious Recombinant Moloney Murine Leukemia Virus Particles in BHK Cells Using Semliki Forest Virus-Derived RNA Expression Vectors" *PNAS USA* 93:11658-11663 (1996).
Liljeström. "Alphavirus Expression Systems" *Current Opinion in Biotechnology* 5:495-500 (1994).
Liljeström and Garoff. "A New Generation of Animal Cell Expression Vectors Based on the Semliki Forest Virus Replicon" *Bio/Technology* 9:1356-1361 (1991).
Liljeström et al. "In Vitro Mutagenesis of a Full-Length cDNA Clone of Semliki Forest Virus: the Small 6,000-Molecular-Weight Membrane Protein Modulates Virus Release" *Journal of Virology* 65(8):4107-4113 (1991).
Lobigs and Garoff. "Fusion Function of the Semliki Forest Virus Spike is Activated by Proteolytic Cleavage of the Envelope Glycoprotein Precursor p62" *Journal of Virology* 64(3):1233-1240 (1990).
Lu and Silver. "Transmission of Replication-Defective Sindbis Helper Vectors Encoding Capsid and Envelope Proteins" *Journal of Virological Methods* 91:59-65 (2001).

Lundström. "Alphavirus Vectors: Applications for DNA Vaccine Production and Gene Expression" *Intervirology* 43:247-257 (2000).

Lundström et al. "Secretion of Semliki Forest Virus Membrane Glycoprotein E1 From *Bacillus subtilis*" *Virus Research* 2:69-83 (1985).

MacDonald and Johnston. "Role of Dendritic Cell Targeting in Venezuelan Equine Encephalitis Virus Pathogenesis" *Journal of Virology* 74(2):914-922 (2000).

Maecker et al. "Use of Overlapping Peptide Mixtures as Antigens for Cytokine Flow Cytometry" *Journal of Immunological Methods* 255:27-40 (2001).

Marshall et al. "An Adenovirus Recombinant that Expresses the Human Cytomegalovirus Major Envelope Glycoprotein and Induces Neutralizing Antibodies" *The Journal of Infectious Diseases* 162:1177-1181 (1990).

Martinez-Salas et al. "Functional Interactions in Internal Translation Initiation Directed by Viral and Cellular IRES Elements" *Journal of General Virology* 82:973-984 (2001).

McCue and Anders. "Soluble Expression and Complex Formation of Proteins Required for HCMV DNA Replication Using the SFV Expression System" *Protein Expression and Purification* 13:301-312 (1998).

McKnight et al. "Deducted Consensus Sequence of Sindbis Virus Strain AR339: Mutations Contained in Laboratory Strains Which Affect Cell Culture and in Vivo Phenotypes" *Journal of Virology* 70(3):1981-1989 (1996).

Melancon and Garoff. "Processing of the Semliki Forest Virus Structural Polyprotein: Role of the Capsid Protease" *Journal of Virology* 61(5):1301-1309 (1987).

Melancon and Garoff. "Reinitiation of Translocation in the Semliki Forest Virus Structural Polyprotein: Identification of the Signal for the E1 Glycoprotein" *The EMBO Journal* 5(7):1551-1560 (1986).

Morello et al. "Suppression of Murine Cytomegalovirus (MCMV) Replication with a DNA Vaccine Encoding MCMV M84 (a Homolog of Human Cytomegalovirus pp65)" *Journal of Virology* 74(8):3696-3708 (2000).

Morenstern and Land. "Advanced Mammalian Gene Transfer: High Titre Retroviral Vectors with Multiple Drug Selection Markers and a Complementary Helper-Free Packaging Cell Line" *Nucleic Acids Research* 18(12):3587-3596 (1990).

Nelson et al. "Venezuelan Equine Encephalitis Replicon Immunization Overcomes Intrinsic Tolerance and Elicits Effective Anti-Tumor Immunity to the 'Self' Tumor-Associated Antigen, *neu* in a Rat Mammary Tumor Model" *Breast Cancer Research and Treatment* 82:169-183 (2003).

Non-Final Office Action issued in U.S. Appl. No. 12/143,320 on Apr. 29, 2010 (8 pages).

Oker-Blom and Summers. "Expression of Sindbis Virus 26S cDNA in *Spodoptera frugiperda* (Sf9) Cells, Using a Baculovirus Expression Vector" *Journal of Virology* 63(3):1256-1264 (1989).

Olmsted et al. "Characterization of Sindbis Virus Epitopes Important for Penetration in Cell Culture and Pathogenesis in Animals[1]" *Virology* 148:245-254 (1986).

Olmsted et al. "Sindbis Virus Mutants Selected for Rapid Growth in Cell Culture Display Attenuated Virulence in Animals" *Science* 225(4660):424-427 (1984).

Orkin and Motulsky. "Report and Recommendations of the Panel to Assess the NIH Investment in Research on Gene Therapy" (42 pages)(1995).

Overwijk and Restifo, "Creating Therapeutic Cancer Vaccines: Notes from the Battlefield" *Trends in Immunology* 22(1):5-7 (2001).

Pardoll. "Cancer Vaccines" *Nature Medicine Vaccine Supplement* 4(5):525-531 (1998).

Pardoll. "Spinning Molecular Immunology into Successful Immunotherapy" *Nature Reviews—Immunology* 2:227-238 (2002).

Paredes et al. "Three-Dimensional Structure of a Membrane-Containing Virus" *PNAS USA* 90:9095-9099 (1993).

Pass and Burke. "Development of Cytomegalovirus Vaccines: Prospects for Prevention of Congenital CMV Infection" *Seminars in Pediatric Infectious Diseases* 13(3):196-204 (2002).

Pass et al. "A Subunit Cytomegalovirus Vaccine Based on Recombinant Envelope Glycoprotein B and a New Adjuvant" *The Journal of Infectious Diseases* 180:970-975 (1999).

Pedersen and Eddy. "Separation, Isolation, and Immunological Studies of the Structural Proteins of Venezuelan Equine Encephalomyelitis Virus" *J Virology* 14(4):740-744 (1974).

Plotkin et al. "Multicenter Trial of Towne Strain Attenuated Virus Vaccine in Seronegative Renal Transplant Recipients[1]" *Transplantation* 58(11):1176-1178 (1994).

Polo and Johnston. "Attenuating Mutations in Glycoproteins E1 and E2 of Sindbis Virus Produce a Highly Attenuated Stain when Combined in Vitro" *Journal of Virology* 64(9):4438-4444 (1990).

Polo and Johnston. "A Model for in Vitro Development of Live, Recombinant Alphavirus Vaccines" in *Vaccines 90: Modern Approaches to New Vaccines Including Prevention of AIDS*, Brown et al. (eds), Cold Spring Harbor Laboratory, pp. 105-108 (1990).

Polo and Johnston. "Mutational Analysis of Virulence Locus in the E2 Glycoprotein Gene of Sindbis Virus" *Journal of Virology* 65(11):6358-6361 (1991).

Polo et al. "Stable Alphavirus Packaging Cell Lines for Sindbis Virus- and Semliki Forest Virus-Derived Vectors" *PNAS USA* 96:4598-4603 (1999).

Presley et al. "Proteolytic Processing of the Sindbis Virus Membrane Protein Precursor PE2 is Nonessential for Grown in Vertebrate Cells but is Required for Efficient Growth in Invertebrate Cells" *Journal of Virology* 65(4):1905-1909 (1991).

Pugachev et al. "Development of a Rubella Virus Vaccine Expression Vector: Use of a Picornavirus Internal Ribosome Entry Site Increases Stability of Expression" *Journal of Virology* 74(22):10811-10815 (2000).

Pugachev et al. "Double-Subgenomic Sindbis Virus Recombinants Expressing Immunogenic Proteins of Japanese Encephalitis Virus Induce Significant Protection in Mice Against Lethal JEV Infection" *Virology* 212:587-594 (1995).

Pushko et al. "Individual and Bivalent Vaccines Based on Alphavirus Replicons Protect Guinea Pigs Against Infection with Lassa and Ebola Viruses" *Journal of Virology* 75(23):11677-11685 (2001).

Pushko et al. "Replicon-Helper Systems from Attenuated Venezuelan Equine Encephalitis Virus: Expression of Heterologous Genes in Vitro and Immunization Against Heterologous Pathogens in Vivo" *Virology* 239:389-401 (1997).

Ragupathi and Livingston. "The Case for Polyvalent Cancer Vaccines that Induce Antibodies" *Expert Rev Vaccines* 1(2):193-206 (2002).

Rayner et al. "Alphavirus Vectors and Vaccinations" *Reviews in Medical Virology* 12:279-296 (2002).

Rice et al. "Expression of Sindbis Virus Structural Proteins via Recombinant Vaccinia Virus: Synthesis, Processing, and Incorporation into Mature Sindbis Virions" *J Virology* 56(1):227-239 (1985).

Riedel. "Different Membrane Anchors Allow the Semliki Forest Virus Spike Subunit E2 to Reach the Cell Surface" *Journal of Virology* 54:224-228 (1985).

Roberts and Belsham. "Complementation of Defective Picornavirus Internal Ribosome Entry Site (IRES) Elements by the Coexpression of Fragments of the IRES" *Virology* 227:53-62 (1997).

Russell et al. "Sindbis Virus Mutations Which Coordinately Affect Glycoprotein Processing, Penetration, and Virulence in Mice" *Journal of Virology* 63(4):1619-1629 (1989).

Sadanaga et al. "Dendritic Cell Vaccination with MAGE Peptide is a Novel Therapeutic Approach for Gastrointestinal Carcinomas[1]" *Clinical Cancer Research* 7:2277-2284 (2001).

Salminen et al. "Membrane Fusion Process of Semliki Forest Virus II: Cleavage-Dependent Reorganization of the Spike Protein Complex Controls Virus Entry" *The Journal of Cell Biology* 116(2):349-357 (1992).

Schleiss. "Animal Models of Congenital Cytomegalovirus Infection: An Overview of Progress in the Characterization of Guinea Pig Cytomegalovirus (GPCMV)" *Journal of Clinical Virology* 25:S37-S49 (2002).

Schlesinger. "Alphaviruses—Vectors for the Expression of Heterologous Genes" *TiBTech* 11:18-22 (1993).

Schlesinger and Dubensky. "Alphavirus Vectors for Gene Expression and Vaccines" *Current Opinion in Biotechnology* 10:434-439 (1999).

Schlesinger and Schlesinger. "*Togaviridae*: The Viruses and Their Replication" in *Fields Virology*, 3rd ed. (Fields et al., eds.), Lipincott-Raven Publishers, Philadelphia, Chapter 27, pp. 825-841 (1996).

Schoepp and Johnston. "Directed Mutagenesis of a Sindbis Virus Pathogenesis Site" *Virology* 193:149-159 (1993).

Schultz-Cherry et al. "Influenza Virus (A/HK/156/97) Hemagglutinin Expressed by an Alphavirus Replicon System Protects Chickens Against Lethal Infection with Hong Kong-Origin H5N1 Viruses" *Virology* 278:55-59 (2000).

Shi et al. "Construction and Characterization of Subgenomic Replicons of New York Strain of West Nile Virus" *Virology* 296:219-233 (2002).

Simpson et al. "Complete Nucleotide Sequence and Full-Length cDNA Clone of S.A.AR86, a South African Alphavirus Related to Sindbis[1]" *Virology* 222:464-469 (1996).

Sjöberg et al. "A Significantly Improved Semliki Forest Virus Expression System Based on Translation Enhancer Segments from the Viral Capsid Gene" *Bio/Technology* 12:1127-1131 (1994).

Slepushkin et al. "Large-Scale Purification of a Lentiviral Vector by Size Exclusion Chromatography or Mustang Q Ion Exchange Capsule" *BioProcessing Journal*, Sep./Oct., pp. 89-95 (2003).

Smerdou and Liljeström. "Two-Helper RNA System for Production of Recombinant Semliki Forest Virus Particle" *Journal of Virology* 73(2):1092-1098 (1999).

Speckner et al. "Antigenic Domain 1 of Human Cytomegalovirus Glycoprotein B Induces a Multitude of Different Antibodies Which, when Combined, Results in Incomplete Virus Neutralization" *Journal of General Virology* 80:2183-2191 (1999).

Strauss and Strauss. "Alphavirus Proteinases" *Seminars in Virology* 1:347-356 (1990).

Strauss and Strauss. "The Alphaviruses: Gene Expression, Replication, and Evolution" *Microbiological Reviews* 58(3):491-562 (1994).

Suomalainen et al. "Spike Protein-Nucleocapsid Interactions Drive the Budding of Alphaviruses" *Journal of Virology* 66(8):4737-4747 (1992).

Sykes and Johnston. "Genetic Live Vaccines Mimic the Antigenicity but not Pathogenicity of Live Viruses" *DNA and Cell Biology* 18(7):521-531 (1999).

Technical Bulletin No. 166: "RiboMAX™ Large Scale RNA Production Systems—SP6 and T7" Promega Corporation, pp. 1-11 (Revised Sep. 1; http://www.promega.com/tbs/tb166.pdf on Nov. 4, 2004).

Temperton. "DNA Vaccines Against Cytomegalovirus: Current Progress" *International Journal of Antimicrobial Agents* 19:169-172 (2002).

Thompson and Sarnow. "Enterovirus 71 Contains a Type I IRES Element that Functions When Eukaryotic Initiation Factor eIF4G is Cleaved" *Virology* 315:259-266 (2003).

Tugizov et al. "Mutated Forms of Human Cytomegalovirus Glycoprotein B are Impaired in Inducing Syncytium Formation" *Virology* 209:580-591 (1995).

Ubol et al. "Neurovirulent Strains of *Alphavirus* Induce Apoptosis in bcl-2-Expressing Cells: Role of a Single Amino Acid Change in the E2 Glycoprotein" *PNAS USA* 91:5202-5206 (1994).

Van Der Velden et al. "Defective Point Mutations of the Encephalomyocarditis Virus Internal Ribosome Entry Site can be Complemented in Trans" *Virology* 214:82-90 (1995).

Vaz-Santiago et al. "Ex Vivo Stimulation and Expansion of Both CD4+ and CD8+ T Cells from Peripheral Blood Mononuclear Cells of Human Cytomegalovirus-Seropositive Blood Donors by Using a Soluble Recombinant Chimeric Protein, IE1-pp65" *Journal of Virology* 75(17):7840-7847 (2001).

Velders et al. "Eradication of Established Tumors by Vaccination with Venezuelan Equine Encephalitis Virus Replicon Particles Delivering Human Papillomavirus 16 E7 RNA[1]" *Cancer Research* 61:7861-7867 (2001).

Verma and Somia. "Gene Therapy—Promises, Problems and Prospects" *Nature* 389:239-242 (1997).

Waite et al. "Inhibition of Sindbis Virus Production by Media of Low Ionic Strength: Intracellular Events and Requirements for Reversal" *Journal of Virology* 5:60-71 (1970).

Walter et al. "Reconstitution of Cellular Immunity Against Cytomegalovirus in Recipients of Allogeneic Bone Marrow by Transfer T-Cell Clones from the Donor" *The New England Journal of Medicine* 333:1038-1044 (1995).

Wang et al. "Alphavirus Replicon Particles Containing the Gene for HER2/neu Inhibit Breast Cancer Growth and Tumorigenesis" *Breast Cancer Research* 7:R145-R155 (2005).

Wang et al. "Core Protein-Coding Sequence, but not Core Protein, Modulates the Efficiency of Cap-Independent Translation Directed by the Internal Ribosome Entry Site of Hepatitis C Virus" *Journal of Virology* 74(23):11347-11358 (2000).

Ward et al. "Immunotherapeutic Potential of Whole Tumor Cells" *Cancer Immunol Immunother* 51:351-357 (2002).

Weiss and Schlesinger. "Recombination Between Sindbis Virus RNAs" *Journal of Virology* 65(8):4017-4025 (1991).

Wen et al. "Expression of Genes Encoding Vesicular Stomatitis and Sindbis Virus Glycoproteins in Yeast Leads to Formation of Disulfide-Linked Oligomers" *Virology* 153:150-154 (1986).

Wen et al. "Tricistronic Viral Vectors Co-Expressing Interleukin-12 (IL-12) and CD80 (B7-1) for the Immunotherapy of Cancer: Preclinical Studies in Myeloma" *Cancer Gene Therapy* 8(5):361-370 (2001).

Williamson et al. "Characterization and Selection of HIV-1 Subtype C Isolates for Use in Vaccine Development" *AIDS Research and Human Retroviruses* 19(2):133-144 (2003).

Williamson et al. "Designing HIV-1 Subtype C Vaccines for South Africa" *South African Journal of Science* 96:318-324 (2000).

Wilson and Hart. "Protection from Ebola Virus Mediated by Cytotoxic T Lymphocytes Specific for the Viral Nucleoprotein" *Journal of Virology* 75(6):2660-2664 (2001).

Wilson et al. "Naturally Occurring Dicistronic Cricket Paralysis Virus RNA is Regulated by Two Internal Ribosome Entry Sites" *Molecular and Cellular Biology* 20(14):4990-4999 (2000).

Wilson et al. "Vaccine Potential of Ebola Virus VP24, VP30, VP35 and VP40 Proteins" *Virology* 286:384-390 (2001).

Xiong et al. "Sindbis Virus: An Efficient, Broad Host Range Vector for Gene Expression in Animal Cells" *Science* 243:1188-1191 (1989).

Yamanaka et al. "Enhancement of Antitumor Immune Response in Glioma Models in Mice by Genetically Modified Dendritic Cells Pulsed with Semliki Forest Virus-Mediated Complementary DNA" *J Neurosurg* 94:474-481 (2001).

Yamanaka et al. "Marked Enhancement of Antitumor Immune Responses in Mouse Brain Tumor Models by Genetically Modified Dendritic Cells Producing Semliki Forest Virus-Mediated Interleukin-12" *J Neurosurg* 97:611-618 (2002).

Yang and Sarnow. "Location of the Internal Ribosome Entry Site in the 5' Non-Coding Region of the Immunoglobulin Heavy-Chain Binding Protein (BiP) mRNA: Evidence for Specific RNA-Protein Interactions" *Nucleic Acids Research* 25(14):2800-2807 (1997).

Ying et al. "Cancer Therapy Using a Self-Replicating RNA Vaccine" *Nature Medicine* 5(7):823-827 (1999).

Zhao and Garoff. "Role of Cell Surface Spikes in Alphavirus Budding" *Journal of Virology* 66(12):7089-7095 (1992).

SEQUENCE LISTING

<160> NUMBER OF SEQ ID NOS: 106

<210> SEQ ID NO 1
<211> LENGTH: 521
<212> TYPE: DNA
<213> ORGANISM: Venezuelan equine encephalitis virus

<400> SEQUENCE: 1

```
atgggcggcg catgagagaa gcccagacca attacctacc caaaatggag aaagttcacg     60
ttgacatcga ggaagacagc ccattcctca gagctttgca gcggagcttc ccgcagtttg    120
aggtagaagc caagcaggtc actgataatg accatgctaa tgccagagcg ttttcgcatc    180
tggcttcaaa actgatcgaa acggaggtgg acccatccga cacgatcctt gacattggaa    240
gtgcgcccgc ccgcagaatg tattctaagc acaagtatca ttgtatctgt ccgatgagat    300
gtgcggaaga tccggacaga ttgtataagt atgcaactaa gctgaagaaa aactgtaagg    360
aaataactga taaggaattg gacaagaaaa tgaaggagct cgccgccgtc atgagcgacc    420
ctgacctgga aactgagact atgtgcctcc acgacgacga gtcgtgtcgc tacgaagggc    480
aagtcgctgt ttaccaggat gtatacgcgg ttgacggacc g                       521
```

<210> SEQ ID NO 2
<211> LENGTH: 499
<212> TYPE: DNA
<213> ORGANISM: Artificial
<220> FEATURE:
<223> OTHER INFORMATION: Synthetic noncoding recognition sequence

<400> SEQUENCE: 2

```
ataggcggcg catgagagaa gcccagacca attacctacc caaaatggag aaagttcacg     60
ttgacatcga ggaagacagc ccattcctca gagctttgca gcggagcttc ccgcagtttg    120
aggtagaagc caagcaggtc actgataatg accatgctaa tgccagagcg ttttcgcatc    180
```

```
tggcttcaaa actgatcgaa acggaggtgg acccatccga cacgatcctt gacattggaa    240
gtgcgcccgc ccgcagaatg tattctaagc acaagtatca ttgtatctgt ccatgagat     300 gtgcggaaga tccggacaga ttgtataagt atgcaactaa gctgaagaaa aactgtaagg    360
aaataactga taaggaattg dacaagaaaa tgaaggagct cgccgccgtc atgagcgacc    420
ctgacctgga aactgagact atgtgcctcc acgacgacga gtcgtgtcgc tacgaagggc    480
aagtcgctgt ttcggtccg                                                 499

<210> SEQ ID NO 3
<211> LENGTH: 450
<212> TYPE: DNA
<213> ORGANISM: Artificial
<220> FEATURE:
<223> OTHER INFORMATION: Synthetic noncoding recognition sequence

<400> SEQUENCE: 3
ataggcggcg catgagagaa gcccagacca attacctacc caaaatggag aaagttcacg     60
ttgacatcga ggaagacagc ccattcctca gagctttgca gcggagcttc ccgcagtttg    120
aggtagaagc caagcaggtc actgataatg accatgctaa tgtcagagcg ttttcgcatc    180
tggcttcaaa actgatcgaa acggaggtgg acccatccga cacgatcctt gacattggaa    240
gtgcgcccgc ccgcagaatg tattctaagc acaagtatca ttgtatctgt ccatgagat     300 gtgcggaaga tccggacaga ttgtataagt atgcaactaa gctgaagaaa aactgtaagg    360
aaataactga taaggaattg gacaagaaaa tgaaggagct cgccgccgtc atgagcgacc    420
ctgacctgga aactgagact atgcggtccg                                     450

<210> SEQ ID NO 4
<211> LENGTH: 412
<212> TYPE: DNA
<213> ORGANISM: Artificial
<220> FEATURE:
<223> OTHER INFORMATION: Synthetic noncoding recognition sequence

<400> SEQUENCE: 4
ataggcggcg catgagagaa gcccagacca attacctacc caaaatggag aaagttcacg     60
ttgacatcga ggaagacagc ccattcctca gagctttgca gcggagcttc ccgcagtttg    120
aggtagaagc caagcaggtc actgataatg accatgctaa tgccagagcg ttttcgcatc    180
tggcttcaaa actgatcgaa acggaggtgg acccatccga cacgatcctt gacattggaa    240
gtgcgcccgc ccgcagaatg tattctaagc acaagtatca ttgtatctgt ccatgagat     300 gtgcggaaga tccggacaga ttgtataagt atgcaactaa gctgaagaaa aactgtaagg    360
aaataactga taaggaattg gacaagaaaa tgaaggagct cgccgcggtc cg            412

<210> SEQ ID NO 5
<211> LENGTH: 351
<212> TYPE: DNA
<213> ORGANISM: Artificial
<220> FEATURE:
<223> OTHER INFORMATION: Synthetic noncoding recognition sequence

<400> SEQUENCE: 5
ataggcggcg catgagagaa gcccagacca attacctacc caaaatggag aaagttcacg     60
ttgacatcga ggaagacagc ccattcctca gagctttgca gcggagcttc ccgcagtttg    120
aggtagaagc caagcaggtc actgataatg accatgctaa tgccagagcg ttttcgcatc    180
tggcttcaaa actgatcgaa acggaggtgg acccatccga cacgatcctt gacattggaa    240
```

```
gtgcgcccgc cgcagaatg tattctaagc acaagtatca ttgtatctgt ccgatgagat      300
gtgcggaaga tccggacaga ttgtataagt atgcaactaa gctgcggtcc g             351

<210> SEQ ID NO 6
<211> LENGTH: 309
<212> TYPE: DNA
<213> ORGANISM: Artificial
<220> FEATURE:
<223> OTHER INFORMATION: Synthetic noncoding recognition sequence

<400> SEQUENCE: 6
ataggcggcg catgagagaa gcccagacca attacctacc caaaatggag aaagttcacg     60
ttgacatcga ggaagacagc ccattcctca gagctttgca gcggagcttc ccgcagtttg    120
aggtagaagc caagcaggtc actgataatg accatgctaa tgccagagcg ttttcgcatc    180
tggcttcaaa actgatcgaa acggaggtgg acccatccga cacgatcctt gacattggaa    240
gtgcgcccgc cgcagaatg tattctaagc acaagtatca ttgtatctgt ccgatgagat     300
gtcggaccg                                                            309

<210> SEQ ID NO 7
<211> LENGTH: 248
<212> TYPE: DNA
<213> ORGANISM: Artificial
<220> FEATURE:
<223> OTHER INFORMATION: Synthetic noncoding recognition sequence

<400> SEQUENCE: 7
ataggcggcg catgagagaa gcccagacca attacctacc caaaatggag aaagttcacg     60
ttgacatcga ggaagacagc ccattcctca gagctttgca gcggagcttc ccgcagtttg    120
aggtagaagc caagcaggtc actgataatg accatgctaa tgccagagcg ttttcgcatc    180
tggcttcaaa actgatcgaa acggaggtgg acccatccga cacgatcctt gacattggac    240
ggtccgcg                                                             248

<210> SEQ ID NO 8
<211> LENGTH: 200
<212> TYPE: DNA
<213> ORGANISM: Artificial
<220> FEATURE:
<223> OTHER INFORMATION: Synthetic noncoding recognition sequence

<400> SEQUENCE: 8
ataggcggcg catgagagaa gcccagacca attacctacc caaaatggag aaagttcacg     60
ttgacatcga ggaagacagc ccattcctca gagctttgca gcggagcttc ccgcagtttg    120
aggtagaagc caagcaggtc actgataatg accatgctaa tgccagagcg ttttcgcatc    180
tggcttcaaa actcggtccg                                                200

<210> SEQ ID NO 9
<211> LENGTH: 141
<212> TYPE: DNA
<213> ORGANISM: Artificial
<220> FEATURE:
<223> OTHER INFORMATION: Synthetic noncoding recognition sequence

<400> SEQUENCE: 9
ataggcggcg catgagagaa gcccagacca attacctacc caaaatggag aaagttcacg     60
ttgacatcga ggaagacagc ccattcctca gagctttgca gcggagcttc ccgcagtttg    120
aggtagaagc caagcggtcc g                                              141
```

<210> SEQ ID NO 10
<211> LENGTH: 524
<212> TYPE: DNA
<213> ORGANISM: Venezuelan equine encephalitis virus

<400> SEQUENCE: 10

```
atgggcggcg catgagagaa gcccagacca attacctacc caaaatggag aaagttcacg      60
ttgacatcga ggaagacagc ccattcctca gagctttgca gcggagcttc ccgcagtttg     120
aggtagaagc caagcaggtc actgataatg accatgctaa tgccagagcg ttttcgcatc     180
tggcttcaaa actgatcgaa acggaggtgg acccatccga cacgatcctt gacattggaa     240
gtgcgcccgc ccgcagaatg tattctaagc acaagtatca ttgtatctgt ccgatgagat     300
gtgcggaaga tccggacaga ttgtataagt atgcaactaa gctgaagaaa aactgtaagg     360
aaataactga taaggaattg gacaagaaaa tgaaggagct cgccgccgtc atgagcgacc     420
ctgacctgga aactgagact atgtgcctcc acgacgacga gtcgtgtcgc tacgaagggc     480
aagtcgctgt ttaccaggat gtatacgcgg ttgacggacc gacc                      524
```

<210> SEQ ID NO 11
<211> LENGTH: 502
<212> TYPE: DNA
<213> ORGANISM: Artificial
<220> FEATURE:
<223> OTHER INFORMATION: Synthetic noncoding recognition sequence

<400> SEQUENCE: 11

```
ataggcggcg catgagagaa gcccagacca attacctacc caaaatggag aaagttcacg      60
ttgacatcga ggaagacagc ccattcctca gagctttgca gcggagcttc ccgcagtttg     120
aggtagaagc caagcaggtc actgataatg accatgctaa tgccagagcg ttttcgcatc     180
tggcttcaaa actgatcgaa acggaggtgg acccatccga cacgatcctt gacattggaa     240
gtgcgcccgc ccgcagaatg tattctaagc acaagtatca ttgtatctgt ccgatgagat     300
gtgcggaaga tccggacaga ttgtataagt atgcaactaa gctgaagaaa aactgtaagg     360
aaataactga taaggaattg gacaagaaaa tgaaggagct cgccgccgtc atgagcgacc     420
ctgacctgga aactgagact atgtgcctcc acgacgacga gtcgtgtcgc tacgaagggc     480
aagtcgctgt ttcggtccga cc                                              502
```

<210> SEQ ID NO 12
<211> LENGTH: 453
<212> TYPE: DNA
<213> ORGANISM: Artificial
<220> FEATURE:
<223> OTHER INFORMATION: Synthetic noncoding recognition sequence

<400> SEQUENCE: 12

```
ataggcggcg catgagagaa gcccagacca attacctacc caaaatggag aaagttcacg      60
ttgacatcga ggaagacagc ccattcctca gagctttgca gcggagcttc ccgcagtttg     120
aggtagaagc caagcaggtc actgataatg accatgctaa tgccagagcg ttttcgcatc     180
tggcttcaaa actgatcgaa acggaggtgg acccatccga cacgatcctt gacattggaa     240
gtgcgcccgc ccgcagaatg tattctaagc acaagtatca ttgtatctgt ccgatgagat     300
gtgcggaaga tccggacaga ttgtataagt atgcaactaa gctgaagaaa aactgtaagg     360
aaataactga taaggaattg gacaagaaaa tgaaggagct cgccgccgtc atgagcgacc     420
ctgacctgga aactgagact atgcggtccg acc                                  453
```

```
<210> SEQ ID NO 13
<211> LENGTH: 415
<212> TYPE: DNA
<213> ORGANISM: Artificial
<220> FEATURE:
<223> OTHER INFORMATION: Synthetic noncoding recognition sequence

<400> SEQUENCE: 13
ataggcggcg catgagagaa gcccagacca attacctacc caaaatggag aaagttcacg      60
ttgacatcga ggaagacagc ccattcctca gagctttgca gcggagcttc ccgcagtttg     120
aggtagaagc caagcaggtc actgataatg accatgctaa tgccagagcg ttttcgcatc     180
tggcttcaaa actgatcgaa acggaggtgg acccatccga cacgatcctt gacattggaa     240
gtgcgcccgc ccgcagaatg tattctaagc acaagtatca ttgtatctgt ccgatgagat     300
gtgcggaaga tccggacaga ttgtataagt atgcaactaa gctgaagaaa aactgtaagg     360
aaataactga taaggaattg gacaagaaaa tgaaggagct cgccgcggtc cgacc          415

<210> SEQ ID NO 14
<211> LENGTH: 354
<212> TYPE: DNA
<213> ORGANISM: Artificial
<220> FEATURE:
<223> OTHER INFORMATION: Synthetic noncoding recognition sequence

<400> SEQUENCE: 14
ataggcggcg catgagagaa gcccagacca attacctacc caaaatggag aaagttcacg      60
ttgacatcga ggaagacagc ccattcctca gagctttgca gcggagcttc ccgcagtttg     120
aggtagaagc caagcaggtc actgataatg accatgctaa tgccagagcg ttttcgcatc     180
tggcttcaaa actgatcgaa acggaggtgg acccatccga cacgatcctt gacattggaa     240
gtgcgcccgc ccgcagaatg tattctaagc acaagtatca ttgtatctgt ccgatgagat     300
gtgcggaaga tccggacaga ttgtataagt atgcaactaa gctgcggacc gacc           354

<210> SEQ ID NO 15
<211> LENGTH: 312
<212> TYPE: DNA
<213> ORGANISM: Artificial
<220> FEATURE:
<223> OTHER INFORMATION: Synthetic noncoding recognition sequence

<400> SEQUENCE: 15
ataggcggcg catgagagaa gcccagacca attacctacc caaaatggag aaagttcacg      60
ttgacatcga ggaagacagc ccattcctca gagctttgca gcggagcttc ccgcagtttg     120
aggtagaagc caagcaggtc actgataatg accatgctaa tgccagagcg ttttcgcatc     180
tggcttcaaa actgatcgaa acggaggtgg acccatccga cacgatcctt gacattggaa     240
gtgcgcccgc ccgcagaatg tattctaagc acaagtatca ttgtatctgt ccgatgagat     300
gtcggaccga cc                                                         312

<210> SEQ ID NO 16
<211> LENGTH: 249
<212> TYPE: DNA
<213> ORGANISM: Artificial
<220> FEATURE:
<223> OTHER INFORMATION: Synthetic noncoding recognition sequence

<400> SEQUENCE: 16
ataggcggcg catgagagaa gcccagacca attacctacc caaaatggag aaagttcacg      60
```
ttgacatcga ggaagacagc ccattcctca gagctttgca gcggagcttc ccgcagtttg    120
aggtagaagc caagcaggtc actgataatg accatgctaa tgccagagcg ttttcgcatc    180
tggcttcaaa actgatcgaa acggaggtgg acccatccga cacgatcctt gacattggac    240
ggtccgacc                                                            249

<210> SEQ ID NO 17
<211> LENGTH: 203
<212> TYPE: DNA
<213> ORGANISM: Artificial
<220> FEATURE:
<223> OTHER INFORMATION: Synthetic noncoding recognition sequence

<400> SEQUENCE: 17
ataggcggcg catgagagaa gcccagacca attacctacc caaaatggag aaagttcacg     60
ttgacatcga ggaagacagc ccattcctca gagctttgca gcggagcttc ccgcagtttg    120
aggtagaagc caagcaggtc actgataatg accatgctaa tgccagagcg ttttcgcatc    180
tggcttcaaa actcggtccg acc                                            203

<210> SEQ ID NO 18
<211> LENGTH: 144
<212> TYPE: DNA
<213> ORGANISM: Artificial
<220> FEATURE:
<223> OTHER INFORMATION: Synthetic noncoding recognition sequence

<400> SEQUENCE: 18
ataggcggcg catgagagaa gcccagacca attacctacc caaaatggag aaagttcacg     60
ttgacatcga ggaagacagc ccattcctca gagctttgca gcggagcttc ccgcagtttg    120
aggtagaagc caagcggacc gacc                                           144

<210> SEQ ID NO 19
<211> LENGTH: 521
<212> TYPE: DNA
<213> ORGANISM: Artificial
<220> FEATURE:
<223> OTHER INFORMATION: Synthetic noncoding recognition sequence

<400> SEQUENCE: 19
atgggcggcg cgtgagagaa gcccagacca attacctacc caaagtggag aaagttcacg     60
ttgacatcga ggaagacagc ccattcctca gagctttgca gcggagcttc ccgcagtttg    120
aggtagaagc caagcaggtc actgatagtg accgtgctag tgccagagcg ttttcgcatc    180
tggcttcaaa actgatcgaa acggaggtgg acccatccga cacgatcctt gacattggaa    240
gtgcgcccgc ccgcagagtg tattctaagc acaagtatca ttgtatctgt ccggtgaggt    300
gtgcggaaga tccggacaga ttgtataagt gtgcaactaa gctgaagaaa aactgtaagg    360
aaataactga taaggaattg dacaagaaag tgaaggagct cgccgccgtc gtgagcgacc    420
ctgacctgga aactgagact gtgtgcctcc acgacgacga gtcgtgtcgc tacgaagggc    480
aagtcgctgt ttaccagggt gtatacgcgg ttgacggacc g                        521

<210> SEQ ID NO 20
<211> LENGTH: 499
<212> TYPE: DNA
<213> ORGANISM: Artificial
<220> FEATURE:
<223> OTHER INFORMATION: Synthetic noncoding recognition sequence

<400> SEQUENCE: 20

```
ataggcggcg cgtgagagaa gcccagacca attacctacc caaagtggag aaagttcacg    60
ttgacatcga ggaagacagc ccattcctca gagctttgca gcggagcttc ccgcagtttg   120
aggtagaagc caagcaggtc actgatagtg accgtgctag tgccagagcg ttttcgcatc   180
tggcttcaaa actgatcgaa acggaggtgg acccatccga cacgatcctt gacattggaa   240
gtgcgcccgc ccgcagagtg tattctaagc acaagtatca ttgtatctgt ccggtgaggt   300
gtgcggaaga tccggacaga ttgtataagt gtgcaactaa gctgaagaaa aactgtaagg   360
aaataactga taaggaattg acaagaaag tgaaggagct cgccgccgtc gtgagcgacc    420
ctgacctgga aactgagact gtgtgcctcc acgacgacga gtcgtgtcgc tacgaagggc   480
aagtcgctgt ttcggtccg                                                499

<210> SEQ ID NO 21
<211> LENGTH: 450
<212> TYPE: DNA
<213> ORGANISM: Artificial
<220> FEATURE:
<223> OTHER INFORMATION: Synthetic noncoding recognition sequence

<400> SEQUENCE: 21
atgggcggcg cgtgagagaa gcccagacca attacctacc caaagtggag aaagttcacg    60
ttgacatcga ggaagacagc ccattcctca gagctttgca gcggagcttc ccgcagtttg   120
aggtagaagc caagcaggtc actgatagtg accgtgctag tgccagagcg ttttcgcatc   180
tggcttcaaa actgatcgaa acggaggtgg acccatccga cacgatcctt gacattggaa   240
gtgcgcccgc ccgcagagtg tattctaagc acaagtatca ttgtatctgt ccggtgaggt   300
gtgcggaaga tccggacaga ttgtataagt gtgcaactaa gctgaagaaa aactgtaagg   360
aaataactga taaggaattg acaagaaag tgaaggagct cgccgccgtc gtgagcgacc    420
ctgacctgga aactgagact atgcggtccg                                   450

<210> SEQ ID NO 22
<211> LENGTH: 412
<212> TYPE: DNA
<213> ORGANISM: Artificial
<220> FEATURE:
<223> OTHER INFORMATION: Synthetic noncoding recognition sequence

<400> SEQUENCE: 22
atgggcggcg cgtgagagaa gcccagacca attacctacc caaagtggag aaagttcacg    60
ttgacatcga ggaagacagc ccattcctca gagctttgca gcggagcttc ccgcagtttg   120
aggtagaagc caagcaggtc actgatagtg accgtgctag tgccagagcg ttttcgcatc   180
tggcttcaaa actgatcgaa acggaggtgg acccatccga cacgatcctt gacattggaa   240
gtgcgcccgc ccgcagagtg tattctaagc acaagtatca ttgtatctgt ccggtgaggt   300
gtgcggaaga tccggacaga ttgtataagt gtgcaactaa gctgaagaaa aactgtaagg   360
aaataactga taaggaattg acaagaaaa tgaaggagct cgccgcggtc cg           412

<210> SEQ ID NO 23
<211> LENGTH: 351
<212> TYPE: DNA
<213> ORGANISM: Artificial
<220> FEATURE:
<223> OTHER INFORMATION: Synthetic noncoding recognition sequence

<400> SEQUENCE: 23
atgggcggcg cgtgagagaa gcccagacca attacctacc caaagtggag aaagttcacg    60
```

| | |
|---|---|
| ttgacatcga ggaagacagc ccattcctca gagctttgca gcggagcttc ccgcagtttg | 120 |
| aggtagaagc caagcaggtc actgatagtg accgtgctag tgccagagcg ttttcgcatc | 180 |
| tggcttcaaa actgatcgaa acggaggtgg acccatccga cacgatcctt gacattggaa | 240 |
| gtgcgcccgc ccgcagagtg tattctaagc acaagtatca ttgtatctgt ccggtgaggt | 300 |
| gtgcggaaga tccggacaga ttgtataagt atgcaactaa gctgcggtcc g | 351 |

```
<210> SEQ ID NO 24
<211> LENGTH: 309
<212> TYPE: DNA
<213> ORGANISM: Artificial
<220> FEATURE:
<223> OTHER INFORMATION: Synthetic noncoding recognition sequence

<400> SEQUENCE: 24
```

| | |
|---|---|
| atgggcggcg cgtgagagaa gcccagacca attacctacc caaagtggag aaagttcacg | 60 |
| ttgacatcga ggaagacagc ccattcctca gagctttgca gcggagcttc ccgcagtttg | 120 |
| aggtagaagc caagcaggtc actgatagtg accgtgctag tgccagagcg ttttcgcatc | 180 |
| tggcttcaaa actgatcgaa acggaggtgg acccatccga cacgatcctt gacattggaa | 240 |
| gtgcgcccgc ccgcagagtg tattctaagc acaagtatca ttgtttctgt ccgatgagat | 300 |
| gtcggtccg | 309 |

```
<210> SEQ ID NO 25
<211> LENGTH: 246
<212> TYPE: DNA
<213> ORGANISM: Artificial
<220> FEATURE:
<223> OTHER INFORMATION: Synthetic noncoding recognition sequence

<400> SEQUENCE: 25
```

| | |
|---|---|
| atgggcggcg cgtgagagaa gcccagacca attacctacc caaagtggag aaagttcacg | 60 |
| ttgacatcga ggaagacagc ccattcctca gagctttgca gcggagcttc ccgcagtttg | 120 |
| aggtagaagc caagcaggtc actgatagtg accgtgctag tgccagagcg ttttcgcatc | 180 |
| tggcttcaaa actgatcgaa acggaggtgg acccatccga cacgatcctt gacattggac | 240 |
| ggtccg | 246 |

```
<210> SEQ ID NO 26
<211> LENGTH: 200
<212> TYPE: DNA
<213> ORGANISM: Artificial
<220> FEATURE:
<223> OTHER INFORMATION: Synthetic noncoding recognition sequence

<400> SEQUENCE: 26
```

| | |
|---|---|
| atgggcggcg cgtgagagaa gcccagacca attacctacc caaagtggag aaagttcacg | 60 |
| ttgacatcga ggaagacagc ccattcctca gagctttgca gcggagcttc ccgcagtttg | 120 |
| aggtagaagc caagcaggtc actgatagtg accgtgctag tgccagagcg ttttcgcatc | 180 |
| tggcttcaaa actcggtccg | 200 |

```
<210> SEQ ID NO 27
<211> LENGTH: 524
<212> TYPE: DNA
<213> ORGANISM: Artificial
<220> FEATURE:
<223> OTHER INFORMATION: Synthetic noncoding recognition sequence

<400> SEQUENCE: 27
```

```
atgggcggcg cgtgagagaa gcccagacca attacctacc caaagtggag aaagttcacg    60
ttgacatcga ggaagacagc ccattcctca gagctttgca gcggagcttc ccgcagtttg   120
aggtagaagc caagcaggtc actgatagtg accgtgctag tgccagagcg ttttcgcatc   180
tggcttcaaa actgatcgaa acggaggtgg acccatccga cacgatcctt gacattggaa   240
gtgcgcccgc ccgcagagtg tattctaagc acaagtatca ttgtatctgt ccggtgaggt   300
gtgcggaaga tccggacaga ttgtataagt gtgcaactaa gctgaagaaa aactgtaagg   360
aaataactga taaggaattg acaagaaag tgaaggagct cgccgccgtc gtgagcgacc   420
ctgacctgga aactgagact gtgtgcctcc acgacgacga gtcgtgtcgc tacgaagggc   480
aagtcgctgt ttaccagggt gtatacgcgg ttgacggacc gacc                    524

<210> SEQ ID NO 28
<211> LENGTH: 507
<212> TYPE: DNA
<213> ORGANISM: Artificial
<220> FEATURE:
<223> OTHER INFORMATION: Synthetic noncoding recognition sequence

<400> SEQUENCE: 28
atgggcggcg cgtgagagaa gcccagacca attacctacc caaagtggag aaagttcacg    60
ttgacatcga ggaagacagc ccattcctca gagctttgca gcggagcttc ccgcagtttg   120
aggtagaagc caagcaggtc actgatagtg accgtgctag tgccagagcg ttttcgcatc   180
tggcttcaaa actgatcgaa acggaggtgg acccatccga cacgatcctt gacattggaa   240
gtgcgcccgc ccgcagagtg tattctaagc acaagtatca ttgtatctgt ccggtgaggt   300
gtgcggaaga tccggacaga ttgtataagt gtgcaactaa gctgaagaaa aactgtaagg   360
aaataactga taaggaattg acaagaaag tgaaggagct cgccgccgtc gtgagcgacc   420
ctgacctgga aactgagact gtgtgcctcc acgacgacga gtcgtgtcgc tacgaagggc   480
aagtcgctgt ttcggtccga ggcgacc                                       507

<210> SEQ ID NO 29
<211> LENGTH: 453
<212> TYPE: DNA
<213> ORGANISM: Artificial
<220> FEATURE:
<223> OTHER INFORMATION: Synthetic noncoding recognition sequence

<400> SEQUENCE: 29
atgggcggcg cgtgagagaa gcccagacca attacctacc caaagtggag aaagttcacg    60
ttgacatcga ggaagacagc ccattcctca gagctttgca gcggagcttc ccgcagtttg   120
aggtagaagc caagcaggtc actgatagtg accgtgctag tgccagagcg ttttcgcatc   180
tggcttcaaa actgatcgaa acggaggtgg acccatccga cacgatcctt gacattggaa   240
gtgcgcccgc ccgcagagtg tattctaagc acaagtatca ttgtatctgt ccggtgaggt   300
gtgcggaaga tccggacaga ttgtataagt gtgcaactaa gctgaagaaa aactgtaagg   360
aaataactga taaggaattg acaagaaag tgaaggagct cgccgccgtc gtgagcgacc   420
ctgacctgga aactgagact gtgcggtccg acc                                453

<210> SEQ ID NO 30
<211> LENGTH: 415
<212> TYPE: DNA
<213> ORGANISM: Artificial
<220> FEATURE:
<223> OTHER INFORMATION: Synthetic noncoding recognition sequence
```

```
<400> SEQUENCE: 30
atgggcggcg cgtgagagaa gcccagacca attacctacc caaagtggag aaagttcacg    60
ttgacatcga ggaagacagc ccattcctca gagctttgca gcggagcttc ccgcagtttg   120
aggtagaagc caagcaggtc actgatagtg accgtgctag tgccagagcg ttttcgcatc   180
tggcttcaaa actgatcgaa acggaggtgg acccatccga cacgatcctt gacattggaa   240
gtgcgcccgc ccgcagagtg tattctaagc acaagtatca ttgtatctgt ccggtgaggt   300
gtgcggaaga tccggacaga ttgtataagt gtgcaactaa gctgaagaaa aactgtaagg   360
aaataactga taaggaattg gacaagaaaa tgaaggagct cgccgcggtc cgacc         415

<210> SEQ ID NO 31
<211> LENGTH: 354
<212> TYPE: DNA
<213> ORGANISM: Artificial
<220> FEATURE:
<223> OTHER INFORMATION: Synthetic noncoding recognition sequence

<400> SEQUENCE: 31
atgggcggcg cgtgagagaa gcccagacca attacctacc caaagtggag aaagttcacg    60
ttgacatcga ggaagacagc ccattcctca gagctttgca gcggagcttc ccgcagtttg   120
aggtagaagc caagcaggtc actgatagtg accgtgctag tgccagagcg ttttcgcatc   180
tggcttcaaa actgatcgaa acggaggtgg acccatccga cacgatcctt gacattggaa   240
gtgcgcccgc ccgcagagtg tattctaagc acaagtatca ttgtatctgt ccggtgaggt   300
gtgcggaaga tccggacaga ttgtataata tgcaacctaa tctgcggtcc gacc          354

<210> SEQ ID NO 32
<211> LENGTH: 312
<212> TYPE: DNA
<213> ORGANISM: Artificial
<220> FEATURE:
<223> OTHER INFORMATION: Synthetic noncoding recognition sequence

<400> SEQUENCE: 32
atgggcggcg cgtgagagaa gcccagacca attacctacc caaagtggag aaagttcacg    60
ttgacatcga ggaagacagc ccattcctca gagctttgca gcggagcttc ccgcagtttg   120
aggtagaagc caagcaggtc actgatagtg accgtgctag tgccagagcg ttttcgcatc   180
tggcttcaaa actgatcgaa acggaggtgg acccatccga cacgatcctt gacattggaa   240
gtgcgcccgc ccgcagagtg tattctaagc acaagtatca ttgtatctgt ccgatgagat   300
gtcggtccga cc                                                       312

<210> SEQ ID NO 33
<211> LENGTH: 249
<212> TYPE: DNA
<213> ORGANISM: Artificial
<220> FEATURE:
<223> OTHER INFORMATION: Synthetic noncoding recognition sequence

<400> SEQUENCE: 33
atgggcggcg cgtgagagaa gcccagacca attacctacc caaagtggag aaagttcacg    60
ttgacatcga ggaagacagc ccattcctca gagctttgca gcggagcttc ccgcagtttg   120
aggtagaagc caagcaggtc actgatagtg accgtgctag tgccagagcg ttttcgcatc   180
tggcttcaaa actgatcgaa acggaggtgg acccatccga cacgatcctt gacattggac   240
ggaccgacc                                                           249
```

```
<210> SEQ ID NO 34
<211> LENGTH: 203
<212> TYPE: DNA
<213> ORGANISM: Artificial
<220> FEATURE:
<223> OTHER INFORMATION: Synthetic noncoding recognition sequence

<400> SEQUENCE: 34
atgggcggcg cgtgagagaa gcccagacca attacctacc caaagtggag aaagttcacg      60
ttgacatcga ggaagacagc ccattcctca gagctttgca gcggagcttc ccgcagtttg     120
aggtagaagc caagcaggtc actgatagtg accgtgctag tgccagagcg ttttcgcatc     180
tggcttcaaa actcggtccg acc                                             203

<210> SEQ ID NO 35
<211> LENGTH: 521
<212> TYPE: DNA
<213> ORGANISM: Artificial
<220> FEATURE:
<223> OTHER INFORMATION: Synthetic noncoding recognition sequence

<400> SEQUENCE: 35
atgggcggcg catgagagaa gcccagacca attacctacc caaataggag aaagttcacg      60
ttgacatcga ggaagacagc ccattcctca gagctttgca gcggagcttc ccgcagtttg     120
aggtagaagc caagcaggtc actgataatg accatgctaa tgccagagcg ttttcgcatc     180
tggcttcaaa actgatcgaa acggaggtgg acccatccga cacgatcctt gacattggaa     240
gtgcgcccgc ccgcagaatg tattctaagc acaagtatca ttgtatctgt ccgatgagat     300
gtgcggaaga tccggacaga ttgtataagt atgcaactaa gctgaagaaa aactgtaagg     360
aaataactga taaggaattg dacaagaaaa tgaaggagct cgccgccgtc atgagcgacc     420
ctgacctgga aactgagact atgtgcctcc acgacgacga gtcgtgtcgc tacgaagggc     480
aagtcgctgt ttaccaggat gtatacgcgg ttgacggacc g                         521

<210> SEQ ID NO 36
<211> LENGTH: 499
<212> TYPE: DNA
<213> ORGANISM: Artificial
<220> FEATURE:
<223> OTHER INFORMATION: Synthetic noncoding recognition sequence

<400> SEQUENCE: 36
ataggcggcg catgagagaa gcccagacca attacctacc caaataggag aaagttcacg      60
ttgacatcga ggaagacagc ccattcctca gagctttgca gcggagcttc ccgcagtttg     120
aggtagaagc caagcaggtc actgataatg accatgctaa tgccagagcg ttttcgcatc     180
tggcttcaaa actgatcgaa acggaggtgg acccatccga cacgatcctt gacattggaa     240
gtgcgcccgc ccgcagaatg tattctaagc acaagtatca ttgtatctgt ccgatgagat     300
gtgcggaaga tccggacaga ttgtataagt atgcaactaa gctgaagaaa aactgtaagg     360
aaataactga taaggaattg gacaagaaaa tgaaggagct cgccgccgtc atgagcgacc     420
ctgacctgga aactgagact atgtgcctcc acgacgacga gtcgtgtcgc tacgaagggc     480
aagtcgctgt ttcggtccg                                                  499

<210> SEQ ID NO 37
<211> LENGTH: 450
<212> TYPE: DNA
<213> ORGANISM: Artificial
<220> FEATURE:
```

<223> OTHER INFORMATION: Synthetic noncoding recognition sequence

<400> SEQUENCE: 37
ataggcggcg catgagagaa gcccagacca attacctacc caaataggag aaagttcacg     60
ttgacatcga ggaagacagc ccattcctca gagctttgca gcggagcttc ccgcagtttg    120
aggtagaagc caagcaggtc actgataatg accatgctaa tgtcagagcg ttttcgcatc    180
tggcttcaaa actgatcgaa acggaggtgg acccatccga cacgatcctt gacattggaa    240
gtgcgcccgc ccgcagaatg tattctaagc acaagtatca ttgtatctgt ccgatgagat    300
gtgcggaaga tccggacaga ttgtataagt atgcaactaa gctgaagaaa aactgtaagg    360
aaataactga taaggaattg acaagaaaa tgaaggagct cgccgccgtc atgagcgacc    420
ctgacctgga aactgagact atgcggtccg                                    450

<210> SEQ ID NO 38
<211> LENGTH: 412
<212> TYPE: DNA
<213> ORGANISM: Artificial
<220> FEATURE:
<223> OTHER INFORMATION: Synthetic noncoding recognition sequence

<400> SEQUENCE: 38
ataggcggcg catgagagaa gcccagacca attacctacc caaataggag aaagttcacg     60
ttgacatcga ggaagacagc ccattcctca gagctttgca gcggagcttc ccgcagtttg    120
aggtagaagc caagcaggtc actgataatg accatgctaa tgccagagcg ttttcgcatc    180
tggcttcaaa actgatcgaa acggaggtgg acccatccga cacgatcctt gacattggaa    240
gtgcgcccgc ccgcagaatg tattctaagc acaagtatca ttgtatctgt ccgatgagat    300
gtgcggaaga tccggacaga ttgtataagt atgcaactaa gctgaagaaa aactgtaagg    360
aaataactga taaggaattg acaagaaaa tgaaggagct cgccgcggtc cg            412

<210> SEQ ID NO 39
<211> LENGTH: 351
<212> TYPE: DNA
<213> ORGANISM: Artificial
<220> FEATURE:
<223> OTHER INFORMATION: Synthetic noncoding recognition sequence

<400> SEQUENCE: 39
ataggcggcg catgagagaa gcccagacca attacctacc caaataggag aaagttcacg     60
ttgacatcga ggaagacagc ccattcctca gagctttgca gcggagcttc ccgcagtttg    120
aggtagaagc caagcaggtc actgataatg accatgctaa tgccagagcg ttttcgcatc    180
tggcttcaaa actgatcgaa acggaggtgg acccatccga cacgatcctt gacattggaa    240
gtgcgcccgc ccgcagaatg tattctaagc acaagtatca ttgtatctgt ccgatgagat    300
gtgcggaaga tccggacaga ttgtataagt atgcaactaa gctgcggtcc g             351

<210> SEQ ID NO 40
<211> LENGTH: 309
<212> TYPE: DNA
<213> ORGANISM: Artificial
<220> FEATURE:
<223> OTHER INFORMATION: Synthetic noncoding recognition sequence

<400> SEQUENCE: 40
ataggcggcg catgagagaa gcccagacca attacctacc caaataggag aaagttcacg     60
ttgacatcga ggaagacagc ccattcctca gagctttgca gcggagcttc ccgcagtttg    120

-continued

| | |
|---|---|
| aggtagaagc caagcaggtc actgataatg accatgctaa tgccagagcg ttttcgcatc | 180 |
| tggcttcaaa actgatcgaa acggaggtgg acccatccga cacgatcctt gacattggaa | 240 |
| gtgcgcccgc ccgcagaatg tattctaagc acaagtatca ttgtatctgt ccgatgagat | 300 |
| gtcggaccg | 309 |

<210> SEQ ID NO 41
<211> LENGTH: 248
<212> TYPE: DNA
<213> ORGANISM: Artificial
<220> FEATURE:
<223> OTHER INFORMATION: Synthetic noncoding recognition sequence

<400> SEQUENCE: 41

| | |
|---|---|
| ataggcggcg catgagagaa gcccagacca attacctacc caaataggag aaagttcacg | 60 |
| ttgacatcga ggaagacagc ccattcctca gagctttgca gcggagcttc ccgcagtttg | 120 |
| aggtagaagc caagcaggtc actgataatg accatgctaa tgccagagcg ttttcgcatc | 180 |
| tggcttcaaa actgatcgaa acggaggtgg acccatccga cacgatcctt gacattggac | 240 |
| ggtccgcg | 248 |

<210> SEQ ID NO 42
<211> LENGTH: 200
<212> TYPE: DNA
<213> ORGANISM: Artificial
<220> FEATURE:
<223> OTHER INFORMATION: Synthetic noncoding recognition sequence

<400> SEQUENCE: 42

| | |
|---|---|
| ataggcggcg catgagagaa gcccagacca attacctacc caaataggag aaagttcacg | 60 |
| ttgacatcga ggaagacagc ccattcctca gagctttgca gcggagcttc ccgcagtttg | 120 |
| aggtagaagc caagcaggtc actgataatg accatgctaa tgccagagcg ttttcgcatc | 180 |
| tggcttcaaa actcggtccg | 200 |

<210> SEQ ID NO 43
<211> LENGTH: 524
<212> TYPE: DNA
<213> ORGANISM: Artificial
<220> FEATURE:
<223> OTHER INFORMATION: Synthetic noncoding recognition sequence

<400> SEQUENCE: 43

| | |
|---|---|
| atgggcggcg catgagagaa gcccagacca attacctacc caaataggag aaagttcacg | 60 |
| ttgacatcga ggaagacagc ccattcctca gagctttgca gcggagcttc ccgcagtttg | 120 |
| aggtagaagc caagcaggtc actgataatg accatgctaa tgccagagcg ttttcgcatc | 180 |
| tggcttcaaa actgatcgaa acggaggtgg acccatccga cacgatcctt gacattggaa | 240 |
| gtgcgcccgc ccgcagaatg tattctaagc acaagtatca ttgtatctgt ccgatgagat | 300 |
| gtgcggaaga tccggacaga ttgtataagt atgcaactaa gctgaagaaa aactgtaagg | 360 |
| aaataactga taaggaattg acaagaaaaa tgaaggagct cgccgccgtc atgagcgacc | 420 |
| ctgacctgga aactgagact atgtgcctcc acgacgacga gtcgtgtcgc tacgaagggc | 480 |
| aagtcgctgt ttaccaggat gtatacgcgg ttgacggacc gacc | 524 |

<210> SEQ ID NO 44
<211> LENGTH: 502
<212> TYPE: DNA
<213> ORGANISM: Artificial
<220> FEATURE:

<223> OTHER INFORMATION: Synthetic noncoding recognition sequence

<400> SEQUENCE: 44

```
ataggcggcg catgagagaa gcccagacca attacctacc caaataggag aaagttcacg      60
ttgacatcga ggaagacagc ccattcctca gagctttgca gcggagcttc ccgcagtttg     120
aggtagaagc caagcaggtc actgataatg accatgctaa tgccagagcg ttttcgcatc     180
tggcttcaaa actgatcgaa acggaggtgg acccatccga cacgatcctt gacattggaa     240
gtgcgcccgc ccgcagaatg tattctaagc acaagtatca ttgtatctgt ccgatgagat     300
gtgcggaaga tccggacaga ttgtataagt atgcaactaa gctgaagaaa aactgtaagg     360
aaataactga taaggaattg gacaagaaaa tgaaggagct cgccgccgtc atgagcgacc     420
ctgacctgga aactgagact atgtgcctcc acgacgacga gtcgtgtcgc tacgaagggc     480
aagtcgctgt ttcggtccga cc                                              502
```

<210> SEQ ID NO 45
<211> LENGTH: 453
<212> TYPE: DNA
<213> ORGANISM: Artificial
<220> FEATURE:
<223> OTHER INFORMATION: Synthetic noncoding recognition sequence

<400> SEQUENCE: 45

```
ataggcggcg catgagagaa gcccagacca attacctacc caaataggag aaagttcacg      60
ttgacatcga ggaagacagc ccattcctca gagctttgca gcggagcttc ccgcagtttg     120
aggtagaagc caagcaggtc actgataatg accatgctaa tgccagagcg ttttcgcatc     180
tggcttcaaa actgatcgaa acggaggtgg acccatccga cacgatcctt gacattggaa     240
gtgcgcccgc ccgcagaatg tattctaagc acaagtatca ttgtatctgt ccgatgagat     300
gtgcggaaga tccggacaga ttgtataagt atgcaactaa gctgaagaaa aactgtaagg     360
aaataactga taaggaattg gacaagaaaa tgaaggagct cgccgccgtc atgagcgacc     420
ctgacctgga aactgagact atgcggtccg acc                                  453
```

<210> SEQ ID NO 46
<211> LENGTH: 415
<212> TYPE: DNA
<213> ORGANISM: Artificial
<220> FEATURE:
<223> OTHER INFORMATION: Synthetic noncoding recognition sequence

<400> SEQUENCE: 46

```
ataggcggcg catgagagaa gcccagacca attacctacc caaataggag aaagttcacg      60
ttgacatcga ggaagacagc ccattcctca gagctttgca gcggagcttc ccgcagtttg     120
aggtagaagc caagcaggtc actgataatg accatgctaa tgccagagcg ttttcgcatc     180
tggcttcaaa actgatcgaa acggaggtgg acccatccga cacgatcctt gacattggaa     240
gtgcgcccgc ccgcagaatg tattctaagc acaagtatca ttgtatctgt ccgatgagat     300
gtgcggaaga tccggacaga ttgtataagt atgcaactaa gctgaagaaa aactgtaagg     360
aaataactga taaggaattg gacaagaaaa tgaaggagct cgccgcggtc cgacc          415
```

<210> SEQ ID NO 47
<211> LENGTH: 354
<212> TYPE: DNA
<213> ORGANISM: Artificial
<220> FEATURE:
<223> OTHER INFORMATION: Synthetic noncoding recognition sequence -continued

<400> SEQUENCE: 47

```
ataggcggcg catgagagaa gcccagacca attacctacc caaataggag aaagttcacg      60
ttgacatcga ggaagacagc ccattcctca gagctttgca gcggagcttc ccgcagtttg     120
aggtagaagc caagcaggtc actgataatg accatgctaa tgccagagcg ttttcgcatc     180
tggcttcaaa actgatcgaa acggaggtgg acccatccga cacgatcctt gacattggaa     240
gtgcgcccgc ccgcagaatg tattctaagc acaagtatca ttgtatctgt ccgatgagat     300
gtgcggaaga tccggacaga ttgtataagt atgcaactaa gctgcggacc gacc           354
```

<210> SEQ ID NO 48
<211> LENGTH: 312
<212> TYPE: DNA
<213> ORGANISM: Artificial
<220> FEATURE:
<223> OTHER INFORMATION: Synthetic noncoding recognition sequence

<400> SEQUENCE: 48

```
ataggcggcg catgagagaa gcccagacca attacctacc caaataggag aaagttcacg      60
ttgacatcga ggaagacagc ccattcctca gagctttgca gcggagcttc ccgcagtttg     120
aggtagaagc caagcaggtc actgataatg accatgctaa tgccagagcg ttttcgcatc     180
tggcttcaaa actgatcgaa acggaggtgg acccatccga cacgatcctt gacattggaa     240
gtgcgcccgc ccgcagaatg tattctaagc acaagtatca ttgtatctgt ccgatgagat     300
gtcggaccga cc                                                        312
```

<210> SEQ ID NO 49
<211> LENGTH: 249
<212> TYPE: DNA
<213> ORGANISM: Artificial
<220> FEATURE:
<223> OTHER INFORMATION: Synthetic noncoding recognition sequence

<400> SEQUENCE: 49

```
ataggcggcg catgagagaa gcccagacca attacctacc caaataggag aaagttcacg      60
ttgacatcga ggaagacagc ccattcctca gagctttgca gcggagcttc ccgcagtttg     120
aggtagaagc caagcaggtc actgataatg accatgctaa tgccagagcg ttttcgcatc     180
tggcttcaaa actgatcgaa acggaggtgg acccatccga cacgatcctt gacattggac     240
ggtccgacc                                                            249
```

<210> SEQ ID NO 50
<211> LENGTH: 203
<212> TYPE: DNA
<213> ORGANISM: Artificial
<220> FEATURE:
<223> OTHER INFORMATION: Synthetic noncoding recognition sequence

<400> SEQUENCE: 50

```
ataggcggcg catgagagaa gcccagacca attacctacc caaataggag aaagttcacg      60
ttgacatcga ggaagacagc ccattcctca gagctttgca gcggagcttc ccgcagtttg     120
aggtagaagc caagcaggtc actgataatg accatgctaa tgccagagcg ttttcgcatc     180
tggcttcaaa actcggtccg acc                                            203
```

<210> SEQ ID NO 51
<211> LENGTH: 166
<212> TYPE: DNA
<213> ORGANISM: Artificial
<220> FEATURE:

<223> OTHER INFORMATION: Synthetic noncoding recognition sequence

<400> SEQUENCE: 51
ataggcggcg catgagagaa gcccagacca attaccgata tcgaagccaa gcaggtcact    60
gataatgacc atgctaatgc cagagcgttt tcgcatctgg cttcaaaact gatcgaaacg   120
gaggtggacc catccgacac gatccttgac attggacgga ccgacc                  166

<210> SEQ ID NO 52
<211> LENGTH: 19
<212> TYPE: DNA
<213> ORGANISM: Artificial
<220> FEATURE:
<223> OTHER INFORMATION: Synthetic noncoding recognition sequence

<400> SEQUENCE: 52
attttgtttt taatatttc                                                 19

<210> SEQ ID NO 53
<211> LENGTH: 752
<212> TYPE: DNA
<213> ORGANISM: Artificial
<220> FEATURE:
<223> OTHER INFORMATION: Synthetic noncoding recognition sequence

<400> SEQUENCE: 53
atgggcggcg catgagagaa gcccagacca attacctacc caaaatggag aaagttcacg    60
ttgacatcga ggaagacagc ccattcctca gagctttgca gcggagcttc ccgcagtttg   120
aggtagaagc caagcaggtc actgataatg accatgctaa tgccagagcg ttttcgcatc   180
tggcttcaaa actgatcgaa acggaggtgg acccatccga cacgatcctt gacattggaa   240
gtgcgcccgc ccgcagaatg tattctaagc acaagtatca ttgtatctgt ccgatgagat   300
gtgcggaaga tccggacaga ttgtataagt atgcaactaa gctgaagaaa aactgtaagg   360
aaataactga taaggaattg gacaagaaaa tgaaggagct cgccgccgtc atgagcgacc   420
ctgacctgga aactgagact atgtgcctcc acgacgacga gtcgtgtcgc tacgaagggc   480
aagtcgctgt ttaccaggat gtatacgcgg ttgacggacc gatgcagatc ttcgtgaaga   540
ccctgaccgg caagaccatc accttggagg tggagcccag tgacaccatc gagaatgtga   600
aggccaagat ccaggataaa gagggcatcc cccctgacca gcagaggctg atctttgccg   660
gcaagcagct agaagatggc cgcactctct ctgattacaa catccagaaa gagtcgaccc   720
tgcacctggt cctccgtctg aggggcggac cg                                 752

<210> SEQ ID NO 54
<211> LENGTH: 755
<212> TYPE: DNA
<213> ORGANISM: Artificial
<220> FEATURE:
<223> OTHER INFORMATION: Synthetic noncoding recognition sequence

<400> SEQUENCE: 54
ataggcggcg catgagagaa gcccagacca attacctacc caaaatggag aaagttcacg    60
ttgacatcga ggaagacagc ccattcctca gagctttgca gcggagcttc ccgcagtttg   120
aggtagaagc caagcaggtc actgataatg accatgctaa tgccagagcg ttttcgcatc   180
tggcttcaaa actgatcgaa acggaggtgg acccatccga cacgatcctt gacattggaa   240
gtgcgcccgc ccgcagaatg tattctaagc acaagtatca ttgtatctgt ccgatgagat   300
gtgcggaaga tccggacaga ttgtataagt atgcaactaa gctgaagaaa aactgtaagg   360

```
aaataactga taaggaattg acaagaaaa tgaaggagct cgccgccgtc atgagcgacc      420
ctgacctgga aactgagact atgtgcctcc acgacgacga gtcgtgtcgc tacgaagggc      480
aagtcgctgt ttaccaggat gtatacgcgg ttgacggacc gatgcagatc ttcgtgaaga      540
ccctgaccgg caagaccatc accttggagg tggagcccag tgacaccatc gagaatgtga      600
aggccaagat ccaggataaa gagggcatcc cccctgacca gcagaggctg atctttgccg      660
gcaagcagct agaagatggc cgcactctct ctgattacaa catccagaaa gagtcgaccc      720
tgcacctggt cctccgtctg agggggcggac cgacc                               755

<210> SEQ ID NO 55
<211> LENGTH: 374
<212> TYPE: DNA
<213> ORGANISM: Venezuelan equine encephalitis virus

<400> SEQUENCE: 55
tggtcactag tgaccaccat gtgtctgctc gccaatgtga cgttcccatg tgctcaacca       60
ccaatttgct acgacagaaa accagcagag actttggcca tgctcagcgt taacatccct      120
gctgggagga tcagccgtaa ttattataat tggcttggtg ctggctacta ttgtggccat      180
gtacgtgctg accaaccaga acataattg aatacagcag caattggcaa gctgcttaca      240
tagaactcgc ggcgattggc atgccgcttt aaaatttta ttttattttt cttttctttt      300
ccgaatcgga ttttgttttt aatatttcaa aaaaaaaaa aaaaaaaaa aaaaaaaaa      360 aaaaaaaaaa aaaa                                                      374

<210> SEQ ID NO 56
<211> LENGTH: 166
<212> TYPE: DNA
<213> ORGANISM: Venezuelan equine encephalitis virus

<400> SEQUENCE: 56
tgaatacagc agcaattggc aagctgctta catagaactc gcggcgattg gcatgccgct       60
ttaaaatttt tatttattt tctttctt ttccgaatcg gattttgttt taatatttc      120 aaaaaaaaaa aaaaaaaaaa aaaaaaaaaa aaaaaaaaaa aaaaa                     166

<210> SEQ ID NO 57
<211> LENGTH: 115
<212> TYPE: DNA
<213> ORGANISM: Artificial
<220> FEATURE:
<223> OTHER INFORMATION: Synthetic noncoding recognition sequence

<400> SEQUENCE: 57
taagcatgcc gctttaaaat ttttattta ttttctttt ctttccgaa tcggattttg       60 ttttaatat tcaaaaaaa aaaaaaaaaa aaaaaaaaaa aaaaaaaaaa aaaaa           115

<210> SEQ ID NO 58
<211> LENGTH: 49
<212> TYPE: DNA
<213> ORGANISM: Artificial
<220> FEATURE:
<223> OTHER INFORMATION: Synthetic noncoding recognition sequence

<400> SEQUENCE: 58
taagcatgca ttttgttttt aatatttcaa aaaaaaaaa aaaaaaaaa                   49

<210> SEQ ID NO 59
<211> LENGTH: 118
<212> TYPE: DNA
```

```
<213> ORGANISM: Artificial
<220> FEATURE:
<223> OTHER INFORMATION: Synthetic noncoding recognition sequence

<400> SEQUENCE: 59
taagcatgcc gctttaaaat ttttatttta tttttctttt cttttccgaa tcggattttg     60
tttttaatat ttcaaaaaaa aaaaaaaaaa aaaaaaaaaa aaaaaaaa                 118

<210> SEQ ID NO 60
<211> LENGTH: 34
<212> TYPE: DNA
<213> ORGANISM: Artificial
<220> FEATURE:
<223> OTHER INFORMATION: Oligonucleotide primer

<400> SEQUENCE: 60
cctcggaccg accatgtcac tagtgaccac catg                                 34

<210> SEQ ID NO 61
<211> LENGTH: 73
<212> TYPE: DNA
<213> ORGANISM: Artificial
<220> FEATURE:
<223> OTHER INFORMATION: Oligonucleotide primer

<400> SEQUENCE: 61
tttttttttt tttttttttt tttttttttt tttttttttt ttttttgaaat attaaaaaca    60 aaatccgatt cgg                                                        73

<210> SEQ ID NO 62
<211> LENGTH: 20
<212> TYPE: DNA
<213> ORGANISM: Artificial
<220> FEATURE:
<223> OTHER INFORMATION: Oligonucleotide primer

<400> SEQUENCE: 62
accgtcaccc tggatgctgt                                                 20

<210> SEQ ID NO 63
<211> LENGTH: 39
<212> TYPE: DNA
<213> ORGANISM: Artificial
<220> FEATURE:
<223> OTHER INFORMATION: Oligonucleotide primer

<400> SEQUENCE: 63
cctcggaccg aaacagcgac ttgcccttcg tagcgacac                            39

<210> SEQ ID NO 64
<211> LENGTH: 39
<212> TYPE: DNA
<213> ORGANISM: Artificial
<220> FEATURE:
<223> OTHER INFORMATION: Oligonucleotide primer

<400> SEQUENCE: 64
cctcggaccg catagtctca gtttccaggt cagggtcgc                            39

<210> SEQ ID NO 65
<211> LENGTH: 43
<212> TYPE: DNA
<213> ORGANISM: Artificial
<220> FEATURE:
<223> OTHER INFORMATION: Oligonucleotide primer
```

<400> SEQUENCE: 65
cctcggaccg cggcgagctc cttcattttc ttgtccaatt cct					43

<210> SEQ ID NO 66
<211> LENGTH: 44
<212> TYPE: DNA
<213> ORGANISM: Artificial
<220> FEATURE:
<223> OTHER INFORMATION: Oligonucleotide primer

<400> SEQUENCE: 66
cctcggaccg cagcttagtt gcatacttat acaatctgtc cgga					44

<210> SEQ ID NO 67
<211> LENGTH: 45
<212> TYPE: DNA
<213> ORGANISM: Artificial
<220> FEATURE:
<223> OTHER INFORMATION: Oligonucleotide primer

<400> SEQUENCE: 67
cctcggaccg acatctcatc ggacagatac aatgatactt gtgct					45

<210> SEQ ID NO 68
<211> LENGTH: 39
<212> TYPE: DNA
<213> ORGANISM: Artificial
<220> FEATURE:
<223> OTHER INFORMATION: Oligonucleotide primer

<400> SEQUENCE: 68
cctcggaccg tccaatgtca aggatcgtgt cggatgggt					39

<210> SEQ ID NO 69
<211> LENGTH: 40
<212> TYPE: DNA
<213> ORGANISM: Artificial
<220> FEATURE:
<223> OTHER INFORMATION: Oligonucleotide primer

<400> SEQUENCE: 69
cctcggaccg agttttgaag ccagatgcga aaacgctctg					40

<210> SEQ ID NO 70
<211> LENGTH: 39
<212> TYPE: DNA
<213> ORGANISM: Artificial
<220> FEATURE:
<223> OTHER INFORMATION: Oligonucleotide primer

<400> SEQUENCE: 70
cctcggaccg cttggcttct acctcaaact gcgggaagc					39

<210> SEQ ID NO 71
<211> LENGTH: 40
<212> TYPE: DNA
<213> ORGANISM: Artificial
<220> FEATURE:
<223> OTHER INFORMATION: Oligonucleotide primer

<400> SEQUENCE: 71
gaccaattac ctacccaaat aggagaaagt tcacgttgac					40

<210> SEQ ID NO 72
<211> LENGTH: 40
<212> TYPE: DNA

```
<213> ORGANISM: Artificial
<220> FEATURE:
<223> OTHER INFORMATION: Oligonucleotide primer

<400> SEQUENCE: 72
gtcaacgtga actttctcct atttgggtag gtaattggtc                              40

<210> SEQ ID NO 73
<211> LENGTH: 26
<212> TYPE: DNA
<213> ORGANISM: Artificial
<220> FEATURE:
<223> OTHER INFORMATION: Oligonucleotide primer

<400> SEQUENCE: 73
ataggcggcg cgtgagagaa gcccag                                             26

<210> SEQ ID NO 74
<211> LENGTH: 34
<212> TYPE: DNA
<213> ORGANISM: Artificial
<220> FEATURE:
<223> OTHER INFORMATION: Oligonucleotide primer

<400> SEQUENCE: 74
cctacccaaa gtggagaaag ttcacgttga catc                                    34

<210> SEQ ID NO 75
<211> LENGTH: 36
<212> TYPE: DNA
<213> ORGANISM: Artificial
<220> FEATURE:
<223> OTHER INFORMATION: Oligonucleotide primer

<400> SEQUENCE: 75
caggtcactg atagtgaccg tgctagtgcc agagcg                                  36

<210> SEQ ID NO 76
<211> LENGTH: 28
<212> TYPE: DNA
<213> ORGANISM: Artificial
<220> FEATURE:
<223> OTHER INFORMATION: Oligonucleotide primer

<400> SEQUENCE: 76
gcccgcccgc agagtgtatt ctaagcac                                           28

<210> SEQ ID NO 77
<211> LENGTH: 32
<212> TYPE: DNA
<213> ORGANISM: Artificial
<220> FEATURE:
<223> OTHER INFORMATION: Oligonucleotide primer

<400> SEQUENCE: 77
gtatctgtcc ggtgaggtgt gcggaagatc cg                                      32

<210> SEQ ID NO 78
<211> LENGTH: 30
<212> TYPE: DNA
<213> ORGANISM: Artificial
<220> FEATURE:
<223> OTHER INFORMATION: Oligonucleotide primer

<400> SEQUENCE: 78
gacagattgt ataagtgtgc aactaagctg                                         30
```

```
<210> SEQ ID NO 79
<211> LENGTH: 26
<212> TYPE: DNA
<213> ORGANISM: Artificial
<220> FEATURE:
<223> OTHER INFORMATION: Oligonucleotide primer

<400> SEQUENCE: 79
gaatggacaa gaaagtgaag gagctc                                      26

<210> SEQ ID NO 80
<211> LENGTH: 28
<212> TYPE: DNA
<213> ORGANISM: Artificial
<220> FEATURE:
<223> OTHER INFORMATION: Oligonucleotide primer

<400> SEQUENCE: 80
ccgtcgtgag cgaccctgac ctggaaac                                    28

<210> SEQ ID NO 81
<211> LENGTH: 25
<212> TYPE: DNA
<213> ORGANISM: Artificial
<220> FEATURE:
<223> OTHER INFORMATION: Oligonucleotide primer

<400> SEQUENCE: 81
gaaactgaga ctgtgtgcct ccacg                                       25

<210> SEQ ID NO 82
<211> LENGTH: 25
<212> TYPE: DNA
<213> ORGANISM: Artificial
<220> FEATURE:
<223> OTHER INFORMATION: Oligonucleotide primer

<400> SEQUENCE: 82
gtttaccagg gtgtatacgc ggttg                                       25

<210> SEQ ID NO 83
<211> LENGTH: 21
<212> TYPE: DNA
<213> ORGANISM: Artificial
<220> FEATURE:
<223> OTHER INFORMATION: Oligonucleotide primer

<400> SEQUENCE: 83
tcagtggaac gaaaactcac g                                           21

<210> SEQ ID NO 84
<211> LENGTH: 30
<212> TYPE: DNA
<213> ORGANISM: Artificial
<220> FEATURE:
<223> OTHER INFORMATION: Oligonucleotide primer

<400> SEQUENCE: 84
tttgatatcg gtaattggtc tgggcttctc                                  30

<210> SEQ ID NO 85
<211> LENGTH: 28
<212> TYPE: DNA
<213> ORGANISM: Artificial
<220> FEATURE:
<223> OTHER INFORMATION: Oligonucleotide primer
```

```
<400> SEQUENCE: 85
tttgatatcg aagccaagca ggtcactg                                      28

<210> SEQ ID NO 86
<211> LENGTH: 20
<212> TYPE: DNA
<213> ORGANISM: Artificial
<220> FEATURE:
<223> OTHER INFORMATION: Oligonucleotide primer

<400> SEQUENCE: 86
gcaacgcggg gaggcagaca                                               20

<210> SEQ ID NO 87
<211> LENGTH: 26
<212> TYPE: DNA
<213> ORGANISM: Artificial
<220> FEATURE:
<223> OTHER INFORMATION: Oligonucleotide primer

<400> SEQUENCE: 87
gcatgctcaa ttatgtttct ggttgg                                        26

<210> SEQ ID NO 88
<211> LENGTH: 20
<212> TYPE: DNA
<213> ORGANISM: Artificial
<220> FEATURE:
<223> OTHER INFORMATION: Oligonucleotide primer

<400> SEQUENCE: 88
cgacatagtc tagtccgcca                                               20

<210> SEQ ID NO 89
<211> LENGTH: 28
<212> TYPE: DNA
<213> ORGANISM: Artificial
<220> FEATURE:
<223> OTHER INFORMATION: Oligonucleotide primer

<400> SEQUENCE: 89
gcatgcattt tgttttaat atttcaaa                                       28

<210> SEQ ID NO 90
<211> LENGTH: 21
<212> TYPE: DNA
<213> ORGANISM: Artificial
<220> FEATURE:
<223> OTHER INFORMATION: Oligonucleotide primer

<400> SEQUENCE: 90
gctcacatgt tctttcctgc g                                             21

<210> SEQ ID NO 91
<211> LENGTH: 34
<212> TYPE: DNA
<213> ORGANISM: Artificial
<220> FEATURE:
<223> OTHER INFORMATION: Oligonucleotide primer

<400> SEQUENCE: 91
cctcggaccg accatgttcc cgttccagcc aatg                               34

<210> SEQ ID NO 92
<211> LENGTH: 31
<212> TYPE: DNA
```

```
<213> ORGANISM: Artificial
<220> FEATURE:
<223> OTHER INFORMATION: Oligonucleotide primer

<400> SEQUENCE: 92
acatgcatgc ttattgctcg cagttctccg g                              31

<210> SEQ ID NO 93
<211> LENGTH: 34
<212> TYPE: DNA
<213> ORGANISM: Artificial
<220> FEATURE:
<223> OTHER INFORMATION: Oligonucleotide primer

<400> SEQUENCE: 93
acatgcatgc ttaccattgc tcgcagttct ccgg                           34

<210> SEQ ID NO 94
<211> LENGTH: 31
<212> TYPE: DNA
<213> ORGANISM: Artificial
<220> FEATURE:
<223> OTHER INFORMATION: Oligonucleotide primer

<400> SEQUENCE: 94
cctcggtccg accatgctag tgaccaccat g                              31

<210> SEQ ID NO 95
<211> LENGTH: 20
<212> TYPE: DNA
<213> ORGANISM: Artificial
<220> FEATURE:
<223> OTHER INFORMATION: Oligonucleotide primer

<400> SEQUENCE: 95
acatacacgg tagtcacaat                                           20

<210> SEQ ID NO 96
<211> LENGTH: 35
<212> TYPE: DNA
<213> ORGANISM: Artificial
<220> FEATURE:
<223> OTHER INFORMATION: Oligonucleotide primer

<400> SEQUENCE: 96
catcgacgga ccgatgcaga tcttcgtgaa gaccc                          35

<210> SEQ ID NO 97
<211> LENGTH: 34
<212> TYPE: DNA
<213> ORGANISM: Artificial
<220> FEATURE:
<223> OTHER INFORMATION: Oligonucleotide primer

<400> SEQUENCE: 97
gattttcggt ccgcccctca gacggaggac cagg                           34

<210> SEQ ID NO 98
<211> LENGTH: 31
<212> TYPE: DNA
<213> ORGANISM: Artificial
<220> FEATURE:
<223> OTHER INFORMATION: Oligonucleotide primer

<400> SEQUENCE: 98
cctcggaccg atgttcccgt tccagccaat g                              31
```

```
<210> SEQ ID NO 99
<211> LENGTH: 6
<212> TYPE: PRT
<213> ORGANISM: Artificial
<220> FEATURE:
<223> OTHER INFORMATION: dHcapU fusion protein amino acid sequence

<400> SEQUENCE: 99

Arg Gly Gly Pro Met Phe
1               5

<210> SEQ ID NO 100
<211> LENGTH: 7
<212> TYPE: PRT
<213> ORGANISM: Artificial
<220> FEATURE:
<223> OTHER INFORMATION: dHgpU fusion protein amino acid sequence

<400> SEQUENCE: 100

Arg Gly Gly Pro Thr Met Ser
1               5

<210> SEQ ID NO 101
<211> LENGTH: 6
<212> TYPE: PRT
<213> ORGANISM: Artificial
<220> FEATURE:
<223> OTHER INFORMATION: dHcap amino acid sequence

<400> SEQUENCE: 101

Val Asp Gly Pro Met Phe
1               5

<210> SEQ ID NO 102
<211> LENGTH: 18
<212> TYPE: DNA
<213> ORGANISM: Artificial
<220> FEATURE:
<223> OTHER INFORMATION: dHcap coding sequence

<400> SEQUENCE: 102
gttgacggac cgatgttc                                                 18

<210> SEQ ID NO 103
<211> LENGTH: 7
<212> TYPE: PRT
<213> ORGANISM: Artificial
<220> FEATURE:
<223> OTHER INFORMATION: dHgp amino acid sequence

<400> SEQUENCE: 103

Val Asp Gly Pro Thr Met Ser
1               5

<210> SEQ ID NO 104
<211> LENGTH: 21
<212> TYPE: DNA
<213> ORGANISM: Artificial
<220> FEATURE:
<223> OTHER INFORMATION: dHgp coding sequence

<400> SEQUENCE: 104
gttgacggac cgaccatgtc a                                             21

<210> SEQ ID NO 105
<211> LENGTH: 4
<212> TYPE: PRT
```

```
<213> ORGANISM: Artificial
<220> FEATURE:
<223> OTHER INFORMATION: GP protein sequence

<400> SEQUENCE: 105

Pro Thr Met Ser
1

<210> SEQ ID NO 106
<211> LENGTH: 12
<212> TYPE: DNA
<213> ORGANISM: Artificial
<220> FEATURE:
<223> OTHER INFORMATION: Nucleotide sequence with dHcapU and dHgpU
      ubiquintin cleavage coding sequence

<400> SEQUENCE: 106
aggggcggac cg                                                          12
```

US 8,460,913 B2

PROMOTERLESS CASSETTES FOR EXPRESSION OF ALPHA VIRUS STRUCTURAL PROTEINS

STATEMENT OF PRIORITY

This application is a 35 U.S.C. §371 national phase application of International Application Serial No. PCT/US2008/007701, filed Jun. 20, 2008, which claims the benefit, under 35 U.S.C. §119(e), of U.S. Provisional Application No. 60/936,637, filed Jun. 21, 2007, the entire contents of each of which are incorporated herein by reference.

STATEMENT OF GOVERNMENT SUPPORT

Aspects of this invention were supported by funding under Grant No. 5 UO1 A1057286-03 from the National Institutes of Health. The U.S. Government has certain rights in this invention.

STATEMENT REGARDING ELECTRONIC FILING OF A SEQUENCE LISTING

A Sequence Listing in ASCII text format, submitted under 37 C.F.R. §1.821, entitled 9368-9X$_{13}$ ST25.txt, 45,828 bytes in size, generated on Dec. 3, 2012 and filed via EFS-Web, is provided in lieu of a paper copy. This Sequence Listing is hereby incorporated herein by reference into the specification for its disclosures.

FIELD OF THE INVENTION

The present invention relates to improved constructs for and methods of making recombinant alphavirus particles.

BACKGROUND OF THE INVENTION

Alphaviruses are currently being used as vector platforms to develop vaccines for infectious diseases and cancer (e.g., see U.S. Pat. Nos. 5,792,462; 6,156,558; 5,811,407; 6,531,135; 6,541,010; 6,783,939; 6,844,188; 6,982,087; 7,045,335; 5,789,245; 6,015,694; 5,739,026; Pushko et al., *Virology* 239 (2):389-401 (1997), Frolov et al., *J. Virol.* 71(1):248-258 (1997); Smerdou and Liljestrom, *J. Virol.* 73(2):1092-1098 (1999)). Alphaviruses comprise a genus in the Togaviridae family, and members of the genus are found throughout the world, in both vertebrate and invertebrate hosts. Among the most studied alphaviruses for vector platforms are Venezuelan Equine Encephalitis (VEE) Virus, Semliki Forest Virus (SFV), and Sindbis Virus (SV), the prototype member of the genus.

One such vector platform is the alphavirus replicon system, described in U.S. Pat. No. 6,190,666 to Garoff et al., U.S. Pat. Nos. 5,792,462 and 6,156,558 to Johnston et al., U.S. Pat. Nos. 5,814,482, 5,843,723, 5,789,245, 6,015,694, 6,105,686 and 6,376,236 to Dubensky et al; U.S. Published Application No. 2002-0015945 A1 (Polo et al.), U.S. Published Application No. 2001-0016199 (Johnston et al.), Frolov et al. (1996) *Proc. Natl. Acad. Sci. USA* 93:11371-11377 and Pushko et al. (1997) *Virology* 239:389-401. An alphavirus replicon vector is engineered to contain and express one or more nucleic acids of interest, where the nucleic acid of interest can encode, for example, an antigen, a cytokine, a ribozyme, or an enzyme. The alphavirus replicon vector can be derived from any alphavirus, such as Venezuelan Equine Encephalitis (VEE) virus, Sindbis virus, e.g., strain TR339, South African Arbovirus No. 86, and Semliki Forest virus, among others. The vector is then introduced into cells in culture that allow replication of alphaviruses and in which the structural proteins of the alphavirus are also expressed, so that the vector is packaged by the alphavirus structural proteins into alphavirus replicon particles (ARPs). ARPs are then harvested from the culture and delivered into subjects for a variety of therapeutic purposes.

Various constructs have been developed to enhance immunogenicity and effectiveness of the ARP system in vaccine applications. Many of these constructs have also been designed to decrease the likelihood of formation of replication-competent alphavirus through recombination of genome fragments. Johnston et al. (U.S. Pat. Nos. 5,792,462 and 6,156,558) recognized the potential for recombination from a single helper system (in which the complete set of structural protein genes of an alphavirus are on one RNA molecule and the nonstructural protein genes and heterologous nucleic acid of interest are on a separate replicon RNA), and thus designed "double-helper" systems that utilized two helper RNAs to encode the structural proteins. Dubensky et al. (U.S. Pat. No. 5,789,245) and Polo et al. (U.S. Pat. No. 6,242,259) describe the use of two DNA alphavirus structural protein expression cassettes, stably transformed into a packaging cell line, to package alphavirus vectors by production of RNAs expressing those structural proteins upon introduction of a replicating alphavirus vector into cultures of the packaging cell. Liljestrom and colleagues have presented data confirming that a "single helper system" will generate wild-type alphavirus particles (Berglund, et al. *Biotechnology* 11(8): 916-920 (1993)). Smith et al have described other novel RNA helpers that direct expression of the structural proteins (WO 2004/085660).

By distributing the viral coding sequences among three nucleic acids, two of which comprise the helper system, as described above, the theoretical frequency of recombination that would create a replication-competent virus ("RCV") is reduced significantly relative to single helper systems. These systems include the use of the alphaviral subgenomic promoter, often referred to as the 26S promoter or the viral junction region promoter, to provide a construct which functions as an independent transcriptional unit and the use of the alphavirus RNA polymerase recognition signals, so that the helper systems can take advantage of the presence of the alphavirus replication machinery for amplification and efficient expression of helper functions.

In existing systems, known packaging signals are typically included in replicon RNAs and excluded from helper constructs. However, helper RNAs are nonetheless packaged or copackaged at a lower frequency (Lu and Silver. *J. Virol Methods*, 91(1):59-65 (2001)), and helper constructs with terminal recognition signals will be amplified and expressed in the presence of a replicon, potentially yielding recombination events with other helper molecules or the replicon RNA.

Animal studies with alphavirus replicon particles have employed doses ranging from $10^5$ to $10^8$, with $10^7$, $5 \times 10^7$, and $10^8$ having been effectively employed in non-human primates, which are also the doses being used in human clinical trials. In addition, higher doses such as $2 \times 10^8$, $5 \times 10^8$ and $10^9$ are also useful in applications for humans. Such dosages require large scale manufacturing procedures, and at such scale, it is statistically possible that replication-competent alphavirus may be generated with existing RNA helper systems.

Thus, there remains a need in the art to provide improved systems for manufacturing alphavirus replicon particles to further reduce the predicted frequency for formation of replication-competent alphavirus, and to optimize manufacturing strategies and costs.

The present invention provides alphavirus RNA helper molecules encoding alphavirus structural proteins that lack a promoter sequence, thereby significantly decreasing the theoretical number of functional recombination events that might occur between the helper molecules and the replicon vector, resulting in a decrease in the theoretical prediction for the rate of formation of replication-competent alphavirus during the production of recombinant alphavirus particles.

SUMMARY OF THE INVENTION

The present invention provides an isolated RNA molecule comprising: a) an alphavirus 5' replication recognition sequence, wherein an initiation codon has been removed from the 5' replication recognition sequence; b) a nucleotide sequence encoding an alphavirus structural protein; and c) an alphavirus 3' replication recognition sequence, with the proviso that the RNA molecule does not contain a promoter that directs transcription of the nucleotide sequence of (b), and wherein the alphavirus 5' and 3' replication recognition sequences direct replication of the entire RNA molecule in the presence of alphavirus nonstructural proteins.

Additionally provided herein is a method of making an alphavirus replicon particle, comprising introducing one or more of the RNA molecules of this invention into a cell, whereby the combination of RNA molecules encodes all alphavirus structural proteins necessary for production of an alphavirus replicon particle, along with an alphavirus replicon RNA, under conditions whereby alphavirus replicon particles are produced.

Further provided is a method of making an alphavirus replicon particle, comprising introducing into a cell: a) an alphavirus replicon RNA; b) one or more of the RNA molecules of this invention; and c) one or more promoter-assisted alphavirus helper constructs, whereby the combination of RNA molecules of (b) and helper constructs of (c) encodes all alphavirus structural proteins necessary for production of an alphavirus replicon particle, under conditions whereby an alphavirus replicon particle is produced.

In additional embodiments, the present invention provides a population of alphavirus replicon particles, wherein the population contains no detectable replication-competent virus particles, as determined by passage on permissive cells in culture.

Also provided herein is a population of alphavirus replicon particles, wherein the population contains no detectable replication-competent virus particles, as determined by passage on permissive cells in culture, wherein the alphavirus replicon particles comprise one or more attenuating mutations in either an alphavirus structural protein or an alphavirus nonstructural protein or both an alphavirus structural protein and an alphavirus nonstructural protein.

Furthermore, the present invention provides a method of inducing an immune response in a subject, comprising administering an effective amount of the population of alphavirus replicon particles of this invention to the subject.

DETAILED DESCRIPTION OF THE INVENTION

Figure 1:
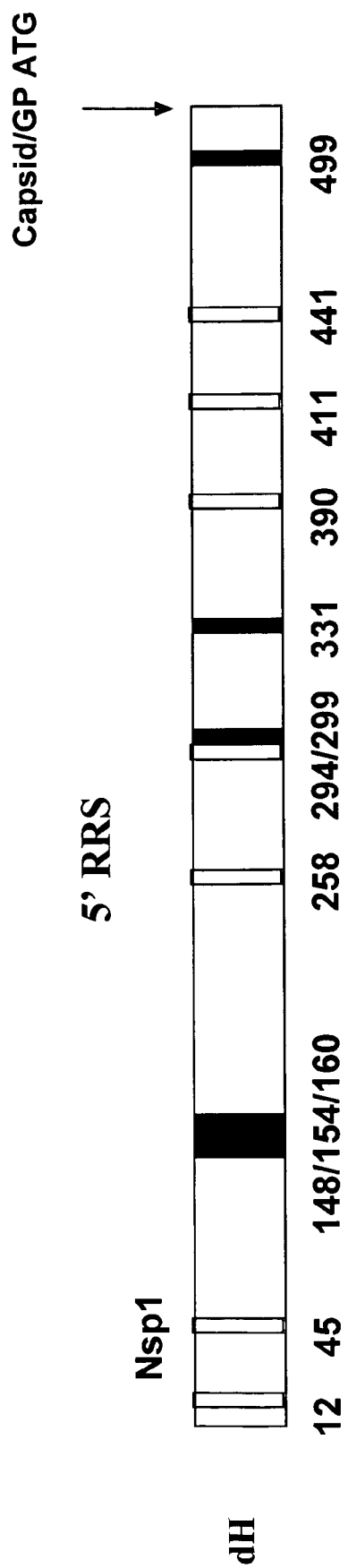
FIG. 1 shows the structure of the 5' replication recognition sequence (RRS) of a full length (FL) promoterless helper molecule. The location of start codons upstream of the capsid or glycoprotein (GP) initiation codons within the 5' replication recognition sequence are indicated with outlined lines and black lines. Outlined lines indicate start codons that are in-frame with the coding sequence for capsid or GP. Black lines indicate start codons that are out-of-reading frame with the coding sequence for capsid or GP. Numbers under the vertical lines indicate the first nucleotide positions for the putative start codons in the 5' replication recognition sequence, numbered from the 5' terminus of the molecule.

As used herein, "a," "an" and "the" can mean one or more than one, depending on the context in which it is used. For example, "a" cell can mean one cell or multiple cells.

Also as used herein, "and/or" refers to and encompasses any and all possible combinations of one or more of the associated listed items, as well as the lack of combinations when interpreted in the alternative ("or").

Furthermore, the term "about," as used herein when referring to a measurable value such as an amount of a compound or agent of this invention, dose, time, temperature, and the like, is meant to encompass variations of ±20%, ±10%, ±5%, ±1%, ±0.5%, or even ±0.1% of the specified amount.

The terms "5' alphavirus replication recognition sequence," "3' alphavirus replication recognition sequence," "5' replication recognition sequence," and "3' replication recognition sequence refer to the RNA sequences found in alphaviruses, sequences derived therefrom, or synthetic sequences based on conserved sequences among various alphaviruses, that are recognized by the nonstructural alphavirus replicase proteins and lead to replication of viral RNA. In some embodiments, these sequences can be in the form of DNA to facilitate the preparation, mutation and/or manipulation of the constructs, plasmids and nucleic acids of this invention to produce VRPs. These sequences are also referred to as the "5' and 3' ends," 5' and 3' viral sequences required for nonstructural protein-mediated amplification, 5' and 3' sequences required for nonstructural protein-mediated amplification, 5' or 3' conserved sequence element (CSE), 5' or 3' non-coding regions, 5' or 3' noncoding region sequences, 5' or 3' viral sequences required in cis for replication, 5' or 3' sequence that initiates transcription of an alphavirus, and/or alphavirus 5' and 3' sequences, with the 5' and 3' designations referring to their location in the alphavirus genome. In the nucleic acid molecules of this invention, the use of these 5' and 3' ends will result in replication and/or transcription of the RNA sequence encoded between the two ends. These sequences can be modified by standard molecular biological techniques (e.g., truncated at either end and/or modified to remove initiation (i.e., start) codons or to enhance translatability) to further minimize the potential for recombination and/or to introduce cloning sites, etc., with the proviso that they must still be recognized by the alphavirus replication machinery.

As used herein, the terms "initiation codon" or "start codon" refer to a codon that is AUG in RNA and ATG in DNA that may or may not be used in the translation of a functional protein.

The term "alphavirus structural protein/protein(s)" refers to one or a combination of the structural proteins encoded by alphaviruses. These are produced by the wild type virus as a polyprotein and are described generally in the literature as C-E3-E2-6k-E1. E3 and 6k serve as membrane translocation/transport signals for the two glycoproteins, E2 and E1. Thus, use of the term E1 herein can refer to E1, E3-E1, 6k-E1, or E3-6k-E1, and use of the term E2 herein can refer to E2, E3-E2, 6k-E2, PE2, p62 or E3-6k-E2. The term "glycoprotein helper" or "GP helper" typically refers herein to a helper molecule that encodes both E2 and E1 glycoproteins; in certain embodiments of this invention, E1 and E2 are encoded on separate helper molecules.

The terms "helper(s)" and "helper molecules" are used interchangeably and refer to a nucleic acid molecule that expresses nucleic acid encoding one or more alphavirus structural proteins.

The terms "helper cell" and "packaging cell" are used interchangeably herein and refer to a cell in which alphavirus replicon particles are produced. The helper cell comprises a set of helper molecules and/or helper constructs as described herein that encode one or more alphavirus structural proteins. The helpers can be RNA or DNA or both. The helper cell or packaging cell can be any cell that is alphavirus-permissive, i.e., that can produce alphavirus particles upon introduction of a replicon RNA. Alphavirus-permissive cells include, but are not limited to, Vero, baby hamster kidney (BHK), 293, 293T/17 (ATCC accession number CRL-11268), chicken embryo fibroblast (CEF), UMNSAH/DF-1 (ATCC accession number CRL-12203) and Chinese hamster ovary (CHO) cells.

A "promoter" as used herein is a nucleic acid sequence that directs transcription of an RNA molecule.

An "isolated cell" as used herein is a cell or population of cells that have been removed from the environment in which the cell occurs naturally and/or altered or modified from the state in which the cell occurs in its natural environment. An isolated cell of this invention can be a cell, for example, in a cell culture. An isolated cell of this invention can also be a cell that can be in an animal and/or introduced into an animal and wherein the cell has been altered or modified, e.g., by the introduction into the cell of an alphavirus particle of this invention.

As used herein, an "alphavirus subgenomic promoter" or "26S promoter" is a promoter as originally defined in a wild type alphavirus genome that directs transcription of a subgenomic messenger RNA as part of the alphavirus replication process.

The heterologous nucleic acid (e.g., a gene of interest or "GOI" or nucleic acid of interest or "NOI") used in some embodiments of this invention is a nucleic acid that is not present in the genome of a wild type alphavirus and/or is not present in the genome of a wild type alphavirus in the same order as it exists in a recombinant nucleic acid of this invention. For example, in certain embodiments, the NOI can encode one or more alphavirus structural proteins (e.g., C, PE2/E2, E1, E3, 6K) when they are used as helper nucleic acids in the assembly of infectious, defective alphavirus particles (e.g., alphavirus replicon particles) or as immunogens for vaccines against diseases caused by certain alphaviruses.

The present invention is based on the surprising and unexpected discovery that RNA molecules comprising a nucleotide sequence encoding alphavirus structural protein(s) and alphavirus 5' and 3' sequences, wherein an initiation codon has been removed from the 5' replication recognition sequence, but lacking a promoter sequence (e.g., a subgenomic alphavirus promoter sequence, sometimes referred to as a 26S, or viral junction region, promoter) can be replicated such that the full-length positive strand RNA can be translated efficiently and produce sufficient amounts of alphavirus structural proteins in trans for the production of alphavirus replicon particles in cultured cell lines. These "promoterless" RNA molecules, sometimes referred to herein as "Δ26S helpers," increase the theoretical safety margin in a population of alphavirus replicon particles (e.g., produced for use as a vaccine or adjuvant) by decreasing the predicted theoretical frequency of generation of functional recombination events that occur between the helper molecules and the replicon vector.

Any split helper system requires a minimum of two independent recombination events to generate replication-competent alphavirus (RCV). For alphaviruses, recombination is thought to be predominantly the result of random strand switching by the RNA replication complex (Weiss et al 1991), although homologous recombination has also been reported. For the first recombination event, the replication complex could, for example, begin at the 3' end of an RNA helper molecule in the split helper/replicon packaging systems disclosed in the literature (e.g., Johnston et al. U.S. Pat. No. 5,792,462). If the complex continued replication of this helper RNA through the 26S or viral junction region and then switched to the foreign nucleotide sequence in the replicon RNA as a template and completed replication through the replicon 5' end, the resulting "recombinant replicon intermediate" would contain sequence encoding all the non-structural proteins, some or all of the transcriptional unit containing the foreign nucleic acid of interest (NOI) coding region, and the new inserted transcriptional unit expressing one of the alphaviral structural proteins. In order for an RCV to be created, a subsequent, second recombination event must occur by a strand-switching event into the 3' replication recognition sequence of the recombinant replicon intermediate (described above), since this is the only location that would result in retention of functional transcriptional units for all of the nonstructural and structural protein coding sequences without insertional mutagenesis. Because the helper RNA molecules contain 26S promoters, two such recombination events could create, theoretically, an RCV. The precise recombination points would not be critical because each of the recombination inserts would be an independent transcriptional unit.

Generation of RCV using promoterless helper molecules of this invention would also require a minimum of two independent recombination events, but the constraints for obtaining a functional recombinant are much higher than for the RNA helper molecules known in the literature and thus the theoretical frequency for generating RCV is much lower. This is because, in the absence of the 26S promoter, most recombination events would not result in the generation of a functional transcriptional unit that could express an alphavirus structural protein. Thus, the generation of RCV using promoterless helper molecules will require the regeneration of a structural polyprotein open reading frame (i.e., substantively similar to the structure found in the wild-type virus from which these helpers are derived), and this in turn requires that the two required recombination events occur in a specific order and in very specific nucleotide locations. The initial recombination event must involve the capsid helper coding sequence, since it must be located in a proper (i.e., 5') position relative to the glycoproteins in order to cleave itself and generate a functional capsid protein. The capsid helper must be recombined with the replicon vector via a nucleotide- or near-nucleotide-perfect recombination event to achieve a recombinant in which there would be expression of the capsid protein from the replicon 26S promoter. That is, only recombinations that 1) are directly downstream of the replicon 26S promoter, 2) are in frame with any remnants of the heterologous GOI, and 3) do not result in the generation of a GOI/alphavirus capsid fusion protein (thereby generating an inactive alphavirus capsid), would be functional. The second recombination event, involving the alphavirus glycoprotein helper, is under the same constraints as the first, in addition to being limited to occurring in the 3' replication recognition sequence. Thus, methods of this invention for producing the particles using the promoterless helper molecules will theoretically generate RCV at a much lower frequency than the helper molecules known in the literature, a frequency so low that no such RCV have been detected with the methods of this invention.

The surprising nature of this invention lies in the fact that previous efforts to produce helper/replicon systems for assembling alphavirus particles have relied on the use of a strong promoter, most often the alphavirus 26S subgenomic promoter, to provide sufficient RNA molecules from which to translate structural proteins for assembly. In stark contrast to the existing literature, the inventors discovered that they can utilize novel RNA helper molecules that can be translated directly as full length molecules without transcription of smaller messenger RNAs from the 26S promoter and the messenger amplification that normally accompanies this process in wild-type alphavirus propagation and helper RNA systems known in the literature. Direct translation of the helper RNAs of this invention is then accomplished through the recognition of the cap at the 5' end of the full-length RNA by cellular ribosomal machinery. Within a eukaryotic cell, the initiation of translation from an mRNA involves a series of tightly regulated events that allow the recruitment of ribosomal subunits to the mRNA. In the case of cap-dependent translation, the methyl-7-G(5')pppN structure present at the 5' end of the mRNA, known as "cap," is recognized by the cellular initiation factor eIF4F, which is composed of eIF4E, eIF4G and eIF4A. (reviewed in Hershey & Merrick. *Translational Control of Gene Expression*, pp. 33-88. Cold Spring Harbor, N.Y.: Cold Spring Harbor Laboratory Press. 2000.)

Alphaviruses are positive strand RNA viruses; when the viral RNA enters the cell, translation of the nonstructural alphavirus proteins (nsP1, nsP2, nsP3 and nsP4) occurs from this RNA, and these proteins generate a full-length negative strand RNA template, respectively. The negative strand RNA is then replicated to produce a full-length ("genomic") positive strand RNA and a smaller ("subgenomic") positive strand that is initiated at the 26S promoter. When the positive strands are produced, the nonstructural proteins of the alphavirus also cap the RNA, making it available in the cytoplasm for translation by ribosomes. The "cap" refers to a methylated residue added to the 5' end of the RNA. In specific embodiments of this invention, the helper RNA molecules that are produced in vitro (which are positive strand RNAs) are not capped. When the positive strand helper RNAs are introduced into a eukaryotic cell also containing a replicon RNA, largely negative strand synthesis occurs initially. In the presence of the alphavirus replicon RNA, from which the non-structural proteins are synthesized, the negative strand templates (both helper and replicon) will be replicated into positive strand RNAs that are then capped. In other embodiments of this invention, the helper RNAs can be capped in vitro, using reagents well known to the art and commercially available, for example, from Promega (Madison, Wis.) and Ambion (Austin, Tex.). Caps can include G cap, C cap, A cap, methylated G ($m^7$G(5' ppp(5')pppG(5)A); unmethylated G(G(5' ppp(5')A); ARCA (anti-reverse cap analog, 3-O-Me-$m^7$G(5') pppG(5)); trimethylated ($m^2$, $^{2,7}$G(5' ppp(5')pppG), 2-way cap ($m^7$G(5' ppp(5')$m^7$G), for example. In some embodiments, for maximal yield of ARP, all helpers of this invention used to produce ARP are either capped or uncapped. Highest yields have been recorded with capped helper RNAs, but, in certain embodiments, uncapped helper RNAs can generate sufficiently high yields such that the added cost of capping may be avoided. It is also possible to cap only one of the helper RNAs, although this also may sometimes limit ARP yields. In general, the inventors have shown that ARP yield can be optimized by routine experimentation looking at several variables, such as varying the use of capping, the ratio of cap analog to NTPs in the transcription mixture, and the ratio of RNAs used to generate the ARPs.

Thus, in particular embodiments, the present invention provides an isolated RNA molecule comprising, consisting essentially of and/or consisting of: a) an alphavirus 5' replication recognition sequence wherein at least one initiation codon has been removed; b) a nucleotide sequence encoding an alphavirus structural protein; and c) an alphavirus 3' replication recognition sequence, with the proviso that the RNA molecule does not contain a promoter that directs transcription of the nucleotide sequence of (b), and wherein the alphavirus 5' and 3' replication recognition sequences direct replication of the entire RNA molecule in the presence of alphavirus nonstructural proteins.

A wide variety of nucleic acid sequences can satisfy the function of the 5' and 3' ends in the nucleic acid constructs of this invention. For example, the sequence can include the alphavirus 5' replication recognition sequence and other adjacent sequences, as exemplified above, for the VEE alphavirus. Additionally, deletions can be made in the native 5' alphavirus end to remove certain secondary structural elements, for example stem-loop structures. In certain embodiments, one or more of these stem-loop structures may be removed from the helper constructs of this invention. Alternatively, non-alphavirus or other sequences can be employed as this element, while maintaining similar functional capacity, for example, in the case of Sindbis virus, nucleotides 10-75 for tRNA asparagine (Schlesinger et al. U.S. Pat. No. 5,091,309).

In some embodiments, the 3' alphavirus replication recognition sequence can be approximately 300 nucleotides in length, which contains essentially the native alphavirus 3' replication recognition sequence. The minimal 3' replication recognition sequence, conserved among alphaviruses, is a 19 nucleotide sequence (Hill et al., *Journal of Virology*, 2693-2704 (1997)). In addition, for Sindbis virus, it has been shown that the poly(A) tail immediately following the 3' replication recognition sequence must be at least 11-12 residues in length and that the 3' 13 nt of the 3' replication recognition sequence are critical for efficient minus strand RNA synthesis (Hardy and Rice, *Journal of Virology*, 79:4630-4639 (2005)). Therefore, sequence for the 3' end can include a complete alphavirus 3' replication recognition sequence, or a truncated region of the 3' replication recognition sequence, which still maintains function as a recognition sequence, or a 3' end that is between 25 and 325 nucleotides in length and contains a poly(A) run immediately following the 3' replication recognition sequence with a minimum length of 11-12 nt. Other examples of sequences that can be used in this context include, but are not limited to, non-alphavirus or other sequences that maintain a similar functional capacity to permit initiation of negative strand RNA synthesis (e.g., sequences described in George et al. *J. Virol.* 74: 9776-9785 (2000)).

The 5' and 3' replication recognition sequences used in the RNA molecules of this invention can be derived from the same or different alphaviruses in any combination, and they can be used in any combination with replicon vectors which are derived from the same or different alphaviruses.

In certain embodiments of this invention, the 5' and 3' sequences of the helper RNA molecules are chosen to both maximize the performance of the helpers in generating VRPs and minimize the theoretical potential for generating RCV. Specific embodiments may include modifications of the 5' and 3' sequences as well as deletions of parts of the original 5' and 3' sequences from the alphavirus, examples of which are described herein. There are numerous combinations of 5' and 3' sequences described in this invention, and different combinations can be used for each helper molecule. It is within one of skill in the art to test various combinations of the modifications and deletions taught herein to determine their performance in the generation of VRPs.

The RNA helper molecules of this invention rely on ribosomes scanning from the 5' cap structure through the 5' replication recognition sequence to initiate translation of the alphavirus structural proteins at their native methionine start codon. The presence of additional initiation codons in these regions reduces the effectiveness of these helpers by allowing translation to initiate at a site other than the native start codon for the structural proteins, thereby generating either fusion proteins as the ribosomes move along the mRNA into the alphavirus structural protein coding region or short non-functional peptides when the ribosomes subsequently reach a stop codon in the 5' replication recognition sequence. Therefore, the use of the intact 5' alphavirus non-coding region in these helpers (i.e., the entire sequence from the 5' terminus of the wild-type alphavirus up to the first codon of the 26S subgenomic promoter) is not optimal, due to the presence of numerous start and stop codons in this region. Thus, in particular embodiments, the RNA molecules of this invention can have one or more initiation codons removed from the 5' replication recognition sequence. By one or more is meant that two, three, four, five, six, seven, eight, nine, ten, 11, 12 or more initiation codons (i.e., start codons) have been removed or inactivated according to methods standard in the art.

Thus, the present invention provides an RNA molecule of this invention wherein one or more initiation codons have been removed, e.g., by mutation from AUG to GUG, from the 5' replication recognition sequence. In a specific embodiment, an RNA molecule is provided wherein all initiation codons have been removed, e.g., by mutation from AUG to GUG, from the 5' replication recognition sequence. For example, one or more initiation codons in any combination at the following positions as shown in FIG. 1 can be removed, e.g., mutated: 12, 45, 148, 154, 160, 258, 294, 299, 331, 390, 411, 441 and 499.

By removal of an initiation codon it is meant that the nucleotide sequence is modified (e.g., according to methods described herein and as known in the art) to delete or change the initiation codon, thereby removing or altering initiation or activity (e.g., translation activity) at that site. In some embodiments, a majority of the initiation codons can be removed, but it is possible that only a few of such codons in the 5' region of a particular helper construct are in a context that is typically recognized by a ribosome. Thus, for specific 5' sequences, removal of 2-3 such codons, out of a possible 10-12 codons, may result in expression levels that are not significantly different than a construct in which all 10-12 codons have been removed. It is within the scope of this invention that there are a numerous specific 5' sequences, derived from the wild-type alphavirus sequences, that when used in the helper molecules of this invention, will result in sufficient expression within the packaging or helper cell to provide acceptable yields of alphavirus replicon particles.

The RNA molecule of this invention can comprise a nucleotide sequence encoding 1) an alphavirus capsid protein, 2) alphavirus E1 and E2 proteins in any order, 3) alphavirus capsid protein and alphavirus E1 protein in any order, 4) alphavirus capsid protein and alphavirus E2 protein in any order, 5) alphavirus E2 protein, and/or 6) alphavirus E1 protein. In other embodiments, a single RNA molecule of this invention can encode the three alphavirus structural proteins, i.e., capsid protein, alphavirus E1 protein and alphavirus E2 protein, in any order. In some embodiments, the RNA molecule of this invention can specifically exclude a nucleotide sequence encoding an alphavirus structural protein (e.g., the molecule can specifically exclude a nucleotide sequence encoding capsid, alphavirus E1 protein, alphavirus E2 protein or any combination of capsid, E1 protein and E2 protein).

In various embodiments of this invention, the RNA molecule can comprise sequence from the 5' end of Venezuelan equine encephalitis (VEE) virus, which includes a 5' replication recognition sequence. As described by Pushko et al. (1997), the 5' replication recognition sequence of VEE promoter-assisted helpers typically consists of 575 nucleotides (nt) of VEE sequence. The first 519 are contiguous and represent the 44 nt untranslated region (UTR) and the first 475 nt of nsP1 (44+475=519). The remaining 56 nt encode the last 21 nt of the nsP4 gene (including the TAA stop codon), 7 nt of the minimal 26S promoter (whose sequence partially overlaps the nsP4 gene) and a 28 nt leader sequence upstream of the VEE structural protein gene initiation codon (21+7+28=56).

Thus, the complete 5' replication recognition sequence for the promoter-assisted helpers described by Pushko et al. (1997) consist of 575 nt of VEE sequence. The promoterless helpers of this invention encode all or a portion of the first 514 nucleotides (nt) found in the promoter-assisted helpers described above. In addition to the 514 nt described above, sequence encoding an RsrII restriction enzyme site (7 nt) is also present just upstream of the structural protein coding sequence start site (ATG in DNA; AUG in RNA). Inclusion of these nt increases the 5' replication recognition sequence for the full length capsid helper (dHcap(FL) to 521 nt (not including the A residue of the initiation codon).

In some examples of the promoterless capsid helpers and all examples with promoterless glycoprotein helpers, an additional modification to include a near-consensus Kozak sequence (3 nt (ACC)) just upstream of the structural protein coding sequence initiation codon but downstream of the RsrII sequence have been added. Because of the Kozak modification the full length glycoprotein helper (dHgp(FL) has a 5' replication recognition sequence of 524 nt. With these nucleotide sequences defined for the promoterless capsid and glycoprotein helpers as the "full length" ("FL") 5' VEE sequence for the purposes of the following description, deletions in this sequence result in other embodiments that encompass the 5' replication recognition sequence. These embodiments include nucleotides 1 through 141 (not including the A residue of the initiation codon) of the VEE nucleotide sequence, at a minimum. Within the first 200 nucleotides of the 5' sequence, four stem-loop (SL) structures in the RNA are predicted.

Embodiments of the 5' sequence useful in the helper constructs of this invention may include 1, 2, 3 or all of the SL structures in this region. Embodiments that remove the SL2 region, and retain the SL1, SL3 and SL4 structures, are useful in the helper constructs of this invention. SL structures 1 and 2 are contained in the first 145 nucleotides; SL 3 and 4 are present between nucleotides 145 and 200. Thus, in some embodiments, the 5' replication recognition sequence is included in a 5' non-coding region of the construct which is 524 nucleotides in length (e.g., dHgp(FL) in FIG. 2) and in other embodiments, the 5' replication recognition sequence can be included in a 5' non-coding region that is anywhere from 70 (e.g., containing SL1, SL3 and SL4) to 524 nucleotides in length. For example, the 5' replication recognition sequence can be 141, 144 (dH #8) 200, 203 (dH #7), 248, 249 (dH #6), 309, 312 (dH #5), 351, 354 (dH #4), 412, 415 (dH #3) 450, 452 (dH #2), 499 or 502 (dH #1) nucleotides in length, including any number between 70 and 524 not specifically recited herein (e.g., 237, 379, 444, etc.). It should be noted that the exact nucleotide number and length varies somewhat between different alphaviruses and between different strains of a given alphavirus. It is well within the ability of one skilled in the art to identify the corresponding locations of the nucleotides described herein based on corresponding structure and/or function and/or of the secondary structures described herein in any alphavirus and create the RNA helper molecules of this invention as well as the above-described modifications from the primary nucleotide sequence of any alphavirus.

The RNA helper molecules of this invention also comprise sequence from the 3' end of an alphavirus, which in particular embodiments, can be, but is not limited to the Venezuelan equine encephalitis virus, which includes the alphavirus 3' replication recognition sequence. The 3' terminal 19 nucleotides of all alphaviruses are highly conserved, while the 3' sequence between the last codon of the E1 glycoprotein and the highly conserved 19 nucleotides is less conserved, both in terms of length and sequence among alphaviruses. The length of the 3' non-coding region (including the conserved 19 nucleotides, herein SEQ ID NO:52) can range from 25 to 325 nucleotides. In specific embodiments of this invention, the 3' sequence is between 73 to 117 nucleotides of the VEE 3' end. In particular embodiments, alphavirus 3' replication recognition sequence of this invention can comprise, consist essentially of and/or consist of the nucleotide sequence of SEQ ID NO:55 (for dHcap(FL) through dHcap7; dHcap(FL)mm through dHcap7 mm, dHcap(FL)mut1 through dHcap7-mut1), SEQ ID NO:56 (for Hgp(FL) through dHgp7, dHgp (FL)mm through dHgp7-mm, dHgp(FL)mut1 through dHgp7-mut1), SEQ ID NO:57 (for dHcap6mut1(w/stop), SEQ ID NO:58 (for dHcap7mut1(w/stop)+19 nt and dHgp7mut1-S+19 nt), and SEQ ID NO:59 (dHcap6mut1(W-stop).

In particular embodiments, the alphavirus 5' replication recognition sequence of this invention can comprise, consist essentially of and/or consist of the nucleotide sequence of SEQ ID NO:1 (dHcap(FL)), SEQ ID NO:2 (dHcap1), SEQ ID NO:3 (dHcap2), SEQ ID NO:4 (dHcap3), SEQ ID NO:5 (dHcap4), SEQ ID NO:6 (dHcap5), SEQ ID NO:7 (dHcap6), SEQ ID NO:8 (dHcap7), SEQ ID NO:9 (dHcap8), SEQ ID NO:10 (dHgp(FL), SEQ ID NO:11 (dHgp1), SEQ ID NO:12 (dHgp2), SEQ ID NO:13 (dHgp3), SEQ ID NO:14 (dHgp4), SEQ ID NO:15 (dHgp5), SEQ ID NO:16 (dHgp6), SEQ ID NO:17 (dHgp7), SEQ ID NO:18 (dHgp8), SEQ ID NO:19 (dHcap(FL)-mm), SEQ ID NO:20 (dHcap1-mm), SEQ ID NO:21 (dHcap2-mm), SEQ ID NO:22 (dHcap3-mm), SEQ ID NO:23 (dHcap-4-mm), SEQ ID NO:24 (dHcap5-mm), SEQ ID NO:25 (dHcap6-mm), SEQ ID NO:26 (dHcap7-mm), SEQ ID NO:27 (dHgp(FL)-mm), SEQ ID NO:28 (dHgp1-mm), SEQ ID NO:29 (dHgp2-mm), SEQ ID NO:30 (dHgp3-mm), SEQ ID NO:31 (dHgp-4-mm), SEQ ID NO:32 (dHgp5-mm), SEQ ID NO:33 (dHgp6-mm), SEQ ID NO:34 (dHgp7-mm), SEQ ID NO:35 (dHcap(FL)mut1), SEQ ID NO:36 (dHcap1mut1), SEQ ID NO:37 (dHcap2 mut1), SEQ ID NO:38 (dHcap3 mut1), SEQ ID NO:39 (dHcap4 mut1), SEQ ID NO:40 (dHcap5 mut1), SEQ ID NO:41 (dHcap6 mut1), SEQ ID NO:42 (dHcap7 mut1), SEQ ID NO:43 (dHgp (FL)mut1), SEQ ID NO:44 (dHgp1 mut1), SEQ ID NO:45 (dHgp2 mut1), SEQ ID NO:46 (dHgp3 mut1), SEQ ID NO:47 (dHgp4 mut1), SEQ ID NO:48 (dHgp5 mut1), SEQ ID NO:49 (dHgp6 mut1), SEQ ID NO:50 (dHgp7 mut1), SEQ ID NO:51 (dHcap6-mut1-dSL2), SEQ ID NO:52 (dHgp6-mut1-dSL2(-S)); SEQ ID NO:53 (dHcapU); and SEQ ID NO:54 (dHgpU). The specific helper for which these 5' sequence examples have been synthesized is given in parentheses. The sequences can vary slightly in length due to the use of additional nucleotides to provide a near-optimal Kozak consensus sequence to enhance translation of the structural protein coding sequence in some of the helper constructs. (The ATG (AUG in RNA) of the coding region for the structural protein coding sequence is not included in these 5' sequences). RNA molecules of this invention comprising the nucleotide sequences identified above can be employed in the methods of this invention for production of alphavirus replicon particles in any combination, in any order and/or in any multiplicity.

The present invention additionally provides a vector and/or a nucleic acid construct comprising the RNA molecule of this invention. Further provided is a cell comprising one or more RNA molecules of this invention and one or more alphavirus replicon vectors. By one or more is meant one, two, three, four, five, six, seven, etc. A cell of this invention is any cell in which nucleic acid constructs encoding alphavirus proteins can be expressed. Examples of cells of this invention include, but are not limited to, Vero, baby hamster kidney (BHK), 293, 293T/17 (ATCC accession number CRL-11268), chicken embryo fibroblast (CEF), UMNSAH/DF-1 (ATCC accession number CRL-12203), PERC.6 and Chinese hamster ovary (CHO) cells.

Further provided herein is a method of making an alphavirus replicon particle, comprising introducing one or more of the RNA molecules of this invention into a cell, whereby the combination of RNA molecules encodes all alphavirus structural proteins necessary for production of an alphavirus replicon particle, along with an alphavirus replicon RNA, under conditions whereby alphavirus replicon particles are produced. In some embodiments of this invention, the alphavirus particle mimics the structural make-up of the native alphavirus, in which the replicon RNA is coated with the capsid protein and then enveloped with cell membrane containing the alphavirus glycoproteins. In such embodiments, the alphavirus structural proteins are all from the same alphavirus. In alternative embodiments, the alphavirus proteins can be from different alphaviruses, provided that these different proteins "recognize" each other during particle assembly or that they are modified (as described in the literature) so that they will be able to recognize each other.

In some embodiments of the methods of this invention, two RNA molecules of this invention are introduced into a cell of this invention, wherein the two RNA molecules encode different alphavirus structural proteins in a combination whereby all the necessary structural proteins are produced in the packaging cell to produce alphavirus replicon particles. Thus, the present invention provides a method wherein two RNA molecules are introduced into the cell and wherein a first RNA molecule of the two RNA molecules encodes one or more alphavirus structural proteins but not all of the structural proteins and a second RNA molecule of the two RNA molecules encodes one or more alphavirus structural proteins that are not encoded by the first RNA molecule.

Also provided is a method wherein three RNA molecules of this invention are introduced into a cell, wherein the three RNA molecules each encode a different alphavirus structural protein, in a combination whereby all of the necessary structural proteins are produced in the cell to produce alphavirus replicon particles. Thus, a method is provided, wherein three of the RNA molecules of this invention are introduced into the cell, wherein a first RNA molecule of the three RNA molecules encodes one or more alphavirus structural proteins but not all of the structural proteins and a second RNA molecule of the three RNA molecules encodes one or more alphavirus structural proteins that are different from the alphavirus structural proteins encoded by the first RNA molecule and a third RNA molecule of the three RNA molecules encodes one or more alphavirus structural proteins that are different from the alphavirus structural proteins encoded by the first RNA molecule and the second RNA molecule. For example, in one embodiment, the first RNA molecule can encode alphavirus capsid protein, the second RNA molecule can encode alphavirus glycoprotein E1 and the third RNA molecule can encode alphavirus glycoprotein E2.

In some embodiments, one or more, but not all, of the alphavirus structural proteins can be encoded by the replicon RNA that is packaged by the alphavirus structural proteins. For example, a recombinant RNA used in the methods of making alphavirus replicon particles claimed herein can comprise, as a nucleic acid of interest and/or in addition to a nucleic acid of interest, a nucleic acid sequence encoding one alphavirus structural protein or more than one alphavirus structural protein. Thus, in a specific embodiment, a replicon RNA encodes an alphavirus structural protein or more than one alphavirus structural protein. This replicon RNA can be introduced into a population of cells together with one or more RNA helper molecules of this invention, such that the replicon RNA and the RNA helper molecules(s) produce all of the alphavirus structural proteins, and the replicon RNA is packaged into particles in said cells.

In further embodiments, a method is provided for making an alphavirus replicon particle, comprising introducing into a cell: a) an alphavirus replicon RNA; b) one or more RNA molecules of this invention; and c) one or more promoter-assisted alphavirus helper constructs, whereby the combination of RNA molecules of (b) and helper constructs of (c) encodes all alphavirus structural proteins necessary for production of an alphavirus replicon particle, under conditions whereby an alphavirus replicon particle is produced.

Thus, in additional embodiments of this invention, "promoter-assisted helper constructs," i.e., recombinant DNA or RNA molecules that express one or more alphavirus structural proteins under the direction of a promoter, e.g., the 26S promoter, are used in combination with the helper molecules of this invention. In one set of RNA molecule embodiments, the "promoter-assisted helper construct" comprises a first nucleic acid sequence encoding (i) a 5' alphavirus replication recognition sequence, (ii) a transcriptional promoter, (iii) a nucleic acid sequence encoding one or more alphavirus structural proteins, and (iv) a 3' alphavirus replication recognition sequence.

In another set of RNA molecule embodiments, the "promoter-assisted helper construct" is a recombinant helper nucleic acid, as described in WO 2004/085660 (published Oct. 7, 2004 and incorporated herein by reference), comprising: a nucleic acid sequence encoding a 5' alphavirus replication recognition sequence, an alphavirus subgenomic promoter immediately upstream of an IRES element, at least one nucleic acid encoding an alphavirus structural protein, and a nucleic acid encoding a 3' alphavirus replication recognition sequence. In further embodiments, these promoter-assisted helper constructs can comprise a spacer nucleic acid located immediately downstream of the subgenomic promoter and immediately upstream of the IRES element. The spacer nucleic acid can comprise or consist of any random or specific non-coding nucleic acid sequence that is of a length sufficient to prevent at least some, and in some embodiments, all translation from the 5' cap of a messenger RNA, such that translation of the structural proteins is then directed by the IRES, in part or in whole. Alternatively, the spacer nucleic acid can be of a length and sequence structure that imparts sufficient secondary structure to the nucleic acid to prevent at least some and possibly all translation activity from the 5' cap of a messenger RNA. The promoter-assisted helper constructs used in this invention can also be DNA molecules, which can be stably integrated into the genome of the helper cell or transiently expressed from an episome (e.g., a plasmid) without significant integration. The DNA molecule of this invention can be any DNA vector, including but not limited to, a non-integrating DNA vector, such as a plasmid, or a viral vector.

In embodiments of this invention employing "helper cells" or "packaging cells" as described herein, and comprising a promoterless RNA molecule of this invention, the helper cell can further comprise a promoter-assisted helper construct (RNA and/or DNA) in any combination such that the helper cell comprises a combination of nucleotide sequences encoding alphavirus structural proteins sufficient to produce an alphavirus replicon particle of this invention. In certain embodiments, the E1 and E2 glycoproteins are encoded by a first helper construct, and the capsid protein is encoded by a second helper construct. In another embodiment, the E1 glycoprotein, E2 glycoprotein, and capsid protein are each encoded by separate (e.g., first, second and third) helper constructs. In yet other embodiments, the capsid protein and either glycoprotein E1 or E2 are encoded by a first helper construct, and the remaining glycoprotein E1 or E2 not included in the first helper construct is encoded by a second helper construct, with or without the capsid coding sequence. In additional embodiments, alphavirus glycoproteins E1 and E2, as well as capsid protein can all be encoded on one helper construct, in any order and/or in any multiplicity. Among the embodiments included in this invention, it is also possible that a given alphavirus structural protein is expressed by more than one helper construct. The promoterless RNA helpers of this invention, optionally in combination with other known helpers as described herein, can be introduced into an alphavirus-permissive cell in any combination, in any order and/or in any multiplicity.

In some embodiments of this invention (e.g., for DNA constructs encoding promoterless RNA molecules or promoter-assisted RNA helper constructs), a promoter for directing transcription of RNA from DNA, i.e., a DNA dependent RNA polymerase is utilized to synthesize RNA in an in vitro transcription reaction, and specific promoters suitable for this use include, but are not limited to, the SP6, T7, and T3 RNA polymerase promoters.

In all of the embodiments of this invention, it is contemplated that at least one of the alphavirus structural and/or non-structural proteins encoded by the promoterless helper molecules and/or promoter-assisted helper constructs and/or the replicon vector, as well as the nontranslated regions of the replicon nucleic acid, can contain one or more attenuating mutations, as described herein, in any combination.

The present invention further provides a population of alphavirus replicon particles, wherein the population contains fewer than one replication-competent alphavirus particle per $10^8$ alphavirus replicon particles. In further embodiments, the population contains fewer than one replication-competent alphavirus particle per $10^9$, $10^{10}$, $10^{11}$, $10^{12}$ or $10^{13}$ alphavirus replicon particles. The present invention additionally provides a population of alphavirus replicon particles, wherein the population contains no detectable replication-competent virus particles, as determined by passage on permissive cells in culture according to methods well known in the art.

Also provided herein is a population of alphavirus replicon particles, wherein the population contains no detectable or fewer than one replication-competent alphavirus particle per $10^8$, $10^9$, $10^{10}$, $10^{11}$, $10^{12}$ or $10^{13}$ alphavirus replicon particles, as determined by passage on permissive cells in culture, wherein the alphavirus replicon particles comprise one or more attenuating mutations in either an alphavirus structural protein or an alphavirus nonstructural protein or both an alphavirus structural protein and an alphavirus nonstructural protein. Additionally provided is a population of alphavirus replicon particles, wherein the population contains no detectable replication-competent virus particles, as determined by passage on permissive cells in culture, wherein the alphavirus replicon particles comprise one or more attenuating mutations in either an alphavirus structural protein or an alphavirus nonstructural protein or both an alphavirus structural protein and an alphavirus nonstructural protein.

It has been confirmed by the inventors that, despite the lack of an identifiable "packaging signal," helper RNAs of this invention, as well as helper RNAs described in the literature, are packaged by the alphavirus structural proteins in the cultured cells, sometimes at a frequency that is considerably higher than that reported in the literature. Thus, the population of alphavirus replicon particles of this invention is distinguished from those particles described in the literature by the presence of a subset of particles in the population in which are packaged the novel helper molecules of this invention.

The terms "alphavirus replicon particles," "ARPs," "virus replicon particles" or "recombinant alphavirus particles," used interchangeably herein, mean a virion-like structural complex incorporating an alphavirus replicon RNA that expresses one or more heterologous RNA sequences. Typically, the virion-like structural complex includes one or more alphavirus structural proteins embedded in a lipid envelope enclosing a nucleocapsid that in turn encloses the RNA. The lipid envelope is typically derived from the plasma membrane of the cell in which the particles are produced. In certain embodiments, the alphavirus replicon RNA is surrounded by a nucleocapsid structure comprised of the alphavirus capsid protein, and the alphavirus glycoproteins are embedded in the cell-derived lipid envelope. The structural proteins and replicon RNA may be derived from the same or different alphaviruses. In a specific embodiment, the replicon RNA is derived from VEE and the structural proteins are derived from Sindbis virus (see, e.g., Dubensky et al., U.S. Pat. No. 6,376,236). The alphavirus replicon particles are infectious but propagation-defective, i.e., the replicon RNA cannot propagate beyond the host cell that the particles initially infect, in the absence of the helper nucleic acid(s) encoding the alphavirus structural proteins.

The terms "alphavirus RNA replicon," "alphavirus replicon RNA," "alphavirus RNA vector replicon," and "vector replicon RNA" are used interchangeably to refer to an RNA molecule expressing nonstructural protein genes such that it can direct its own replication (amplification) and comprises, at a minimum, 5' and 3' alphavirus replication recognition sequences (which may be the minimal sequences, as defined above, but may alternatively be the entire regions from the alphavirus), coding sequences for alphavirus nonstructural proteins, and a polyadenylation tract. It may additionally contain a promoter and/or an IRES. It may also be engineered to express alphavirus structural proteins. Johnston et al. and Polo et al. describe numerous constructs for such alphavirus RNA replicons, and such constructs are incorporated herein by reference. In one embodiment of the alphavirus replicon RNA, the alphavirus nonstructural proteins are separated into two separate translational units, as described in U.S. Patent Publication 2003-0119182-A1, incorporated herein by reference.

An alphavirus replicon RNA with no heterologous sequences, i.e., an empty replicon, can be used in an alphavirus replicon particle to produce an adjuvant composition. Alternatively, the alphavirus replicon RNA can express nucleic acid encoding alphavirus structural proteins and/or other heterologous nucleic acid sequences, the latter of which can be chosen from a wide variety of sequences derived from viruses, prokaryotes and/or eukaryotes. Examples of categories of heterologous sequences include, but are not limited to, immunogens (including native, modified or synthetic antigenic proteins, peptides, immunogenic fragments, or epitopes), cytokines, toxins, therapeutic proteins, enzymes, antisense sequences, and immune response modulators. If appropriate and desired for the particular application, the transcribed mRNA is then translated, i.e., protein is synthesized or a functional RNA is produced. These mRNAs are "capped" within the eukaryotic cell, i.e., a methyl-7-guanosine (5')pppN structure is present at the 5' end of the mRNA (the "cap" or "5' cap"), and this cap is recognized by the translation initiation factors that synthesize protein from the mRNA. Thus, the 26S promoter directs transcription, and the "cap" provides the initiation signal for translation.

In some embodiments, the replicon RNA can lack nucleic acid encoding any alphavirus structural protein(s). In other embodiments, the alphavirus replicon RNA can comprise nucleic acid encoding one or two alphavirus structural proteins, but the replicon RNA does not contain nucleic acid encoding all of the alphavirus structural proteins. Thus, the resulting alphavirus replicon particles of this invention are propagation-defective inasmuch as the replicon RNA does not encode all of the structural proteins required for encapsidation of the replicon RNA and assembly of an infectious virion.

Specific embodiments of the alphavirus RNA replicons utilized in the claimed invention can contain one or more attenuating mutations as described in detail herein, Examples of an attenuating nucleotide substitution include the mutation at nucleotide 3 in the VEE 5' end described herein and a mutation at nsP1 amino acid position 538, nsP2 amino acid position 96, or nsP2 amino acid position 372 in the alphavirus S.A.AR86.

The alphavirus replicon particles of this invention can comprise replicon RNA from any alphavirus. Furthermore, the alphavirus replicon particles of this invention can comprise alphavirus structural proteins from any of the alphaviruses of this invention. Thus, the replicon particles can be made up of replicon RNA and structural proteins from the same alphavirus or from different alphaviruses, the latter of which would be chimeric alphavirus replicon particles (e.g., a particle comprising VEE virus-based replicon RNA and Sindbis virus structural proteins).

In particular embodiments of the present invention, the alphavirus structural protein of this invention can be a Sindbis virus structural protein, a SFV structural protein, a VEE structural protein, a Ross River virus structural protein, an EEE structural protein and/or a WEE structural protein. These can be present in any combination with one another and can be present in combination with nonstructural proteins and other alphaviral sequences, such as the 5' alphavirus replication recognition sequence, the alphavirus subgenomic promoter and the 3' alphavirus replication recognition sequence, from any of these or other alphaviruses, to produce chimeric recombinant alphavirus replicon particles and/or chimeric recombinant nucleic acids of this invention.

In some embodiments of this invention, the present invention can include alphavirus nucleic acids, alphavirus proteins, alphavirus replicon RNA and/or alphavirus replicon particles including one or more attenuating mutations, an attenuating mutation being defined as a nucleotide deletion, addition, and/or substitution of one or more nucleotide(s), or a mutation that comprises rearrangement or chimeric construction, which results in a loss of virulence in a live virus containing the mutation as compared to the appropriate wild-type alphavirus.

Appropriate attenuating mutations will be dependent upon the alphavirus used, and will be known to those skilled in the art. Exemplary attenuating mutations include, but are not limited to, those described in U.S. Pat. No. 5,505,947 to Johnston et al., U.S. Pat. No. 5,185,440 to Johnston et al., U.S. Pat. No. 5,643,576 to Davis et al., U.S. Pat. Nos. 5,792,462; 6,156,558 and 5,639,650 to Johnston et al., the disclosures of each of which are incorporated herein in their entireties by reference.

Specific attenuating mutations for the VEE E1 glycoprotein can include an attenuating mutation at any one of E1 amino acid positions 81, 272 or 253. Alphavirus replicon particles made from the VEE-3042 mutant contain an isoleucine substitution at E1-81, and virus replicon particles made from the VEE-3040 mutant contain an attenuating mutation at E1-253. Specific attenuating mutations for the VEE E2 glycoprotein can include an attenuating mutation at any one of E2 amino acid positions 76, 120, or 209. Alphavirus replicon particles made from the VEE-3014 mutant contain attenuating mutations at both E1-272 and at E2-209 (see U.S. Pat. No. 5,792,492). A specific attenuating mutation for the VEE E3 glycoprotein includes an attenuating mutation consisting of a deletion of E3 amino acids 56-59. Virus replicon particles made from the VEE-3526 mutant contain this deletion in E3 (aa56-59) as well as a second attenuating mutation at E1-253. Specific attenuating mutations for the S.A.AR86E2 glycoprotein include an attenuating mutation at any one of E2 amino acid positions 304, 314, 372, or 376. Alternatively, the attenuating mutation can be a substitution, deletion or insertion of an amino acid in the E2 glycoprotein, for example, at any one or more of the following amino acid positions in any combination: 158, 159, 160, 161 and 162 (see Polo et al., PCT Publication No. WO 00/61772). Alternatively, the RNA molecules of this invention can be derived from TC83, a vaccine strain of VEE (see WO 2005/113782, which is incorporated herein by reference).

Another attenuating mutation of this invention can be an attenuating mutation at nucleotide 3 of the VEE genomic RNA, i.e., the third nucleotide following the 5' methylated cap (see, e.g., U.S. Pat. No. 5,643,576 describing a G→C mutation at nt 3). This mutation, located in a non-coding sequence of the virus or replicon, can be a G→A or a G→U mutation in some embodiments. When the alphavirus structural and/or non-structural proteins are from S.A.AR86, exemplary attenuating mutations in the structural and non-structural proteins have been described in the literature (see, e.g., U.S. Pat. No. 5,639,650 and U.S. Pat. No. 6,982,087, the disclosures of which are incorporated herein in their entirety by reference).

The alphavirus of this invention can be a Sindbis virus strain (e.g., TR339), VEE (e.g., having a mutation at nucleotide 3 of the genomic RNA following the methylated cap or TC83), S.A.AR86 virus, Girdwood S.A. virus, Ockelbo virus, and/or chimeric viruses thereof. The complete genomic sequences, as well as the sequences of the various structural and non-structural proteins are available in the literature for numerous alphaviruses and include: Sindbis virus genomic sequence (GenBank Accession Nos. J02363, NCBI Accession No. NC_001547), S.A.AR86 genomic sequence (GenBank Accession No. U38305), VEE genomic sequence (Gen- Bank Accession No. L04653, NCBI Accession No. NC_001449), TC-83 vaccine strain of VEE (Kinney R M et al. (1989) *Virology* 170:19-30; with correction noted in Kinney R M et al. (1993) *J. Virol.* 67(3):1269-1277); Girdwood S.A genomic sequence (GenBank Accession No. U38304), Semliki Forest virus genomic sequence (GenBank Accession No. X04129, NCBI Accession No. NC_003215), and the TR339 genomic sequence (Klimstra et al., (1988) *J. Virol.* 72:7357; McKnight et al. (1996) *J. Virol.* 70:1981).

Alphavirus replicon particles are prepared according to the methods disclosed herein in combination with techniques known to those skilled in the art. The methods include first introducing the selected helper(s) and an alphavirus replicon RNA into a population of alphavirus-permissive cells, and then incubating the cells under conditions well known in the art that allow for the production of alphavirus replicon particles. The step of introducing the helper(s) and alphavirus replicon RNA into the population of helper cells can be performed by any suitable means, as disclosed herein and as known to those generally skilled in the art.

Populations of alphavirus replicon particles are collected from the helper or packaging cells according to methods, e.g., as described in U.S. Pat. No. 7,078,218, the content of which is incorporated herein by reference in its entirety. Alternatively, they can be collected from packaging cells using other techniques known to those skilled in the art (e.g., U.S. Pat. Nos. 5,492,462 and 6,156,558). These populations are evaluated for the presence of replication competent virus (RCV) according to methods as described herein and as known in the literature. The populations of this invention contain no detectable RCV, as determined by passage on alphavirus-permissive cells in culture.

In some embodiments, the present invention can be employed to package an alphavirus RNA replicon encoding an immunogenic polypeptide in a subject (e.g., for vaccination), for immunotherapy (e.g., to treat a subject with cancer or tumors), or an immunomodulatory factor (e.g., for adjuvanting ARPs or other vaccine modalities). The present invention provides methods of eliciting or enhancing an immune response in a subject, comprising administering to the subject an effective amount of a nucleic acid packaged into particles by the helper constructs of this invention As used herein, "eliciting an immune response" and "immunizing a subject" includes the development, in a subject, of a humoral and/or a cellular immune response to a protein and/or polypeptide of this invention (e.g., an immunogen, an antigen, an immunogenic peptide, and/or one or more epitopes). A "humoral" immune response, as this term is well known in the art, refers to an immune response comprising antibodies, while a "cellular" immune response, as this term is well known in the art, refers to an immune response comprising T-lymphocytes and other white blood cells, especially the immunogen-specific response by HLA-restricted cytolytic T-cells, i.e., "CTLs."

It is also contemplated that the nucleic acids, particles, populations and pharmaceutical compositions of this invention can be employed in methods of delivering a NOI of interest to a cell, which can be a cell in a subject. Thus, the present invention provides a method of delivering a heterologous nucleic acid to a cell, comprising introducing into the cell an effective amount of a particle, population and/or composition packaged with the helper constructs of this invention. Also provided is a method of delivering a heterologous nucleic acid to a cell in a subject, comprising delivering to the subject an effective amount of a particle, population and/or composition packaged with the helper constructs of this invention. The cell can be any cell that can take up and express exogenous nucleic acids. The cell is maintained under conditions whereby the heterologous nucleic acid is expressed to produce a protein, peptide or other coding sequence product (e.g., a functional RNA sequence) encoded by the heterologous nucleic acid. Such methods can be employed to impart a therapeutic effect on a cell and/or a subject of this invention, according to well known protocols for immunization and/or gene therapy.

A "subject" of this invention includes, but is not limited to, warm-blooded animals, e.g., humans, non-human primates, horses, cows, cats, dogs, pigs, rats, and mice.

The present invention further provides a composition (e.g., a pharmaceutical composition) comprising a particle and/or population of particles of this invention in a pharmaceutically acceptable carrier. By "pharmaceutically acceptable" is meant a material that is not biologically or otherwise undesirable, i.e., the material may be administered to a subject along with the selected particles, and/or populations thereof, without causing substantial deleterious biological effects or interacting in a deleterious manner with any of the other components of the composition in which it is contained. The pharmaceutically acceptable carrier is suitable for administration or delivery to humans and other subjects of this invention. The carrier would naturally be selected to minimize any degradation of the active ingredient and to minimize any adverse side effects in the subject, as would be well known to one of skill in the art (see, e.g., *Remington's Pharmaceutical Science*; latest edition). Pharmaceutical formulations, such as vaccines or other immunogenic compositions, of the present invention comprise an immunogenic amount of the infectious, propagation defective alphavirus replicon particles produced using the helper constructs of this invention, in combination with a pharmaceutically acceptable carrier. Exemplary pharmaceutically acceptable carriers include, but are not limited to, sterile pyrogen-free water and sterile pyrogen-free physiological saline solution.

An "immunogenic amount" is an amount of the infectious alphavirus particles in the populations of this invention that is sufficient to evoke an immune response in a subject to which the population of particles is administered or delivered. An amount of from about $10^4$ to about $10^9$, especially $10^6$ to $10^8$, infectious units, or "IU", as determined by assays described herein, per dose is considered suitable, depending upon the age and species of the subject being treated. Administration may be by any suitable means, such as intraperitoneally, intramuscularly, intranasally, intravaginally, intravenously, intrademally (e.g., by a gene gun), intrarectally and/or subcutaneously. The compositions herein may be administered via a skin scarification method, and/or transdermally via a patch or liquid. The compositions can be delivered subdermally in the form of a biodegradable material that releases the compositions over a period of time.

As used herein, "effective amount" refers to an amount of a population or composition or formulation of this invention that is sufficient to produce a desired effect, which can be a therapeutic effect. The effective amount will vary with the age, general condition of the subject, the severity of the condition being treated, the particular agent administered, the duration of the treatment, the nature of any concurrent treatment, the pharmaceutically acceptable carrier used, and like factors within the knowledge and expertise of those skilled in the art. As appropriate, an "effective amount" in any individual case can be determined by one of ordinary skill in the art by reference to the pertinent texts and literature and/or by using routine experimentation. (See, for example, Remington, *The Science And Practice of Pharmacy* (20th ed. 2000)).

Alternatively, pharmaceutical formulations of the present invention may be suitable for administration to the mucous membranes of a subject (e.g., via intranasal administration, buccal administration and/or inhalation). The formulations may be conveniently prepared in unit dosage form and may be prepared by any of the methods well known in the art.

Also, the composition of this invention may be used to infect or be transfected into dendritic cells, which are isolated or grown from a subject's cells, according to methods well known in the art, or onto bulk peripheral blood mononuclear cells (PBMC) or various cell subfractions thereof from a subject.

If ex vivo methods are employed, cells or tissues can be removed and maintained outside the body according to standard protocols well known in the art while the compositions of this invention are introduced into the cells or tissues.

Immunogenic compositions comprising a population of the particles (which direct the expression of the nucleic acid sequence(s) of interest when the compositions are administered to a human or animal) of the present invention may be formulated by any means known in the art. Such compositions, especially vaccines, are typically prepared as injectables, either as liquid solutions or suspensions. Solid forms suitable for solution in, or suspension in, liquid prior to injection may also be prepared. Lyophilized preparations are also suitable.

The active immunogenic ingredients (e.g., the alphavirus replicon particles) are often mixed with excipients and/or carriers that are pharmaceutically acceptable and/or compatible with the active ingredient. Suitable excipients include but are not limited to sterile water, saline, dextrose, glycerol, ethanol, or the like and combinations thereof, as well as stabilizers, e.g., HSA or other suitable proteins and reducing sugars.

In addition, if desired, the vaccines may contain minor amounts of auxiliary substances such as wetting and/or emulsifying agents, pH buffering agents, and/or adjuvants that enhance the effectiveness of the vaccine. Examples of adjuvants which may be effective include but are not limited to: QS-21, Freund's adjuvant (complete and incomplete), aluminum salts (alum), aluminum phosphate, aluminum hydroxide; N-acetyl-muramyl-L-threonyl-D-isoglutamine (thr-MDP); N-acetyl-nor-muramyl-L-alanyl-D-isoglutamine (CGP 11637, referred to as nor-MDP); N-acetylmuramyl-L-alanyl-D-isoglutaminyl-L-alanine-2-(1'-2'-dipalmitoyl-sn-glycero-3hydroxyphosphoryloxy)-ethylamine (CGP 19835A, referred to as MTP-PE); and RIBI, which contains three components extracted from bacteria, monophosphoryl lipid A, trehalose dimycolate and cell wall skeleton (MPL+TDM+CWS) in a 2% squalene/Tween 80 emulsion.

Additional examples of adjuvants can include, but are not limited to, oil-in-water emulsion formulations, immunostimulating agents, such as bacterial cell wall components or synthetic molecules, or oligonucleotides (e.g., CpGs) and nucleic acid polymers (both double stranded and single stranded RNA and DNA), which can incorporate alternative backbone moieties, e.g., polyvinyl polymers.

The effectiveness of an adjuvant may be determined by measuring the amount of antibodies or cytotoxic T-cells directed against the immunogenic product of the alphavirus replicon particles resulting from administration of the particle-containing composition in a vaccine formulation that also comprises an adjuvant or combination of adjuvants. Such additional formulations and modes of administration as are known in the art may also be used.

Adjuvants can be combined, either with the compositions of this invention or with other vaccine formulations that can be used in combination with the compositions of this invention.

The compositions of the present invention can also include other medicinal agents, pharmaceutical agents, carriers, and diluents.

The compositions of this invention can be optimized and combined with other vaccination regimens to provide the broadest (i.e., covering all aspects of the immune response, including those features described hereinabove) cellular and humoral responses possible. In certain embodiments, this can include the use of heterologous prime-boost strategies, in which the compositions of this invention are used in combination with a composition comprising one or more of the following: immunogens derived from a pathogen or tumor, recombinant immunogens, naked nucleic acids, nucleic acids formulated with lipid-containing moieties, non-alphavirus vectors (including but not limited to pox vectors, adenoviral vectors, adeno-associated viral vectors, herpes virus vectors, vesicular stomatitis virus vectors, paramyxoviral vectors, parvovirus vectors, papovavirus vectors, retroviral vectors, lentivirus vectors), and other alphavirus vectors. The viral vectors can be virus-like particles or nucleic acids. Exemplary alphavirus vectors can be replicon-containing particles, DNA-based replicon-containing vectors (sometimes referred to as an "ELVIS" system, see, for example, U.S. Pat. No. 5,814,482) and/or naked RNA vectors.

The immunogenic (or otherwise biologically active) alphavirus particle-containing populations and compositions of this invention are administered in a manner compatible with the dosage formulation, and in such amount as will be prophylactically and/or therapeutically effective. The quantity to be administered, which is generally in the range of about $10^4$ to about $10^9$ infectious units per mL in a dose, depends on the subject to be treated, the route by which the particles are administered or delivered, the immunogenicity of the expression product, the types of effector immune responses desired, and the degree of protection desired. In some embodiments, doses of about $10^6$, $10^7$, and $10^8$ I.U. may be particularly effective in human subjects. Effective amounts of the active ingredient required to be administered or delivered may depend on the judgment of the physician, veterinarian or other health practitioner and may be specific for a given subject, but such a determination is within the skill of such a practitioner.

The compositions and formulations of this invention may be given in a single dose or multiple dose schedule. A multiple dose schedule is one in which a primary course of administration may include 1 to 10 or more separate doses, followed by other doses administered at subsequent time intervals as required to maintain and or reinforce the desired effect (e.g., an immune response), e.g., weekly or at 1 to 4 months for a second dose, and if needed, a subsequent dose(s) after several months (e.g., 4 or 6 months)/years.

Efficacy of the treatment methods of this invention can be determined according to well known protocols for determining the outcome of a treatment of a disorder of this invention. Determinants of efficacy of treatment, include, but are not limited to, overall survival, disease-free survival, improvement in symptoms, time to progression and/or quality of life, etc., as are well known in the art.

"Treat" or "treating" or "treatment" refers to any type of action that imparts a modulating effect, which, for example, can be a beneficial effect, to a subject afflicted with a disorder, disease or illness, including improvement in the condition of the subject (e.g., in one or more symptoms), delay or reduction in the progression of the condition, prevention or delay of the onset of the disorder, disease or illness, and/or change in any of the clinical parameters of a disorder, disease or illness, etc., as would be well known in the art.

It is understood that the foregoing detailed description is given merely by way of illustration and that modifications and variations may be made therein without departing from the spirit and scope of the invention.

EXAMPLES

Example 1

Construction of dHcap and dHgp Helpers

Primers were designed (capsid F (SEQ ID NO:98), GP F (SEQ ID NO:60) and 13-101.pr4 (SEQ ID NO:61) (Table 1), to amplify the capsid and glycoprotein (GP) genes out of the VEE helper plasmids (referred to as "13.2.2" for the capsid helper and "13.4.6" for the glycoprotein helper), which are described in U.S. Pat. No. 5,792,462, Pushko et al., 1997 (Virology 239:389-401), and PCT publication WO 02/03917 (Olmsted et al.). These primers provide an Rsr II restriction site and also bind to the start of the capsid or glycoprotein coding sequence, respectively. The DNA plasmids described in the above-cited references are a convenient source for obtaining the structural protein coding fragments, e.g., by PCR amplification. Alternatively, these coding fragments can be obtained from full-length clones of VEE or attenuated variants thereof (see U.S. Pat. No. 5,185,440; U.S. Pat. No. 5,505,947).

Amplification with these primers resulted in fragments with the following elements, listed from the 5' to the 3' ends of the PCR product: 5'-RsrII restriction site, VEE structural protein coding sequence ORF, 3' UTR, SphI restriction site-3'. The PCR products were then digested with RsrII and SphI restriction enzymes and ligated into an empty VEE replicon vector, as described in U.S. Pat. No. 5,792,462, Pushko et al., 1997 (Virology 239:389-401) and PCT Publication No. WO 02/03917 (Olmsted et al.). This replicon RNA contains the VEE nonstructural genes and a single copy of the 26S subgenomic RNA promoter followed by a multiple cloning site (MCS). In a vaccine construct, one or more coding sequences encoding an immunogen are inserted into this cloning site. This vector is digested with RsrII and SphI (removing most of nsP1 and all of nsPs2-4), and upon ligation, helpers are generated which comprise the complete alphavirus 5' and 3' ends, i.e., "full-length" ends. These two helpers are therefore designated dHcap(FL) and dHgp(FL) and they have the 5' sequences of SEQ ID NO:1 and SEQ ID NO:10, respectively and the 3' sequences of SEQ ID NO:55 and SEQ ID NO:56, respectively (FIG. 1).

Figure 2:
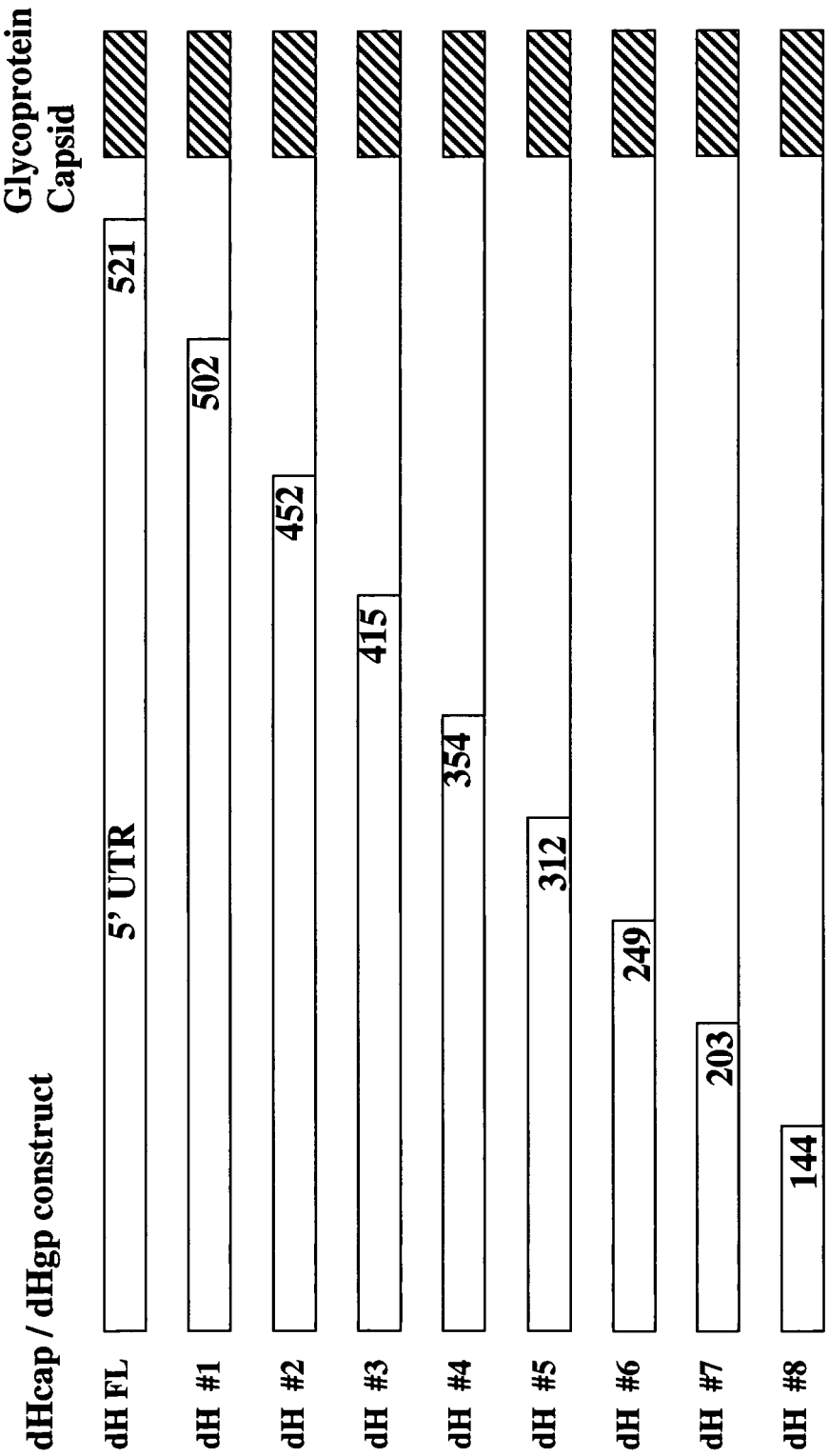
FIG. 2 shows the structure of 5' replication recognition sequence deletions in a promoterless helper molecule. The outlined boxes indicate the 5' replication recognition sequence remaining in each construct and the number inside the box is the nucleotide length of the sequence. Thin black lines indicate the 5' replication recognition sequence that has been deleted from each construct. Boxes with diagonal stripes represent the location of the coding sequence for either capsid or GP.

Subsequently, eight consecutive deletions of approximately 50 nt each were made in the 522 nt 5' end present in both the dHcap(FL) and dHgp(FL) helpers (FIG. 2). The procedure was carried out in two steps. First, eight different reverse primers (dHelp1-8 R, SEQ ID NOS: 63-70) were designed complementary to the 5' end up to position 502 of the 13.2.2 and 13.4.6 helpers (described hereinabove), and each was engineered to additionally contain an RsrII restriction site (Table 1). A forward primer (3-16.1.1 (SEQ ID NO:62), Table 1) was designed, which when combined with any of the reverse primers, amplified a fragment with the following elements (listed 5' to 3'): 5'-XbaI restriction site, T7 promoter, 5' truncated end, RsrII restriction site-3'. Second, the amplified 5' truncated end fragments were cloned into the dHcap(FL) and dHgp(FL) helpers linearized with XbaI and RsrII. This generated eight sets of 5' truncated end helper constructs, designated dHcap 1-8 and dHgp 1-8, which have the 5' sequences of SEQ ID NOS: 2-9 and SEQ ID NOS: 11-18, respectively. The 3' sequence of each member of the dHcap series is provided herein as SEQ ID NO:55 and the 3' sequence of each member of the dHgp series is provided herein as SEQ ID NO:56.

Example 2

Methods for Expression Analysis of Promoterless Helper Expression Cassettes

To determine how well the Δ26S helper configurations described herein expressed VEE structural proteins, each helper was electroporated into Vero cells along with a VEE replicon vector as described above. For purposes of demonstrating the capability of the novel promoterless structural protein expression cassettes of this invention, VEE replicons were constructed by inserting a GFP or a botulinum neurotoxin coding sequence into the VEE replicon vector's cloning site. Expression of these coding sequences from particles made with various combinations of the promoterless structural protein expression cassettes described herein demonstrated the utility and novelty of these cassettes.

RNA was transcribed from each helper and replicon vector by run-off transcription using RiboMAX T7 Express® transcription kits (Promega Corporation, Madison, Wis.) according to the manufacturer's procedure. Before electroporation, helper and replicon RNAs were purified by silica-based chromatography. Thirty micrograms (30 μg) of each helper and replicon RNA were combined and electroporated into 3-5× $10^7$ Vero cells. Electroporated cells were diluted in medium and seeded into 25 $cm^2$ flasks or 96 well plates. The electroporated cells were then incubated for 16-24 hr at 37° C.

A. IFA Analysis

Electroporated cells seeded into 96 well plates were washed with phosphate buffered saline (PBS) one time and then fixed with acetone:methanol (1:1) at room temperature for five min. The cells were then analyzed for expression of VEE capsid or GP protein using structural protein specific mouse antibodies. Primary antibody was diluted in PBS:FBS (1:1) and 100 μl was added to each well. Plates were incubated at 37° C. for 30 min, washed with 150 μl PBS three times and then incubated with Alexa Fluor 488 goat anti-mouse secondary antibody (Invitrogen, Carlsbad, Calif.) for 30 min at 37° C. After incubation, cells were washed again as described above and a final volume of 100 μl PBS was added to each well before inspection by ultraviolet fluorescence microscopy (Nikon Eclipse TE300).

B. Northern Analysis

Electroporated cells seeded into 25 $cm^2$ flasks were washed with PBS and then total cellular RNA was extracted using RNAwiz RNA® isolation reagent (Ambion, Austin, Tex.) following the manufacturer's suggested protocol. RNA concentration was determined by spectrophotometry. Five micrograms (5 μg) of each sample were electrophoresed through a 1% glyoxal agarose gel and RNA was passively transferred to BrightStar Plus® (Ambion) membranes. Northern analysis was carried out with a biotinylated DNA oligo specific for the positive strand of the VEE 3' replication recognition sequence using a BrightStar BioDetect® kit (Ambion) following the manufacturer's suggested protocol. Chemiluminescence was detected by exposing the processed membranes to film.

C. Analysis of dHcap(FL) and dHgp(FL) Expression To demonstrate that the full-length Δ26S helpers (dHcap (FL) and dHgp(FL)) could be replicated and express proteins, these helper RNAs were electroporated into cells along with a replicon vector, which is needed to provide the alphavirus non-structural proteins that facilitate replication of the helper RNAs. Vero cells were electroporated with either 30 or 60 µg of dHcap(FL) or dHgp(FL) helper RNA combined with 30 µg of replicon RNA. The electroporated cells were processed for IFA, Western blot and Northern analysis as described above.

Example 3

Expression Analysis for Full-Length and Truncated Δ26S Helpers

The dHcap(FL) and dHgp(FL) helpers expressed protein as determined by IFA and Western blot and were replicated efficiently as demonstrated by Northern blot.

The complete set of truncated Δ26S helpers (deletions 1-8) for both capsid and GP were analyzed for protein expression by IFA and by Northern blot to determine how well each was expressed and replicated. Each dHcap helper RNA was combined with a VEE replicon RNA and the 13.4.6 glycoprotein helper RNA, and the three RNAs were electroporated into Vero cells. Northern analysis and IFA were carried out as described above. The results of IFA using a capsid specific antibody are shown in Table 2. All dHcap helpers were positive for capsid expression by IFA although the dHcap8 helper was only weakly positive.

Northern analysis of RNA extracted from electroporated cells indicated that all of the truncated capsid Δ26S helpers replicated well except for dHcap8.

The dHgp helpers were examined in a similar manner but the 13.2.2 capsid helper was not included in this experiment. Each dHgp helper was combined with a VEE replicon RNA, electroporated into cells, and samples were generated as described above for IFA and Northern analysis. Results of anti-GP IFA are shown in Table 3. Similar to the dHcap helpers, all dHgp helpers were positive except dHgp8. All dHgp helpers replicated well with the exception of dHgp8.

Example 4

Modified Promoterless Helper Constructs

The inventors noted that the dHcap(FL) and dHgp(FL) helpers expressed fusion proteins, as revealed by Western blotting. Such fusion proteins could be the result of initiation of translation at in-frame start codons upstream of the start codon for capsid or GP on the Δ26S helper transcripts. One such upstream codon is the native start codon for VEE nsP1 (located at nucleotide 45 in the VEE viral genome), which is present in the 5' end of both the dHcap and dHgp helpers, and is in a favorable context for initiation of translation (e.g., a Kozak consensus sequence). It is possible that a start codon in a favorable Kozak environment could be used by ribosomes scanning from the capped 5' end of these helpers, thereby generating fusion proteins that are not functional and decreasing the production of functional capsid and glycoprotein polypeptides from the appropriate start codon located further downstream.

Two approaches were used to decrease the amount of such fusion proteins produced and increase full-length capsid and glycoprotein protein expression. First, the favorable start codon described above was mutated to a TAG stop codon and the remaining start codons were left unchanged. This approach was taken to keep the 5' end sequence as close to the sequence present in the native VEE genome as possible, in order to maintain the replication elements relied upon for these helpers. Second, all of the start codons downstream of nt 3 (including the nsP1 (favorable) start codon) and the capsid or glycoprotein coding sequence open reading frame (ORF) were changed from AUG to GUG (there were a total of 12 such changes). This approach was taken to determine whether less favorable ATG codons (AUG in RNA) might also have detrimental effects on the production of full-length capsid or glycoprotein expression.

A. Construction of dHcap-mut1 and dHgp-mut1 Helpers

To generate dHcap and dHgp helpers that have the favorable nsP1 start codon changed to a TAG stop codon, site directed mutagenesis was carried out on each dHcap and dHgp helper, generating a complete set (FL and truncations 1-7) of mutated helpers, designated dHcap-mut1 and dHgp-mut1 helpers, which have 5' sequences as provided herein as SEQ ID NOS: 35-42 and 43-50, respectively. Site directed mutagenesis was carried out with a Quikchange XL® site directed mutagenesis kit (Stratagene, La Jolla, Calif.) according to the manufacturer's protocol using forward (SEQ ID NO:71) and reverse (SEQ ID NO:72) primers in Table 4.

B. Construction of dHcap-mm and dHgp-mm Helpers

To generate dHcap and dHgp helpers with 5' ends that do not have any start codons downstream of nt 3 and the capsid or GP ORF start codons, site directed mutagenesis was carried out to change all intervening ATG (AUG IN RNA) codons to GTG (GUG in RNA) codons. The dHgp(FL) construct was used as the template for site directed mutagenesis. A Quikchange® multi site-directed mutagenesis kit (Stratagene) was used to introduce the codon changes using the manufacturer's protocol. The primers used to introduce the codon changes are shown in Table 5 (SEQ ID NOS: 73-82). The dHgp(FL) construct containing all of the codon changes was designated dHgp(FL)-mm (having the 5' sequence provided herein as SEQ ID NO:19). After sequence confirmation that all codon changes were present, this DNA was used to generate the dHcap(FL)-mm construct by replacing the dHcap(FL) 5' replication recognition sequence with the 5' replication recognition sequence from dHgp(FL)-mm. This was accomplished by digesting both DNAs with RsrII and Not I enzymes. The dHgp(FL)-mm RsrII/NotI 5' replication recognition sequence fragment was then ligated with the linearized dHcap(FL) DNA, generating dHcap(FL)-mm (having the 5' sequence provided herein as SEQ ID NO:27). In addition, the dHgp(FL)-mm DNA was used as the template to generate the 5' truncated end sets for both capsid and GP helpers using the method and primers described above for dHcap1-7 and dHgp1-7. The new helpers were designated dHcap1mm-dHcap7 mm (having 5' sequences provided herein as SEQ ID NOS:20-26) and dHgp1mm-dHgp7 mm (having 5' sequences provided herein as SEQ ID NOS:28-34).

C. Analysis of Expression of mut1 and mm Promoterless Helpers

Protein production from various mut1 and mm versions of the Δ26S helpers described above was analyzed. In this experiment, the dHcap6-mut1 (with the 5' sequence provided herein as SEQ ID NO:41), dHcap6-mm (with the 5' sequence provided herein as SEQ ID NO:25), dHcap7-mm (with the 5' sequence provided herein as SEQ ID NO:26) and dHgp7-mm (with the 5' sequence provided herein as SEQ ID NO:27), as well as the 13.2.2 and 13.4.6 helpers, were analyzed by Western blot. The Δ26S helpers containing the mm mutations expressed primarily full length capsid or GP proteins with little or no fusion proteins detectable. The mut1 helpers expressed significant amounts of full-length structural protein, but they also continued to express some fusion proteins.

Northern analysis was carried out on the same samples to analyze the replication characteristics of the mut1 and mm Δ26S helpers. The results indicate that the dHcap6-mut1 helper replicates as well as the 13.2.2 capsid helper. In contrast, the dHcap6-mm, dHcap7-mm and dHgp7-mm helpers appear to replicate to a lesser extent than 13.2.2 or mut1 helpers.

Example 5

VEE Replicon Particle Generation with Δ26S Helpers

Listed in Table 6 are a number of experiments combining different promoterless capsid and GP helpers with a VEE replicon RNA to produce VEE replicon particles (VRP). In addition, the amount of each helper RNA introduced into cells was also varied in some experiments. VRPs were generated by electroporating $5 \times 10^7$ to $1 \times 10^8$ Vero cells with the indicated amounts of helper RNA as well as 30 µg of replicon RNA. In general, for all experiments in which particles are generated, electroporated cells were seeded into 300 cm² flasks containing serum free media and incubated 16-24 hr before the VRPs were harvested.

VRP titers were determined by infecting Vero cells, grown in 96 well plates, with ten-fold serial dilutions of sample, incubating the cells for 16-18 hr, fixing the cells and performing IFA with antibodies specific for VEE nsP2 protein or the product of the nucleic acid of interest. VRP yields are reported either as total yield from an experiment (i.e., Table 6) or on a per ml basis from a 20 ml preparation (Tables 7, 9-13, 15 and 16).

These preparations were also tested for the presence of replication-competent virus (RCV) by a cytopathic effect (CPE) assay. The CPE assay consisted of two blind passages in cell culture to screen for the presence of RCV. For Passage 1, samples from a VRP preparation were incubated with Vero cell monolayers for 1 hr at 37° C., then the sample fluids were removed and replaced with fresh medium, and the cultures were incubated for 24 hr to allow amplification of any RCV that might be present. For Passage 2, cell culture supernatants at the end of Passage 1 were added to fresh Vero cell monolayers and incubated at 37° C. for 72 hr. At the end of Passage 2, cultures were inspected for CPE using an inverted light microscope. This assay has been standardized and evaluated for sensitivity in detecting viable virus in the presence of a large excess of VRP. Using either V3014 or TC-83 viruses in this assay, spiking studies revealed a lower limit of detection of 3-8 PFU on a background of $1 \times 10^8$ VRP. This assay has been performed on more than $10^{13}$ VRPs produced with the promoterless helpers of this invention, and no RCV has ever been detected. Despite the limit of detection of this assay, theoretical calculations of the possible recombination frequency for generation of RCV would be much lower using this limit of detection, i.e., 1 in $10^{10}$, 1 in $10^{11}$, 1 in $10^{12}$, or 1 in $10^{13}$ VRPs.

Example 6

"Split Glycoprotein" Promoterless Helpers

A. Construction of Separate E2 and E1 Promoterless Helpers

Construction of glycoprotein promoterless helpers in which the E2 and E1 coding sequences were placed on separate helpers was performed by cloning the E2 and E1 glycoprotein cassettes separately into the backbone of the dHgp6-mut1 helper. Primers were designed to amplify by PCR the capsid-E3-E2 region of the VEE structural protein coding region from pHCMV-Vsp (see U.S. Pat. No. 7,045,335, incorporated herein by reference). The amplified fragment was cloned into the pCR-Blunt II TOPO® vector(Invitrogen), generating pCR-CE3E2. The CE3E2 cassette was sequenced to ensure that no errors were introduced during PCR amplification. To produce a promoter-assisted helper that contained the CE3E2 structural region, the pCR-CE3E2 DNA was digested with SpeI restriction enzyme to release an E3E2 fragment. The E3E2 (SpeI) fragment was then ligated with the capsid helper (13.2.2) linearized with SpeI enzyme to produce pHCE3E2. The promoterless E2 helper (designated dHE2-6M1) was prepared by digesting the E3-E2 coding region from pHCE3E2. The pHCE3E2 DNA plasmid was first linearized with AscI restriction enzyme and then treated with T4 DNA polymerase to create a blunt end. Similarly, the dHgp6-mut1 DNA plasmid was linearized with SphI restriction enzyme and T4 DNA polymerase-treated to create a blunt end. Both linearized, T4-polymerase treated DNAs were then digested with SpeI restriction enzyme, and the resulting 3.6 kb dHgp6-mut1 vector fragment and 1.4 kb E3-E2 fragment were each gel-purified. The two purified fragments were then ligated together using T4 DNA ligase to produce the dHE2-6M1 promoterless helper.

Generation of a promoterless E1 helper was accomplished in several steps. Primers were designed to amplify two structural protein coding sequence fragments: 1) capsid-E3 (CE3), and 2) 6K-E1 (6KE1). The PCR products were cloned into the pCR-Blunt TOPO® vector (Invitrogen), generating pCR-CE3 and pCR-6KE1. The clones were sequenced to ensure that no errors were introduced during amplification. To produce a cassette that contained both the E3 and 6K leader sequences upstream of the E1 glycoprotein, another intermediate construct was produced. This was accomplished by digesting pCR-6KE1 DNA with BamHI enzyme and purifying the 6KE1 fragment. The 6KE1 (BamHI) fragment was then ligated with pCR-CE3 DNA linearized with BamHI enzyme, generating pCR-CE36KE1. To generate a promoter-assisted helper containing the CE36KE1 cassette, pCR-CE36KE1 DNA was digested with SpeI and SphI enzymes releasing the structural protein coding sequence cassette. The CE36KE1 (SpeI/SphI) fragment was then ligated with capsid helper (13.2.2) linearized with SpeI and SphI to produce pHCE36KE1. Generation of the promoterless E1 helper (designated dHE1-6M1) was accomplished by digesting the E3-6K-E1 coding region from the pHCE36KE1 plasmid. The pHCE36KE1 and dHgp6-mut1 DNA plasmids were digested with SpeI and SphI restriction enzymes and the resulting 3.6 kb dHgp6-mut1 vector fragment and 1.7 kb E3-6K-E1 fragments were gel-purified. The two purified fragments were then ligated together using T4 DNA ligase to produce the dHE1-6M1 promoterless helper.

B. Analysis of Split Glycoprotein Promoterless Helpers

Figure 3:
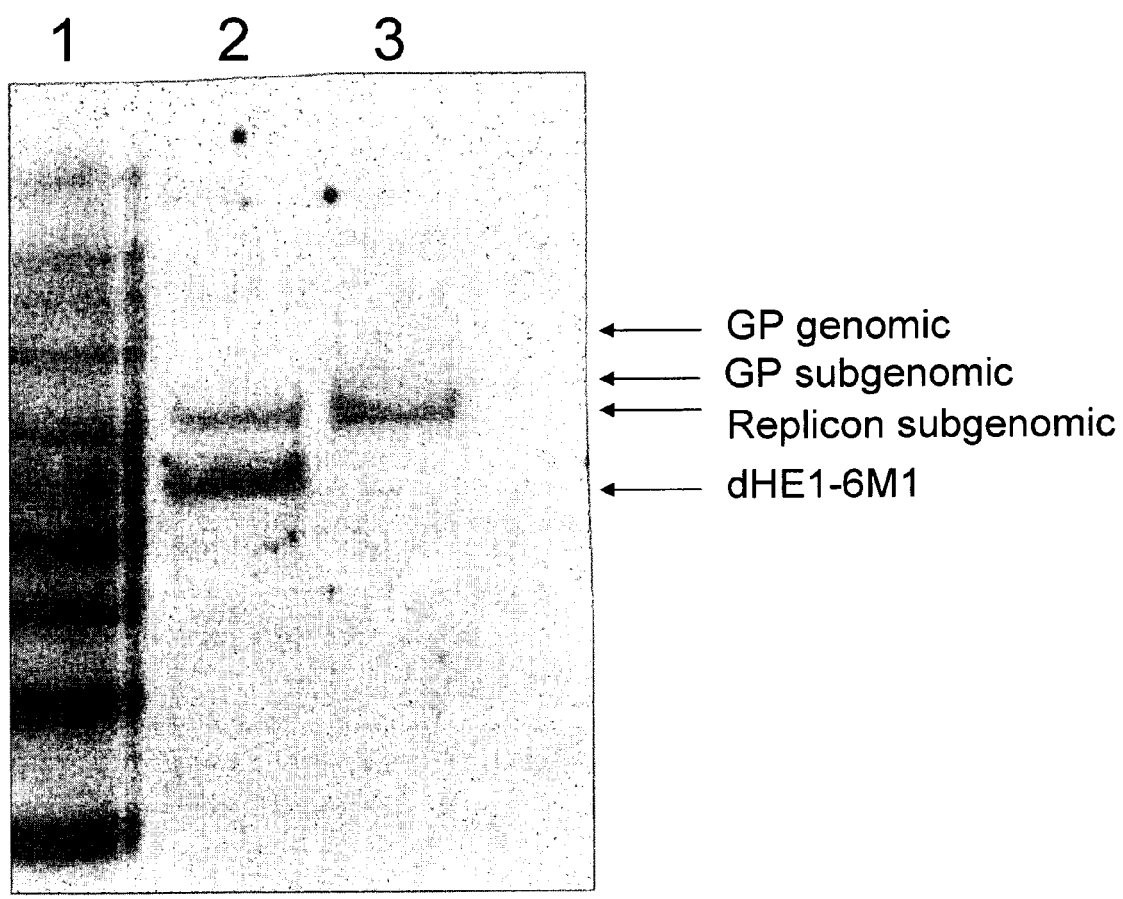
FIG. 3 is a Northern blot analysis. Total cellular RNA was extracted from Vero cells electroporated with 30 μg of pERK/342/MS/BoNT A replicon RNA and either 30 μg of dHE1-6M1 (a promoterless E1 helper) or 30 μg of a GP helper RNA containing a 26S promoter (13.4.6). RNA for each sample (5 μg) was run on a 1% glyoxal gel and transferred to a Bright-Star® membrane (Ambion; Austin, Tex.). A probe specific for the genomic sense alphavirus RNA 3' end was used to detect replication of the helpers. Lane 1: RNA molecular weight marker, lane 2: dHE1-6M1 helper+BoNT A replicon, lane 3: promoter-assisted GP helper+BoNT A replicon.

The individual glycoprotein helpers were transcribed in vitro, and the RNA transcripts were purified prior to being electroporated into Vero cells along with a VEE replicon RNA. Helper replication was analyzed by Northern blot and protein expression was analyzed by IFA using E1 and E2 glycoprotein specific antibodies. Northern results indicate the both the dHE1-6M1 and dHE2-6M1 helper replicate efficiently. A representative Northern blot is shown in FIG. 3.

To determine whether the two individual glycoprotein-expressing promoterless helpers could be combined with a Δ26S capsid helper to package a replicon RNA to produce VRP, the three helpers were combined with VEE replicon RNA expressing a botulinum neurotoxin A fragment and electroporated into Vero cells. VRP yields from one experiment are shown in Table 7.

Example 7

Modified 5' and 3' End Promoterless Helper Cassettes

A. Construction of Modified 5' End Helper Cassettes

The predicted secondary structure at the 5' end (~first 250 nt) of the RNA of most alphaviruses contains four stem loop (SL) structures (SL1, SL2, SL3 and SL4). Frolov et. al. (*RNA*, 7:1638-1651 (2001)) demonstrated that removal of the nucleotide sequences encoding SL2 from a Sindbis virus helper RNA increased replication of that helper.

The SL2 region in the VEE 5' end (based on the M-fold program), nt 46 to nt 116 inclusive, was removed from the dHcap6-mut1 by PCR as follows. Two fragments were amplified from dHcap6-mut1 DNA. A 5' fragment of approximately 1 kilobase (kb) was amplified with primers 13-82.1.9 [SEQ ID NO. 83] and dLS2(EcoRV) R [SEQ ID NO. 84] (Table 8) that contained the 45 nucleotides at the 5' end of dHcap6-mut1 and the nucleotides encoding the backbone plasmid sequence. A 3' fragment of approximately 1.5 kb was amplified with primers dSL2 (EcoRV) F [SEQ ID NO. 85] and 3-8.pr4 [SEQ ID NO. 86] (Table 8) that contained the portion of the VEE 5' end beginning with nucleotide 117 and the nucleotides encoding the entire capsid sequence through the VEE 3' end. The 5' ~1 kb PCR fragment was digested with XhoI and EcoRV restriction enzymes. The 3' ~1.5 kb PCR fragment was digested with EcoRV and NotI restriction enzymes. Plasmid dHgp6-mut1 was linearized by digestion with XhoI and NotI and the resulting ~2.5 Kb vector backbone was purified. To generate the new helper in which the SL2 region was deleted, herein referred to as "dHcap6-mut1 (dSL2)," the 5' (XhoI/EcoRV) fragment, 3' (EcoRV/NotI) fragment, and the XhoI/NotI linearized vector were ligated together. The dHcap6-mut1(dSL2) helper, with a 5' end the sequence of which is provided herein as SEQ ID NO. 51, was completely sequenced to ensure that no errors were introduced during PCR amplification. To generate the matching dHgp6-mut1(dSL2) helper, dHgp6-mut1 DNA was digested with XhoI and RsrII restriction enzymes and the 5.4 kb fragment was purified. The modified 5' end from dHcap6-mut1 (dSL2) was collected by digesting this DNA with XhoI and RsrII and purifying the 1.1 kb fragment. These two fragments were ligated together to generate dHgp6-mut1 (dSL2), which has the identical 5' end [SEQ ID NO. 51] as dHcap6-mut1 (dSL2).

B. Construction of Shortened 3'-End Promoterless Helper Cassettes.

In these examples, for the capsid helper constructs dHcap (FL), dHcap1 through dHcap7, dHcap(FL)mm, dHcap1mm through dHcap7 mm, dHcap(FL)mut1, and dHcap1mut1 through dHcap7mut1, the 3' end sequence is provided herein as SEQ ID NO. 55. Although the VEE capsid helpers of this invention lack the complete glycoprotein coding region, a small portion of the E3 protein remains on the capsid helper to allow the chymotrypsin-like cleavage to occur within the packaging cell to produce mature capsid protein. For the glycoprotein helper constructs dHgp(FL), dHgp1 through dHgp7, dHgp(FL)mm, dHgp1mm through dHgp7 mm, dHgp (FL)mut1, and dHgp1mut1 through dHgp7mut1, the 3' end sequence was a shorter sequence, since the sequence comprising the cleavage site for generating the mature capsid protein is not required in the glycoprotein helper constructs.

The 3' sequence used for these glycoprotein constructs in these examples is provided herein as SEQ ID NO. 56.

In addition, promoterless RNA helpers with shorter 3' end lengths were constructed. By reducing the amount of alphavirus 3' end sequence, the theoretical possibility for a second recombination event, which would be required to generate replication competent VEE virus, is further reduced. Initially, a glycoprotein helper with a functional 26S promoter containing only the 19 nucleotides comprising the alphavirus highly conserved 3' sequence [SEQ ID NO. 52] was produced in the following two steps. First, a plasmid was produced that contained a glycoprotein (GP) coding sequence cassette with unique 5' and 3' restriction sites. Primers were designed to amplify the VEE GP with a unique SphI site just after the E1 termination codon at the 3' end ("GP (SphI) R," SEQ ID NO. 87, Table 8) and an existing internal SpeI site at the 5' end ("3-16.1.3," SEQ ID NO. 88, Table 8). The amplified fragment was TA cloned into pCR2.1 DNA (Invitrogen, Carlsbad, Calif.) generating pCR2.1/GP 19 nt 5'. Second, a forward primer was designed to introduce a SphI site just upstream of the 19 nucleotide conserved sequence at the VEE 3' end (3' trunc (SphI) F, SEQ ID NO. 89, Table 8). A reverse primer, specific for the plasmid backbone sequence, was designed to amplify a fragment that would contain a unique AflII restriction site at the 3' end (3' trunc (AflIII) R, SEQ ID NO. 90, Table 8). The fragment resulting from amplification with these primers was digested with SphI and AflII and ligated into the 13.4.6 glycoprotein helper (described in Example 1), which had been linearized with SphI and AflII restriction enzymes, thereby resulting in construction of pGP helper-int1. The pGP helper-int1 construct has a 72 nucleotide region between the GP stop codon and the 3' end of the helper (including the 19 nt conserved sequence). To generate a GP helper with only the 19 nucleotide 3' end, the pCR2.1/GP 19 nt 5' DNA was digested with SpeI and SphI and the GP coding sequence ligated into the pGP helper-int1 digested with SpeI and SphI restriction enzymes. The resultant construct was named pGP helper 19 nt.

The pGP helper 19 nt construct was then used to produce Δ26S helpers with variable length 3' replication recognition sequences. The pGP helper 19 nt construct was digested with NcoI and NotI restriction enzymes and the 2515 base pair fragment containing the glycoprotein coding sequence with the 19 nt 3' end region was gel-purified. This 2515 base pair (NcoI/NotI fragment was then ligated into dHgp constructs digested with NcoI and NotI restriction enzymes, generating the various dHgp 19 nt constructs.

C. Construction of a Modified Promoterless Helper Cassette Expressing the Alphavirus Capsid Protein.

In a VEE virus-infected cell, the VEE capsid protein cleaves itself from the structural polyprotein that is translated from the 26S subgenomic mRNA. Although the VEE capsid helpers of this invention lack the complete glycoprotein coding region, a small portion of the E3 protein remains on the capsid helper to allow the chymotrypsin-like cleavage to occur within the packaging cell to produce mature capsid protein. Introduction of a stop codon at the 3' end of the capsid, in place of the chymotrypsin-like cleavage site, would increase the difficulty of producing functional recombinants with a glycoprotein helper. That is, for a functional recombination (i.e., one that generates a replication competent virus) to occur with a dHgp helper of this invention, the recombination event would have to be nucleotide perfect to replace the engineered stop codon in the capsid coding sequence and maintain an active capsid cleavage site. Two versions of dHcap helpers with stop codons incorporated at the 3' end were produced. One version, dHcap6-mut1-dSL2 (stop), which has a 3' sequence provided herein as SEQ ID NO:57, replaced the C-terminal tryptophan residue of the native capsid protein with a stop codon; the other version retained the C-terminal tryptophan residue (dHcap6-mut1 (W-stop), which has a 3' sequence provided herein as SEQ ID NO: 59) and inserted a stop codon immediately downstream of the tryptophan residue. The capsid coding sequence was amplified with primers designed to engineer a unique RsrII site at the 5' end (Capsid (RsrII-Kozak) F, SEQ ID NO: 91, Table 8) and a unique SphI site at the 3' end (Capsid (stop) SphI R, SEQ ID NO:92 or Capsid (W-stop) SphI R, SEQ ID NO: 93, Table 8). The forward primer was also engineered to place the capsid start codon in a near-optimal Kozak consensus sequence (Kozak, Cell, 44(2):283-292 (1986)) to enhance ribosome initiation of translation of the capsid mRNA. The amplified capsid coding sequences were digested with RsrII and SphI restriction enzymes and ligated into Δ26S helper plasmids linearized with RsrII and SphI to produce dHcap6-mut1-dSL2 (stop) and dHcap6-mut1 (W-stop) constructs.

D. Construction of Modified Promoter Helper Cassette Expressing Alphavirus Glycoproteins.

The VEE capsid protein is a chymotrypsin-like protease that cleaves after the capsid C-terminal tryptophan residue. On the basis of the cleavage specificity of chymotrypsin, it is expected that all amino acid residues are tolerated in the position immediately downstream of the tryptophan except methionine and proline. Having either of these amino acids immediately downstream of the tryptophan is expected to greatly reduce chymotrypsin cleavage activity. In the native VEE virus, there are 18 amino acids that comprise the VEE E3 signal sequence. Constructs were designed to reduce the number of amino acids in the E3 signal sequence while maintaining the signaling function of the E3 sequence. Since 16 of the 18 amino acids comprising the E3 sequence are expected to be tolerated in the position downstream of the capsid C-terminal tryptophan, reducing the number of amino acids in the E3 signal sequence will reduce the number of sites that would be functional as cleavage sites if they were placed immediately downstream of the C-terminal tryptophan upon the occurrence of a nucleotide-perfect recombination event that reconstituted the VEE structural polyprotein coding sequence. As an example of such an approach, the N-terminal serine residue normally present in the E3 signal sequence was removed by PCR, leaving a leucine residue as the N-terminal residue, and a dHgp promoterless helper was constructed to determine if such a modified gp helper would function to package VRP.

A forward PCR primer (Gp (RsrII-Ser) F, SEQ ID NO: 94) was designed to remove the N-terminal serine residue of E3 and maintain a unique RsrII restriction site (Table 8). A reverse PCR primer (3-16.2.14, SEQ ID NO: 95) was designed to amplify a gp fragment that would contain a unique SnaBI restriction site (Table 8). The resulting gp PCR fragment was digested with RsrII and SnaBI and ligated into RsrII and SnaBI digested dHgp6-mut1 DNA, generating dHgp6-mut1 (-S).

E. VRP Generation Experiments Using 5' and 3' Modified Δ26S Helpers

Helpers that contain combinations of the modifications described above were also prepared. Different combinations and RNA concentrations of the dHcap and dHgp promoterless helpers were analyzed in VRP production experiments to determine how effectively they would package a VEE replicon RNA (either one expressing the botulinum neurotoxin fragment A or an influenza HA). In addition, the effect of capping the Δ26S helpers on VRP yields was analyzed for a subset of the helper combinations. Representative examples of VRP yields are shown in Tables 9-13 with different combinations of Δ26S helpers. The potency assay to quantitate VRP infectivity and yield is performed in Vero cell monolayer cultures in 48-well plates by serially diluting VRP and incubating with Vero cells overnight at 37° C. in 5% $CO_2$ After overnight incubation (18-20 hours), the cells are washed, fixed, and the fixed monolayers stained with an antigen-specific primary antibody followed by a FITC-conjugated secondary antibody. Cells containing FITC-labeled antigen-antibody complexes are detected by ultraviolet fluorescence microscopy (Nikon Eclipse TE300). Individual antigen-positive cells are counted and the titer, expressed as IU/mL, is calculated from the known dilution and inoculation volume.

Example 8

Promoterless Helpers Incorporating a Ubiquitin Monomer

A. Construction of Δ26S Helpers Containing Ubiquitin Monomers

Figure 4:
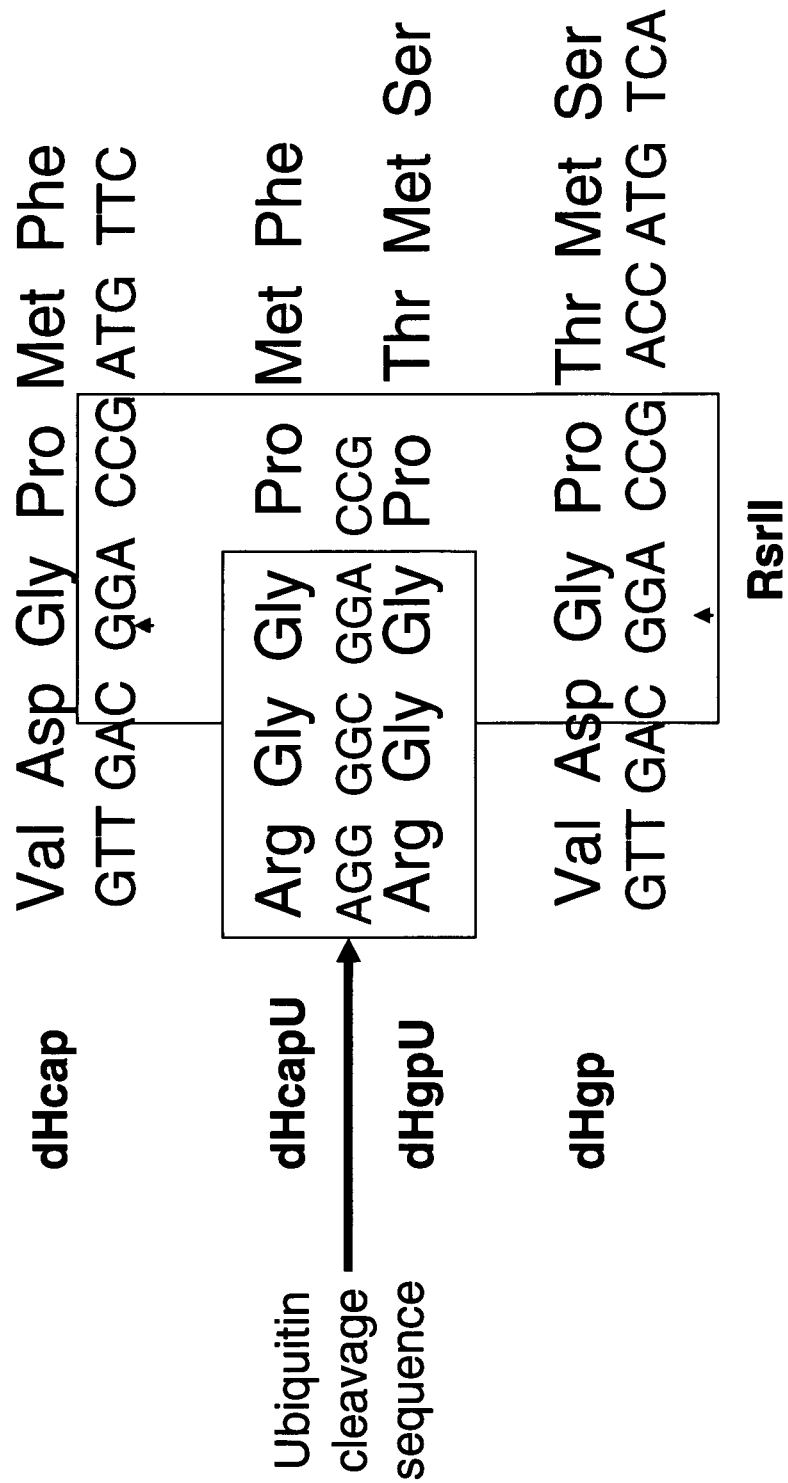
FIG. 4 is a diagram showing the C-terminal amino acid and nucleotide sequence of the ubiquitin monomer and N-terminal residues of alphavirus capsid and glycoprotein coding sequences for ubiquitinated (dHcapU, SEQ ID NO:99, and dHgpU, SEQ ID NO:100) or standard (dHcap, SEQ ID NOs: 101 and 102, and dHgp, SEQ ID NOs:103 and 104) constructs. The "Met Phe," "Pro Met Phe," "Pro Thr Met Ser (SEQ ID NO:105)," and "Thr Met Ser" at the right end of these sequences represent amino acids found at the N-terminus of the capsid and GP proteins. The ubiquitinated constructs have additional N-terminal residues not found in the 13.2.2 and 13.4.6 helpers. The right-most box indicates the 3' RsrII restriction site and amino acids coded as a result of the primary nucleotide sequence. The left-most box represents critical residues for cleavage of ubiquitin from VEE structural proteins and indicates the portion of the nucleotide sequence (SEQ ID NO:106) encoding these residues.

In eukaryotic cells, proteins fused or tagged with ubiquitin are cleaved immediately after its C-terminal glycine by cellular ubiquitin carboxyl-terminal hydrolase (UCH) (Pickart and Rose, J. Biol. Chem. 260:7903-7910 (1985)). Placing a monomer of the ubiquitin coding sequence in-frame just upstream from the capsid and glycoprotein coding sequences will eliminate the fusion proteins produced with certain promoterless helper constructs of this invention (such fusions resulting from multiple transcriptional start sites upstream of the ATG for each structural protein coding sequence). The elimination occurs because all in-frame fusion proteins will include the ubiquitin monomer, and so they will be cleaved by UCH, thereby releasing full-length VEE structural proteins without any upstream, exogenous protein sequence. Primers ubiquitin F (SEQ ID NO: 96) and ubiquitin R (SEQ ID NO: 97) (Table 14) were designed to introduce RsrII sites at the 5' and 3' ends of the amplified ubiquitin monomer coding sequence, while maintaining the Arg-Gly-Gly sequence necessary for cleavage of the ubiquitin monomer by UCH (FIG. 4). These particular constructs resulted in additional N-terminal amino acid residue(s) on each of the resulting structural proteins following cleavage that are not present on the native structural proteins (i.e., for the capsid helper, an extra proline; for the glycoprotein helper, extra proline and threonine) (FIG. 4).

The ubiquitin coding sequence was PCR amplified using Pfu Taq polymerase (Stratagene) and cloned into the unique RsrII sites of dHcap(FL) and dHgp(FL). Transformants were screened to determine the orientation of the ubiquitin insert. Positive ubiquitin clones for capsid and glycoprotein, designated dHcapU and dHgpU, respectively (and with 5' end sequences provided herein as SEQ ID NOS. 53 and 54, respectively), were isolated and sequenced to confirm that no errors were introduced into the amplified ubiquitin coding sequence. RNAs for electroporation were transcribed in separate reactions from dHcapU, dHgpU, dHcap(FL), dHgp(FL), Hcap4, and 13.4.6 plasmids using the RiboMax Express RNA® kit and precipitated with lithium chloride.

B. VRP Generation Experiments Using Ubiquitin Modified Δ26S Helpers

Vero cells were electroporated with a VEE replicon RNA expressing an HIV clade C glycoprotein ("DU 151 gp 160") and selected combinations of promoterless capsid and GP helpers at the indicated RNA amounts. In some experiments, the "Hcap4" capsid helper was used. This is a helper that has a truncated 5' end (corresponding to the dHcap4 truncation described hereinabove) but retains the 26S subgenomic promoter sequence and is fully described in U.S. Pat. No. 7,045,335, which is incorporated herein by reference. Electroporations were performed at 500V, 25 μF, 4 pulses in a 0.4 cm cuvette in a volume of approximately 0.8 ml. Each electroporation was seeded into 1-850 cm² roller bottle with 100 ml Optipro® (Gibco, Carlsbad, Calif.). VRP were harvested at 18 hrs on a 0.2 μm filter with 25 ml of 0.5M NaCl wash. VRP salt wash material was titered with the anti-gp120 goat antibody (which recognizes the HIV gp160 protein) at 1:400. Results of packaging experiments are shown in Table 15.

Electroporations were subsequently performed to compare titers of various nucleic acids packaged with capsid helpers dHcapU or dHcap6-mut1(W-stop) combined with dHgp6-mut1. VRPs were titered using a VEE nsP2 specific polyclonal antibody (Table 16).

C. Structural Protein Expression by Western Analysis in Electroporated Cells

Figure 5:
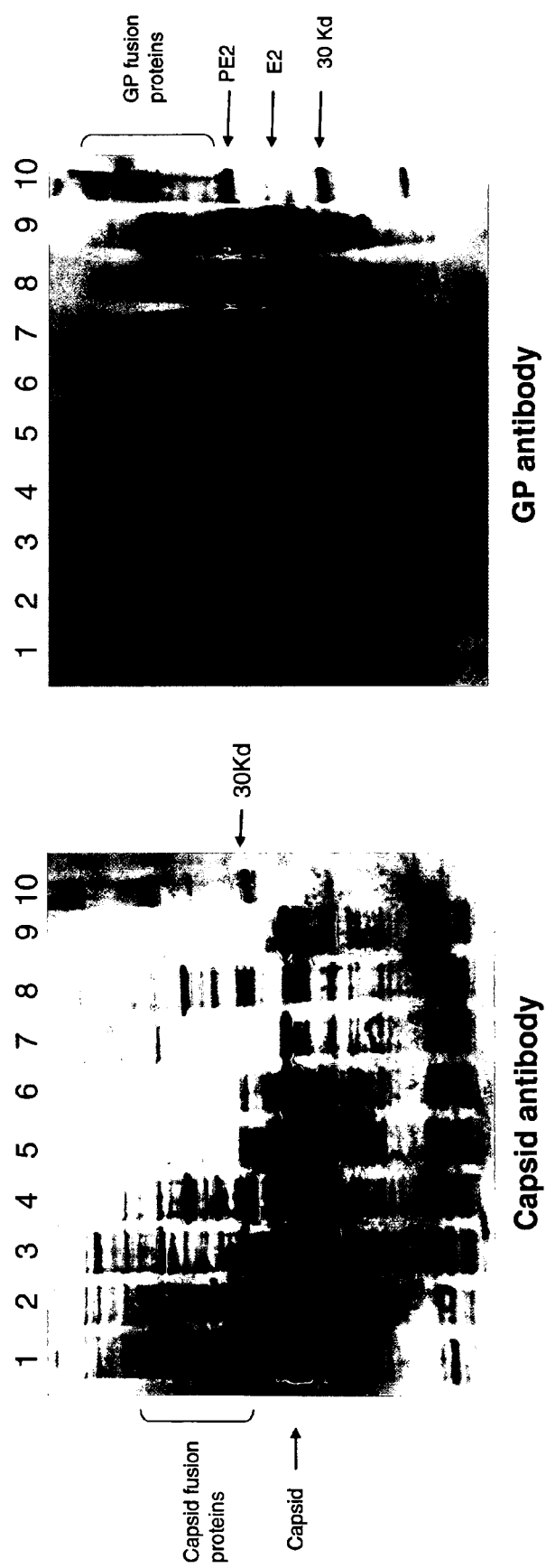
FIG. 5 shows Western blot analyses (one using capsid-specific antibody and the other using glycoprotein (GP)-specific antibody) of cell lysates generated from cells electroporated to produce VRP in a packaging study (Table 10). Two RNA helpers, in addition to a replicon, were electroporated into the cells as follows: Lane 1, dHcap6-mut1 and 13.4.6 (GP); Lane 2, Hcap4 and dHgp6-mut1; Lane 3, dHcapU and dHgpU; Lane 4, dHcap(FL) and dHgp(FL); Lane 5, Hcap4 and dHgpU; Lane 6, Hcap4 and dHgp(FL); Lane 7, dHcapU and 13.4.6; Lane 8, dHcap(FL) and 13.4.6; Lane 9, Hcap4 and 13.4.6; Lane 10, molecular weight markers.

Cell lysates were prepared from the cells used to generate VRP in the packaging study summarized in Table 16. Cell lysates from each sample were electrophoresed in 4-12% Bis-Tris Novex gels at 200V, 400 mA in 1×MOPS for 45 min prior to semidry transfer to PVDF at 400 mA in 1× transfer buffer for 40 min. Membranes were blocked overnight in 1×BMB block/TBS. Primary antibodies were a 1:500 dilution of 1A4A anti-VEE GP and a 1:1500 dilution of anti-VEE capsid in 1×BMB block/TBS. Western blot results are shown in FIG. 5. The glycoprotein expressed from dHgpU is processed into the PE2 and E2 GP forms more completely than the glycoprotein expressed from dHgp(FL). This is demonstrated by the difference in the pattern of fusion proteins seen without the ubiquitin present in dHgp(FL) (FIG. 5, compare lanes 3 and 4 on the Western blot using GP antibody). Placement of the ubiquitin protein at the N-terminus of the capsid protein in the dHcapU helper resulted in the disappearance of the capsid fusion proteins (FIG. 5) and a greater than 2 log increase in gp160 titer when packaged with the 13.4.6 glycoprotein helper (Table 15).

Figure 6:
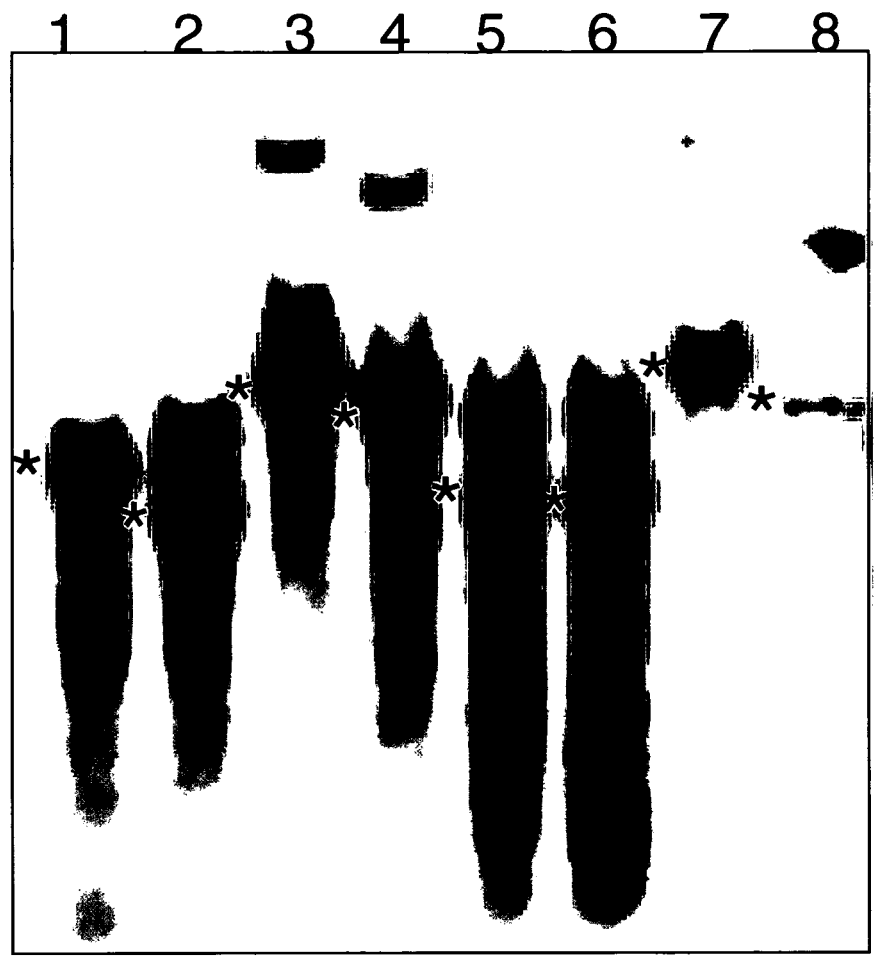
FIG. 6 shows a Northern blot analysis of capsid helper RNAs produced in Vero cells into which two RNA helpers, in addition to a replicon, were electroporated into the cells as follows: Lane 1, dHcap6-mut1 and 13.4.6 (GP); Lane 2, Hcap4 and dHgp6-mut1; Lane 3, dHcapU and dHgpU; Lane 4, dHcap(FL) and dHgp(FL); Lane 5, Hcap4 and dHgpU; Lane 6, Hcap4 and dHgp(FL); Lane 7, dHcapU and 13.4.6; Lane 8, dHcap(FL) and 13.4.6. The translatable capsid RNA molecule in each lane is marked with an asterisk.
Figure 7:
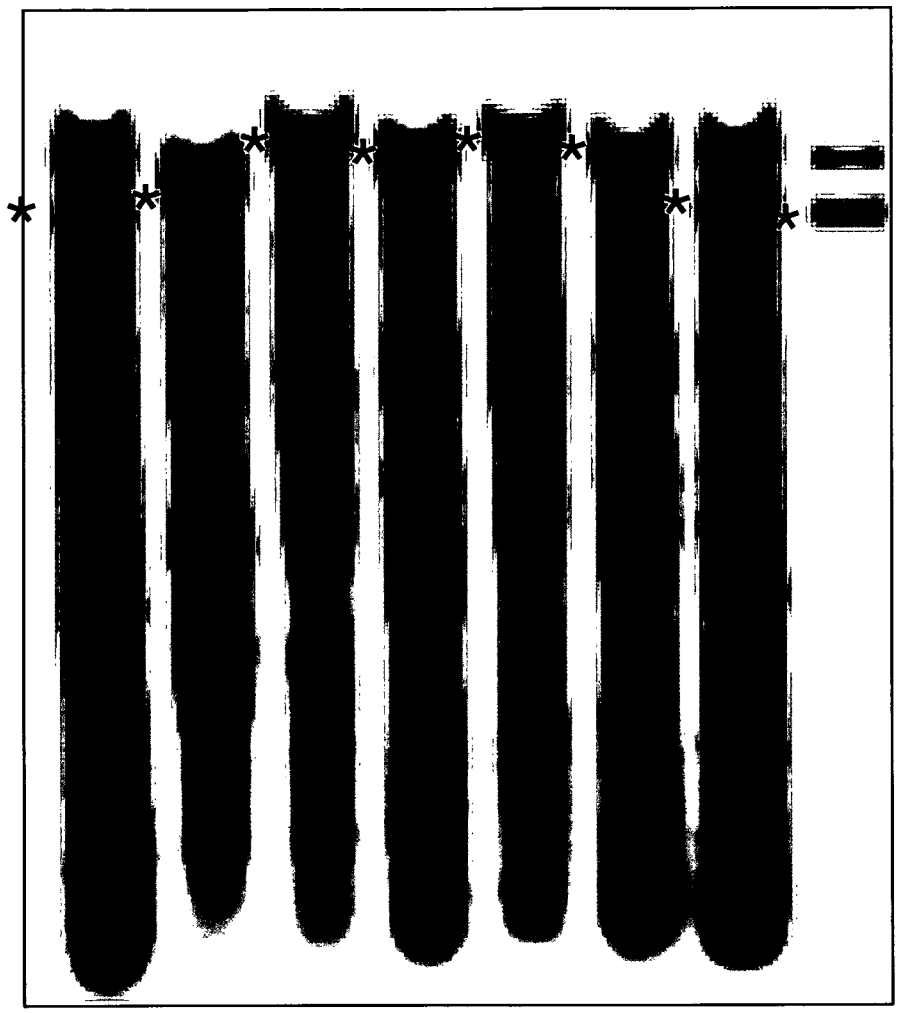
FIG. 7 shows a Northern blot analysis of glycoprotein (GP) helper RNAs produced in Vero cells into which two RNA helpers, in addition to a replicon, were electroporated into the cells as follows: Lane 1, dHcap6-mut1 and 13.4.6 (GP); Lane 2, Hcap4 and dHgp6-mut1; Lane 3, dHcapU and dHgpU; Lane 4, dHcap(FL) and dHgp(FL); Lane 5, Hcap4 and dHgpU; Lane 6, Hcap4 and dHgp(FL); Lane 7, dHcapU and 13.4.6; Lane 8, dHcap(FL) and 13.4.6. The translatable glycoprotein RNA molecule in each lane is marked with an asterisk.

D. Structural Protein RNA Expression by Northern Analysis of Electroporated Cells Total cellular RNA was extracted from the cells used to generate VRP in the packaging study summarized in Table 15. The cells were lysed with RNAwiz® reagent (Ambion, Inc., Austin, Tex.), extracted with chloroform, precipitated, and subjected to Northern analysis using capsid and GP specific probes (FIG. 6 and FIG. 7, respectively). All RNA species are consistent with the sizes expected from the various constructs.

Example 9

VRP Generation Using Capped and Non-Capped Δ26S Helper Constructs

A. VRPs Expressing the Glycoproteins of Various Alphaviruses

VRPs were produced using VEE replicons that express, as the nucleic acid of interest (NOI), the coding sequence for the glycoproteins of either VEE (3022), Eastern equine encephalitis virus (EEE) (4200) or Western equine encephalitis virus (WEE) (2100), in which each furin cleavage site has been deleted. DNA plasmids encoding the helpers used to generate the VRP were linearized with NotI and in vitro transcribed using a T7 RiboMax® kit (Promega, Madison Wis.) following the manufacturer's instructions, and where indicated, supplemented with 7.5 mM CAP analog (Promega). Helpers produced with cap analog are indicated as "+Cap" and those without cap analog are indicated as "−Cap" in Table 17. Vero cells were electroporated with combinations of replicon, capsid helper and GP helper RNAs and VRP were produced as described in Example 5 hereinabove. The results of three separate experiments are shown in Tables 17-19.

B. VRP Expressing the HA Coding Sequence of Influenza Strain Wisconsin

In this experiment, the molar ratios of the Cap analog to GTP were varied in the transcription reactions for producing Δ26S helper RNAs encoding either VEE capsid or VEE glycoproteins. The transcription reactions were assembled as follows: Promega 5× transcription buffer; rNTP mix (6 mM UTP, CTP, ATP); GTP (at 0-6 mM, as indicated in the table); (Promega Corporation Woods Hollow Rd., Madison Wis., catalog #P1300) and Ribo m⁷G Cap® analog (6 mM) (Promega Corporation Woods Hollow Rd., Madison Wis., catalog #P1712). Additional reactions were made with Promega's 5× buffer and 7.5 mM rNTPs with and without 7.5 mM Ribo m⁷G Cap analog to mimic the T7 RiboMAX Express® RNA transcription kit conditions (Promega Corporation Woods Hollow Rd., Madison Wis., catalog #P 1320) specified by the manufacturer, which is typically run with the 2× buffer supplied with the kit. The VEE replicon that was packaged in this experiment encoded the influenza HA (A/WI/05) protein. Thirty μg of the replicon RNA; 10 μg of a Δ26S capsid helper RNA, and 60 μg of a Δ26S glycoprotein helper RNA were used for each electroporation. Vero cells were expanded, then washed and resuspended in sucrose buffer to $1.2 \times 10^8$ cells/mL. These cells were mixed with the RNAs, then electroporated with the BioRad Gene Pulse II® apparatus set to 500 volts, 25 μFd and four pulses. Cells were transferred to roller bottles with 100 mL OptiPro® and incubated at 37° C. Twenty-four hours post-electroporation, VRPs were harvested. The VRPs were titered on 48-well plates of Vero and results are shown in Table 25.

Example 10

Protection Against Botulinum Neurotoxins in Mice Using VRPs Made with Δ26S Helper Constructs VEE replicon vectors that express the non-toxic c-terminal fragment of the heavy chain of either botulinum neurotoxin serotype A or B (BoNT A or BoNT B, respectively) were packaged into VRPs using either: (i) 30 μg each of uncapped 13.2.2 and 13.4.6 helpers, or (ii) 20 μg of the capped capsid Δ26S helper and 60 μg of the capped glycoprotein Δ26S helper, as described in Example 5. These VRPs were used at a dose of $1 \times 10^7$ IU to vaccinate Swiss mice two times at day 0 and day 28. The mice were then challenged with 1000 times the dose required to kill 50 percent of animals (1000 $LD_{50}$) of either BoNT A or BoNT B neurotoxin one month after the second immunization. The results of the challenge experiment are summarized in Table 20.

Example 11

Immunogenicity and Protection Studies with VRPs Expressing Antigens from the Smallpox Virus A. Immunogenicity in Mice and Primates of VRP Generated Using Δ26S Helper Constructs.

VEE replicon vectors optimized to express four vaccinia virus (VACV) genes (L1R, B5R, A27L and A33R) were constructed using the method described by Kamrud et al. (*Virology* 360(2):376-87 (2007)). The four VACV genes are collectively referred to as "4pox." The 4pox genes were cloned into two different VEE replicon vector systems, one based on the 3014 strain of VEE and the other based on the TC-83 vaccine strain. Each optimized VACV coding sequence-expressing replicon vector was used to generate VRPs by combining 30 μg of the replicon, 20 μg of Δ26S capsid helper RNA, and 60 μg of Δ26S GP helper RNA and electroporating them into Vero cells. Particles were produced and collected as described in Example 5. The individual VACV VRPs were then combined, producing a 4pox VRP mixture used to immunize either BALB/c mice or Cynomolgus macaques and the humoral responses were measured by VACV antigen-specific ELISA analysis. The VACV-specific ELISA responses detected in vaccinated mice are shown in Table 21 and the VACV-specific ELISA responses detected in vaccinated macaques are shown in Table 22.

B. Protection in Mice and Non-Human Primates Using the 4pox VRPs

1. Mice

Mice were challenged by the intranasal route with $2 \times 10^6$ PFU of vaccinia virus (strain IHD-J), and the results are presented in Table 23.

2. Non-Human Primates

Non-human primates were challenged by the intravenous route with $5 \times 10^6$ PFU of monkeypox virus. The World Health Organization's lesion count scoring system was used to determine disease severity, and the results are presented in Table 24.

As will be understood by one skilled in the art, there are several embodiments and elements for each aspect of the claimed invention, and all combinations of different elements are incorporated herein as embodiments of this invention, so the specific combinations exemplified herein are not to be construed as limitations in the scope of the invention as claimed. If specific elements are removed or added to the group of elements available in a combination, then the group of elements is to be construed as having incorporated such a change.

All references cited herein, including non-patent publications, patent applications, and patents, are incorporated by reference herein in their entireties to the same extent as if each was individually and specifically indicated to be incorporated by reference, and was reproduced in its entirety herein.

TABLE 1

Primers to generate Δ26S helpers

| Primer name | 5' primer sequence 3' | SEQ ID NO: |
|---|---|---|
| Capsid F | CCTCGGACCGATGTTCCCGTTCCAGCCAATG | 98 |
| GP F | CCTCGGACCGACCATGTCACTAGTGACCACCATG | 60 |
| 13-101.pr4 | TTTTTTTTTTTTTTTTTTTTTTTTTTTTTTTTTTTTTTTGAAATATTAAAAACAAAATCCGATTCGG | 61 |
| 3-16.1.1 | ACCGTCACCCTGGATGCTGT | 62 |
| dHelp1 R | CCTCGGACCGAAACAGCGACTTGCCCTTCGTAGCGACAC | 63 |
| dHelp2 R | CCTCGGACCGCATAGTCTCAGTTTCCAGGTCAGGGTCGC | 64 |
| dHelp3 R | CCTCGGACCGCGGCGAGCTCCTTCATTTTCTTGTCCAATTCCT | 65 |
| dHelp4 R | CCTCGGACCGCAGCTTAGTTGCATACTTATACAATCTGTCCGGA | 66 |

TABLE 1-continued

Primers to generate Δ26S helpers

| Primer name | 5' primer sequence 3' | SEQ ID NO: |
|---|---|---|
| dHelp5 R | CCTCGGACCGACATCTCATCGGACAGATACAATGATACTTGTGCT | 67 |
| dHelp6 R | CCTCGGACCGTCCAATGTCAAGGATCGTGTCGGATGGGT | 68 |
| dHelp7 R | CCTCGGACCGAGTTTTGAAGCCAGATGCGAAAACGCTCTG | 69 |
| dHelp8 R | CCTCGGACCGCTTGGCTTCTACCTCAAACTGCGGGAAGC | 70 |

TABLE 2

IFA analysis of dHcap1-8 helpers

| Helper | Anti-capsid IFA |
|---|---|
| dHcap1 | Positive |
| dHcap2 | Positive |
| dHcap3 | Positive |
| dHcap4 | Positive |
| dHcap5 | Positive |
| dHcap6 | Positive |
| dHcap7 | Positive |
| dHcap8 | Positive (weak) |

TABLE 3

| Helper | Anti-GP IFA |
|---|---|
| DHgp1 | Positive |
| dHgp2 | Positive |
| dHgp3 | Positive |
| dHgp4 | Positive |
| dHgp5 | Positive |
| dHgp6 | Positive |
| dHgp7 | Positive |
| dHgp8 | Negative |

TABLE 4

Site directed mutagenesis primers to generate mut1 helpers

| Primer name | 5' primer sequence 3' | SEQ ID NO |
|---|---|---|
| Mut1 F | GACCAATTACCTACCCAAATAGGAGAAAGTTCACGTTGAC | 71 |
| Mut1 R | GTCAACGTGAACTTTCTCCTATTTGGGTAGGTAATTGGTC | 72 |

TABLE 5

Primers used to change 5' replication recognition sequence ATG codons to GTG

| Primer name (location of A residue in ATG codon) | 5' primer sequence 3' | SEQ ID NO |
|---|---|---|
| nt-12 | ATAGGCGGCGCGTGAGAGAAGCCCAG | 73 |
| nt-45 | CCTACCCAAAGTGGAGAAAGTTCACGTTGACATC | 74 |
| nt-148/154/160 | CAGGTCACTGATAGTGACCGTGCTAGTGCCAGAGCG | 75 |
| nt-259 | GCCCGCCCGCAGAGTGTATTCTAAGCAC | 76 |
| nt-295/300 | GTATCTGTCCGGTGAGGTGTGCGGAAGATCCG | 77 |

TABLE 5-continued

Primers used to change 5' replication recognition sequence ATG codons to GTG

| Primer name (location of A residue in ATG codon) | 5' primer sequence 3' | SEQ ID NO |
|---|---|---|
| nt-331 | GACAGATTGTATAAGTGTGCAACTAAGCTG | 78 |
| nt-390 | GAATGGACAAGAAAGTGAAGGAGCTC | 79 |
| nt-411 | CCGTCGTGAGCGACCCTGACCTGGAAAC | 80 |
| nt-441 | GAAACTGAGACTGTGTGCCTCCACG | 81 |
| nt-499 | GTTTACCAGGGTGTATACGCGGTTG | 82 |

TABLE 6

| Capsid helper | GP helper | VRP yield |
|---|---|---|
| BoNT B replicon | | |
| dHcap6 mut1 (30 μg) | 13.4.6 (30 μg) | $9.0 \times 10^9$ |
| BoNT A replicon | | |
| dHcap6 (30 μg) | dHgp7 (30 μg) | $6.0 \times 10^9$ |
| dHcap6 (30 μg) | dHgp7 (90 μg) | $2.6 \times 10^{10}$ |
| dHcap5-mm (30 μg) | dHgp6 mut1 (90 μg) | $1.8 \times 10^7$ |
| dHcap6-mm (30 μg) | dHgp6 mut1 (90 μg) | $3.6 \times 10^8$ |
| dHcap7-mm (30 μg) | dHgp6 mut1 (90 μg) | $1.3 \times 10^8$ |
| dHcap4 mut1 (30 μg) | dHgp6 mut1 (90 μg) | $1.3 \times 10^9$ |
| dHcap6 mut1 (30 μg) | dHgp6 mut1 (90 μg) | $4.6 \times 10^9$ |
| dHcap7 mut1 (30 μg) | dHgp6 mut1 (90 μg) | $6.2 \times 10^9$ |
| dHcap5-mm (10 μg) | dHgp6 mut1 (90 μg) | $4.2 \times 10^6$ |
| dHcap6-mm (10 μg) | dHgp6 mut1 (90 μg) | $2.6 \times 10^8$ |
| dHcap7-mm (10 μg) | dHgp6 mut1 (90 μg) | $4.4 \times 10^7$ |

TABLE 6-continued

| Capsid helper | GP helper | VRP yield |
|---|---|---|
| dHcap4 mut1 (10 μg) | dHgp6 mut1 (90 μg) | $1.1 \times 10^{10}$ |
| dHcap6 mut1 (10 μg) | dHgp6 mut1 (90 μg) | $1.9 \times 10^{10}$ |
| dHcap7 mut1 (10 μg) | dHgp6 mut1 (90 μg) | $1.8 \times 10^{10}$ |
| SARS S replicon | | |
| dHcap4 mut1 (10 μg) | dHgp6 mut1 (90 μg) | $4.4 \times 10^9$ |
| dHcap6 mut1 (10 μg) | dHgp6 mut1 (90 μg) | $2.6 \times 10^9$ |
| dHcap7 mut1 (10 μg) | dHgp6 mut1 (90 μg) | $1.4 \times 10^9$ |
| BoNT A replicon | | |
| dHcap1 (30 μg) | 13.4.6 (30 μg) | $3.0 \times 10^7$ |
| dHcap2 (30 μg) | 13.4.6 (30 μg) | $9.2 \times 10^7$ |
| dHcap3 (30 μg) | 13.4.6 (30 μg) | $2.0 \times 10^8$ |
| dHcap4 (30 μg) | 13.4.6 (30 μg) | $1.3 \times 10^9$ |
| dHcap5 (30 μg) | 13.4.6 (30 μg) | $3.2 \times 10^8$ |
| dHcap6 (30 μg) | 13.4.6 (30 μg) | $3.0 \times 10^8$ |
| dHcap7 (30 μg) | 13.4.6 (30 μg) | $1.2 \times 10^9$ |
| dHcap8 (30 μg) | 13.4.6 (30 μg) | $1.8 \times 10^7$ |
| dHcap6 mut1 (30 μg) | 13.4.6 (30 μg) | $8.4 \times 10^9$ |
| dHcap6 mut1 (30 μg) | 13.4.6 (30 μg) | $1.2 \times 10^{10}$ |

TABLE 7

VRP yield generated using Δ26S capsid, E1 and E2 helpers. pERK/342/MS/BoNT A [30 μg]

| Capsid helper | GP helper #1 | GP helper #2 | VRP titer/ml |
|---|---|---|---|
| dHcap6-mut1 [10 μg] | dHE1-6M1 [30 μg] | dHE2-6M1 [30 μg] | $2.2 \times 10^7$ |
| dHcap6-mut1 [10 μg] | dHgp7-mut1 [90 μg] | | $1.3 \times 10^9$ |

TABLE 8

PCR primers used to design modifications to the 5' and 3' regions of Δ26S helpers

| Primer name | 5' primer sequence 3' | SEQ ID NO: |
|---|---|---|
| 13-82.1.9 | TCAGTGGAACGAAAACTCACG | 83 |
| dSL2(EcoRV) R | TTTGATATCGGTAATTGGTCTGGGCTTCTC | 84 |
| dSL2 (EcoRV) F | TTTGATATCGAAGCCAAGCAGGTCACTG | 85 |
| 3-8.pr4 | GCAACGCGGGGAGGCAGACA | 86 |
| GP (SphI) R | GCATGCTCAATTATGTTTCTGGTTGG | 87 |
| 3-16.1.3 | CGACATAGTCTAGTCCGCCA | 88 |
| 3' trunc (SphI) F | GCATGCATTTTGTTTTTAATATTTCAAA | 89 |
| 3' trunc (AflIII) R | GCTCACATGTTCTTTCCTGCG | 90 |
| Capsid (RsrII-Kozak) F | CCTCGGACCGACCATGTTCCCGTTCCAGCCAATG | 91 |
| Capsid (stop) SphI R | ACATGCATGCTTATTGCTCGCAGTTCTCCGG | 92 |
| Capsid (W-stop) SphI R | ACATGCATGCTTACCATTGCTCGCAGTTCTCCGG | 93 |
| Gp (RsrII-Ser) F | CCTCGGTCCGACCATGCTAGTGACCACCATG | 94 |
| 3-16.2.14 | ACATACACGGTAGTCACAAT | 95 |

TABLE 9

| Replicon packaged pERK/342/MS/BoNT A [30 μg RNA] | | |
| --- | --- | --- |
| Capsid helper [RNA] | GP helper [RNA] | VRP titer IFU/ml |
| dHcap7-mut1 (W-stop) [10 μg] | dHgp7-mut1 [90 μg] | $1.0 \times 10^8$ |
| dHcap6-mut1 (W-stop) [10 μg] | dHgp7-mut1 [90 μg] | $8.9 \times 10^8$ |
| dHcap7-mut1 (W-stop) [20 μg] | dHgp7-mut1 [90 μg] | $3.0 \times 10^8$ |
| dHcap6-mut1 (W-stop) [20 μg] | dHgp7-mut1 [90 μg] | $6.8 \times 10^8$ |

TABLE 10

| Replicon packaged pERK/342/MS/BoNT A [30 μg RNA] | | |
| --- | --- | --- |
| Capsid helper [RNA] | GP helper [RNA] | VRP titer IFU/ml |
| dHcap6-mut1 [10 μg] | dHgp7-mut1 [60 μg] | $2.1 \times 10^8$ |
| dHcap6-mut1 (W-stop) [10 μg] | dHgp7-mut1 [60 μg] | $2.0 \times 10^8$ |
| dHcap6-mut1 (W-stop)-dSL2 [10 μg] | dHgp7-mut1 [60 μg] | $3.7 \times 10^7$ |

TABLE 11

| Replicon packaged pERK/342/MS/BoNT A [30 μg RNA] | | |
| --- | --- | --- |
| Capsid helper [RNA] | GP helper [RNA] | VRP titer IFU/ml |
| dHcap7-mut1 [20 μg] | dHgp7-mut1 [90 μg] | $4.9 \times 10^7$ |
| dHcap7-mut1 19nt [30 μg] | dHgp7-mut1 [90 μg] | $2.2 \times 10^7$ |

TABLE 12

| Replicon packaged pERK/342/MS/BoNT A [30 μg RNA] | | |
| --- | --- | --- |
| Capsid helper [RNA] [10 μg] | Glycoprotein helper [RNA] [60 μg] | VRP titer IFU/ml |
| dHcap7-mut1 (W-stop) | dHgp6-mut1 | $6.1 \times 10^6$ |
| dHcap7-mut1 (W-stop) | dHgp6-mut1-dSL2 (-S) | $6.6 \times 10^5$ |
| dHcap7-mut1 (W-stop) | dHgp6-mut1-dSL2 (-S) 19 nt | $9.6 \times 10^4$ |
| dHcap7-mut1 (W-stop) | dHgp6-mut1 (-S) | $1.0 \times 10^7$ |
| dHcap6-mut1 (W-stop) | dHgp6-mut1 | $2.7 \times 10^7$ |
| dHcap6-mut1 (W-stop) | dHgp6-mut1-dSL2 (-S) | $1.7 \times 10^6$ |
| dHcap6-mut1 (W-stop) | dHgp6-mut1-dSL2 (-S) 19 nt | $1.2 \times 10^5$ |
| dHcap6-mut1 (W-stop) | dHgp6-mut1 (-S) | $2.2 \times 10^7$ |

TABLE 13

| pERK/383/MS/HA (A Wyoming) [30 μg RNA] | | |
| --- | --- | --- |
| Capsid helper [RNA] | GP helper [RNA] | VRP titer IFU/ml |
| dHcap6-mut1 (W-stop) [20 μg] | dHgp6-mut1 [60 μg] | $2.0 \times 10^8$ |
| dHcap6-mut1 (W-stop) capped [20 μg] | dHgp6-mut1 capped [60 μg] | $9.0 \times 10^9$ |
| dHcap6-mut1 (W-stop) [10 μg] | dHgp6-mut1 [90 μg] | $2.5 \times 10^7$ |
| dHcap6-mut1 (W-stop) capped [10 μg] | dHgp6-mut1 capped [90 μg] | $2.5 \times 10^8$ |
| dHcap6-mut1 (W-stop) [10 μg] | dHgp6-mm [90 μg] | $2.3 \times 10^7$ |
| dHcap6-mut1 (W-stop) capped [10 μg] | dHgp6-mm capped [90 μg] | $2.4 \times 10^8$ |

TABLE 14

| Primer name | 5' primer sequence 3' | SEQ ID NO: |
| --- | --- | --- |
| Ubiquitin F | CATCGACGGACCGATGCAGATCTTCGTGAAGACCC | 96 |
| Ubiquitin R | GATTTTCGGTCCGCCCCTCAGACGGAGGACCAGG | 97 |

TABLE 15

| VRP generation using ubiquitin-modified Δ26S helper combinations | | | |
| --- | --- | --- | --- |
| Replicon RNA [30 μg] | Capsid helper | Glycoprotein helper [60 μg] | VRP titer/ml |
| DU151gp160 | dHcap(FL) [10 μg] | 13.4.6 | $8.3 \times 10^5$ |
| DU151gp160 | dHcapU [10 μg] | 13.4.6 | $1.3 \times 10^8$ |
| DU151gp160 | Hcap4 [30 μg] | dHgp6-mut1 | $9.3 \times 10^7$ |
| DU151gp160 | dHcap6-mut1 (W-stop) [10 μg] | 13.4.6 | $5.6 \times 10^8$ |

TABLE 16

VRP generation using multiple replicon vectors
and modified Δ26S helper combinations

| Replicon RNA [30 µg] | Capsid helper [10 µg] | GP helper [60 µg] | VRP titer/ml |
|---|---|---|---|
| BoNT A | dHcapU | dHgp6-mut1 | $1.4 \times 10^8$ |
| BoNT A | dHcap6-mut1 (W-stop) | dHgp6-mut1 | $3.6 \times 10^8$ |
| BoNT E | dHcapU | dHgp6-mut1 | $3.2 \times 10^7$ |
| BoNT E | dHcap6-mut1 (W-stop) | dHgp6-mut1 | $1.4 \times 10^8$ |
| HA (A Wyoming) | dHcapU | dHgp6-mut1 | $3.8 \times 10^8$ |
| HA (A Wyoming) | dHcap6-mut1 (W-stop) | dHgp6-mut1 | $6.4 \times 10^8$ |
| NA (A Wyoming) | dHcapU | dHgp6-mut1 | $4.0 \times 10^8$ |
| NA (A Wyoming) | dHcap6-mut1 (W-stop) | dHgp6-mut1 | $5.3 \times 10^8$ |
| CEA | dHcapU | dHgp6-mut1 | $2.0 \times 10^8$ |
| CEA | dHcap6-mut1 (W-stop) | dHgp6-mut1 | $3.1 \times 10^8$ |

TABLE 17

Comparison of use of Capped vs. Non-capped Helpers

| NOI in VEE replicon | Helpers | +/−Cap | IU/cell |
|---|---|---|---|
| VEE glycoprotein 3022 | 13.2.2; 13.4.6 | −Cap | 131.1 |
| VEE glycoprotein 3022 | 13.2.2; 13.4.6 | +Cap | 1095.4 |
| VEE glycoprotein 3022 | Δ26S helpers (C & GP) | −Cap | 49.0 |
| VEE glycoprotein 3022 | Δ26S helpers (C & GP) | +Cap | 508.8 |
| EEE glycoprotein 4200 | 13.2.2; 13.4.6 | −Cap | 30.7 |
| EEE glycoprotein 4200 | 13.2.2; 13.4.6 | +Cap | 398.8 |
| EEE glycoprotein 4200 | Δ26S helpers (C & GP) | −Cap | 9.3 |
| EEE glycoprotein 4200 | Δ26S helpers (C & GP) | +Cap | 88.0 |

TABLE 18

| NOI in VEE replicon | Helpers | +/−Cap | IU/cell |
|---|---|---|---|
| VEE glycoprotein 3022 | 13.2.2; 13.4.6 | −Cap | 600.4 |
| VEE glycoprotein 3022 | 13.2.2; 13.4.6 | +Cap | 2035.0 |
| VEE glycoprotein 3022 | Δ26S helpers (C & GP) | −Cap | 101.3 |
| VEE glycoprotein 3022 | Δ26S helpers (C & GP) | +Cap | 884.6 |
| EEE glycoprotein 4200 | 13.2.2; 13.4.6 | −Cap | 75.2 |
| EEE glycoprotein 4200 | 13.2.2; 13.4.6 | +Cap | 898.3 |
| EEE glycoprotein 4200 | Δ26S helpers (C & GP) | −Cap | 29.8 |
| EEE glycoprotein 4200 | Δ26S helpers (C & GP) | +Cap | 206.3 |

TABLE 19

| NOI in VEE replicon | Δ26S Capsid Helper (+/−cap) | Δ26S GP Helper (+/−cap) | IU/cell |
|---|---|---|---|
| WEE glycoprotein 2100 | −cap | −cap | 37.1 |
| WEE glycoprotein 2100 | +cap | +cap | 285.7 |
| WEE glycoprotein 2100 | +cap | −cap | 38.6 |
| WEE glycoprotein 2100 | −cap | +cap | 34.3 |

TABLE 20

Results from challenge of mice vaccinated
with VRP produced using Δ26S helpers

| Replicon (helper set) | Survival BoNT-A/total | Survival BoNT-B/total |
|---|---|---|
| MS/342/BoNT A (13.2.2 + 13.4.6) | 8/10 | NA |
| MS/342/BoNT A (Δ26S capsid + gp) | 10/10 | NA |
| Control VRP[1] | 0/10 | NA |
| MS/357/BoNT B (13.2.2 + 13.4.6) | NA | 10/10 |
| MS/357/BoNT B ((Δ26S capsid + gp) | NA | 8/10 |
| Control VRP[1] | NA | 0/10 |

NA: not applicable

[1]Contains irrelevant protein-expressing coding sequence in replicon

TABLE 21

| Replicon expressing 4pox | Dose (IU) | Log10 VACV-specific ELISA titer | | | |
|---|---|---|---|---|---|
| | | L1R | B5R | A27L | A33R |
| V3014 | $1 \times 10^6$ | 2 | 3 | 1 | 3 |
| TC-83 | $1 \times 10^6$ | 3 | 4 | 1 | 4 |
| V3014 | $1 \times 10^7$ | 3 | 4 | 3 | 4 |
| TC-83 | $1 \times 10^7$ | 4 | 4 | 1 | 4 |

TABLE 22

| Replicon expressing 4pox | Dose (IU) | Log10 VACV-specific ELISA titer | | | |
|---|---|---|---|---|---|
| | | L1R | B5R | A27L | A33R |
| TC-83 | $1 \times 10^8$ | 3.2 | 2.4 | 2.2 | 3.2 |
| V3014 | $1 \times 10^8$ | 3.6 | 2.6 | 2 | 3.6 |

TABLE 23

Protection Study in Mice

| VRP vaccine | # mice tested | % survival |
|---|---|---|
| V3014 4pox | 48 | 100% |
| V3014 control | 24 | 0% |
| TC-83 4pox | 40 | 100% |
| TC-83 control | 24 | 9% |

TABLE 24

Protection study in Macaques

| Vaccine | VRP System | Animal # | Challenge Outcome* | Max pock count |
|---|---|---|---|---|
| 4pox VRP | V3014 | 1 | No disease | 0 |
| | | 2 | Mild disease | 2 |
| | | 3 | Mild disease | 8 |
| | | 4 | Mild disease | 4 |
| | | 5 | Mild disease | 12 |
| 4pox VRP | TC-83 | 1 | No disease | 0 |
| | | 2 | Mild disease | 8 |
| | | 3 | Mild disease | 12 |
| | | 4 | Mild disease | 10 |
| | | 5 | Mild disease | 8 |
| Control VRP | V3014 | 1 | Lethal disease | TNTC[1] |
| | | 2 | Lethal disease | TNTC |
| | | 3 | Lethal disease | TNTC |
| Control VRP | TC-83 | 1 | Lethal disease | TNTC |
| | | 2 | Grave disease | TNTC |
| | | 3 | Severe disease | >100 |

[1]TNTC = too numerous to count

TABLE 25

Study of effects of capping of Δ26S helpers on packaging of an alphavirus replicon vector encoding the HA coding sequence from influenza strain Wisconsin.

| EP | Buffer used in in vitro transcription reactions | Cap:GTP ratio Capsid | GP | Titer IU/mL | Total IU | IU/cell |
|---|---|---|---|---|---|---|
| 1  | 5X | 0:1 | 0:1 | 3.70E+08 | 9.26E+09 | 154 |
| 2  | 5X | 1:1 | 0:1 | 4.66E+08 | 1.16E+10 | 194 |
| 3  | 5X | 2:1 | 0:1 | 3.52E+08 | 8.80E+09 | 147 |
| 4  | 5X | 4:1 | 0:1 | 3.70E+08 | 9.26E+09 | 154 |
| 5  | 5X | 6:1 | 0:1 | 3.81E+08 | 9.54E+09 | 159 |
| 6  | 5X | 0:1 | 1:1 | 1.91E+08 | 4.77E+09 | 79 |
| 7  | 5X | 1:1 | 1:1 | 4.44E+08 | 1.11E+10 | 185 |
| 8  | 5X | 2:1 | 1:1 | 4.88E+08 | 1.22E+10 | 203 |
| 9  | 5X | 4:1 | 1:1 | 4.36E+08 | 1.09E+10 | 182 |
| 10 | 5X | 6:1 | 1:1 | 4.36E+08 | 1.09E+10 | 182 |
| 11 | 5X | 0:1 | 2:1 | 1.17E+08 | 2.93E+09 | 49 |
| 12 | 5X | 1:1 | 2:1 | 3.04E+08 | 7.61E+09 | 127 |
| 13 | 5X | 2:1 | 2:1 | 3.04E+08 | 7.61E+09 | 127 |
| 14 | 5X | 4:1 | 2:1 | 3.37E+08 | 8.44E+09 | 141 |
| 15 | 5X | 6:1 | 2:1 | 4.14E+08 | 1.04E+10 | 173 |
| 16 | 5X | 0:1 | 4:1 | 1.71E+08 | 4.26E+09 | 71 |
| 17 | 5X | 1:1 | 4:1 | 7.56E+08 | 1.89E+10 | 315 |
| 18 | 5X | 4:1 | 4:1 | 4.66E+08 | 1.16E+10 | 194 |
| 19 | 5X | 0:1 | 6:1 | 1.72E+08 | 4.31E+09 | 72 |
| 20 | 5X | 6:1 | 6:1 | 4.03E+08 | 1.01E+10 | 168 |
| 21 | 5X | 1:1 | 0:1 | 4.36E+08 | 1.09E+10 | 182 |
| 22 | 5X | 0:1 | 1:1 | 1.60E+08 | 3.99E+09 | 66 |
| 23 | 5X | 2:1 | 2:1 | 5.10E+08 | 1.27E+10 | 212 |
| 24 | 2X | 0:1 (7.5 mM) | 1:1 (7.5 mM) | 1.80E+08 | 4.49E+09 | 75 |
| 25 | 2X | 1:1 (7.5 mM) | 1:1 (7.5 mM) | 3.56E+08 | 8.89E+09 | 148 |
| 26 | 5X | 1:1 (7.5 mM) | 1:1 (7.5 mM) | 6.82E+08 | 1.71E+10 | 284 |
| 27 | 2X | 1:1 (7.5 mM) | 1:1 (7.5 mM) | 7.04E+08 | 1.76E+10 | 293 |
| 28 | 2X | 1:1 (7.5 mM) | 1:1 (7.5 mM) | 6.24E+08 | 1.56E+10 | 260 |
| 29 | 2X | 0:1 (7.5 mM) | 0:1 (7.5 mM) | 3.30E+08 | 8.25E+09 | 138 |
| 30 | 2X | 0:1 (7.5 mM) | 0:1 (7.5 mM) | 3.41E+08 | 8.53E+09 | 142 |

What is claimed is:

1. A method of making an alphavirus replicon particle, comprising introducing one or more of an isolated RNA molecule, which RNA comprises:
   a) an alphavirus 5' replication recognition sequence, wherein at least one initiation codon has been removed from the 5' replication recognition sequence;
   b) a nucleotide sequence encoding an alphavirus structural protein; and
   c) an alphavirus 3' replication recognition sequence,
with the proviso that the RNA molecule does not contain a promoter that directs transcription of the nucleotide sequence of (b), and wherein the alphavirus 5' and 3' replication recognition sequences of (a) and (c) direct replication of the entire RNA molecule in the presence of alphavirus nonstructural proteins; into a cell, wherein the RNA molecule comprises: i) an alphavirus 5' replication recognition sequence, wherein at least one initiation codon has been removed from the 5' replication recognition sequence; ii) a nucleotide sequence encoding an alphavirus structural protein; and iii) an alphavirus 3' replication recognition sequence, with the proviso that the RNA molecule does not contain a promoter that directs transcription of the nucleotide sequence of (ii), and wherein the alphavirus 5' and 3' replication recognition sequences of (i) and (iii) direct replication of the entire RNA molecule in the presence of nonstructural proteins,
whereby the combination of RNA molecules encodes all alphavirus structural proteins necessary for production of an alphavirus replicon particle, along with an alphavirus replicon RNA, under conditions whereby alphavirus replicon particles are produced.

2. The method of claim 1, wherein two RNA molecules are introduced into the cell, wherein a first RNA molecule of the two RNA molecules encodes one or more alphavirus structural proteins and a second RNA molecule of the two RNA molecules encodes one or more alphavirus structural proteins, at least one of which is different from the alphavirus structural proteins encoded by the first RNA molecule.

3. The method of claim 1, wherein three RNA molecules are introduced into the cell, wherein a first RNA molecule of the three RNA molecules encodes one or more alphavirus structural proteins and a second RNA molecule of the three RNA molecules encodes one or more alphavirus structural proteins, at least one of which is different from the alphavirus structural proteins encoded by the first RNA molecule and a third RNA molecule encodes one or more alphavirus structural proteins, at least one of which is different from the alphavirus structural proteins encoded by the first RNA molecule and the second RNA molecule.

4. The method of claim 1, wherein at least one of the one or more RNA molecules is capped at the 5' terminus.

5. A method of making an alphavirus replicon particle, comprising introducing into a cell:
   a) an alphavirus replicon RNA;
   b) one or more of an RNA molecule, wherein the RNA molecule comprises: i) an alphavirus 5' replication recognition sequence, wherein at least one initiation codon has been removed from the 5' replication recognition sequence; ii) a nucleotide sequence encoding an alphavirus structural protein; and iii) an alphavirus 3' replication recognition sequence, with the proviso that the RNA molecule does not contain a promoter that directs transcription of the nucleotide sequence of (ii), and wherein the alphavirus 5' and 3' replication recognition sequences of (i) and (iii) direct replication of the entire RNA molecule in the presence of nonstructural proteins; and
   c) one or more promoter-assisted alphavirus helper constructs,
whereby the combination of RNA molecules of (b) and helper constructs of (c) encodes all alphavirus structural proteins necessary for production of an alphavirus replicon particle, under conditions whereby an alphavirus replicon particle is produced.

6. The method of claim 5, wherein at least one of the one or more RNA molecules is capped at the 5' terminus.

* * * * *

UNITED STATES PATENT AND TRADEMARK OFFICE
CERTIFICATE OF CORRECTION

PATENT NO. : 8,460,913 B2
APPLICATION NO. : 12/665497
DATED : June 11, 2013
INVENTOR(S) : Kamrud et al.

It is certified that error appears in the above-identified patent and that said Letters Patent is hereby corrected as shown below:

In the Specification:
Column 1, Line 25: correct "entitled 9368-9X$_{13}$ST25.txt,"
to read -- entitled 9368-9X_ST25.txt, --

In the Claims:
Column 91, Claim 1, Lines 23-53: replace Claim 1 in its entirety so that it reads as follows:

-- A method of making an alphavirus replicon particle, comprising introducing one or more of an isolated RNA molecule into a cell, wherein the RNA molecule comprises: i) an alphavirus 5' replication recognition sequence, wherein at least one initiation codon has been removed from the 5' replication recognition sequence; ii) a nucleotide sequence encoding an alphavirus structural protein; and iii) an alphavirus 3' replication recognition sequence, with the proviso that the RNA molecule does not contain a promoter that directs transcription of the nucleotide sequence of (ii), and wherein the alphavirus 5' and 3' replication recognition sequences of (i) and (iii) direct replication of the entire RNA molecule in the presence of nonstructural proteins,
whereby the combination of RNA molecules encodes all alphavirus structural proteins necessary for production of an alphavirus replicon particle, along with an alphavirus replicon RNA, under conditions whereby alphavirus replicon particles are produced. --

Signed and Sealed this
Eighth Day of July, 2014

Michelle K. Lee
*Deputy Director of the United States Patent and Trademark Office*